(12) United States Patent
Curtis et al.

(10) Patent No.: US 7,517,659 B2
(45) Date of Patent: Apr. 14, 2009

(54) POTASSIUM CHANNEL MOLECULES AND USES THEREFOR

(75) Inventors: Rory A. J. Curtis, Southborough, MA (US); Inmaculada Silos-Santiago, Cambridge, MA (US)

(73) Assignee: Bayer Shering Pharma AG, Berlin (DE)

( * ) Notice: Subject to any disclaimer, the term of this patent is extended or adjusted under 35 U.S.C. 154(b) by 376 days.

(21) Appl. No.: 10/701,013

(22) Filed: Nov. 4, 2003

(65) Prior Publication Data

US 2004/0063179 A1 Apr. 1, 2004

Related U.S. Application Data

(60) Division of application No. 09/561,763, filed on Apr. 28, 2000, now Pat. No. 6,664,373, which is a continuation-in-part of application No. 09/431,367, filed on Nov. 1, 1999, now Pat. No. 6,670,149, which is a continuation-in-part of application No. 09/259,951, filed on Mar. 1, 1999, now abandoned.

(51) Int. Cl.
  *G01N 33/53* (2006.01)
(52) U.S. Cl. .................. 435/7.2; 435/7.21
(58) Field of Classification Search ............ None
  See application file for complete search history.

(56) References Cited

U.S. PATENT DOCUMENTS

| 5,856,155 A | 1/1999 | Li |
| 5,955,259 A | 9/1999 | Holmes et al. |
| 2003/0064433 A1* | 4/2003 | Roberds et al. ............ 435/69.1 |
| 2004/0224911 A1* | 11/2004 | Yue et al. .................. 514/44 |

FOREIGN PATENT DOCUMENTS

| EP | 930 364 A1 | 7/1999 |
| WO | WO 91/17174 | 11/1991 |
| WO | WO 96/22371 | 7/1996 |
| WO | WO 00/05367 | 2/2000 |
| WO | WO 00/52164 | 9/2000 |

OTHER PUBLICATIONS

Duprat F., et al., "Task, a Human Background K+ Channel to Sense External pH Variations Near Physiological pH," EMBO J. 16(7):5464-5471 (1997).
The *C. elegans* Sequencing Consortium, "Genome Sequence of the Nematode *C. elegans*: A Platform for Investigating Biology," Science 282(5396):2012-2018 (1998).
Database EMBL Accession No. AA553991, "*Homo sapiens* cDNA Clone Image: 1015480 3', mRNA Sequence." Strausberg, Robert (Sep. 11, 1997).
Database EMBL Accession No. AI740592, "*Homo sapiens* cDNA Clone Image: 2365922 3', mRNA Sequence." Strausberg, Robert (Jun. 28, 1998).
Database EMBL Accession No. AQ310967, "*Homo sapiens* Genomic Clone 2384B13, Genomic Survey Sequence." Adams, M. D. et al. (Dec. 23, 1998).
Janeway, C. A. Jr., and Travers, P., ImmunoBiology: The Immune System in Health and Disease, Current Biology Ltd/Garland Publishing Inc.; London, UK and New York, NY, USA; 1994, p. G:1.
Arrighi, I, et al., "Structure, Chromosome Localization, and Tissue Distribution of the Mouse TWIK K+ Channel Gene," FEBS Lett. 425(2):310-316 (1998).
Bonaldo, M.F., et al., "Normalization and Subtraction: Two Approaches to Facilitate Gene Discovery," Genome Res. 6(9):791-806 (1996).
Cross, S. H. et al., "Purification of CpG Islands Using a Methylated DNA Binding Column," Nat. Genet. 6(3):236-244 (1994).
DiPolo, A. et al., "Isolation and Initial Characterization of the 5' Flanking Region of the Human and Murine Cyclic Guanosine Monophosphate-Phosphodiesterase β-Subunit Genes," Invest. Ophthalmol. Vis. Sci. 37(4):551-560 (1996).
Doyle, D. A., et al., "The Structure of the Potassium Channel : Molecular Basis of K+ Conduction and Selectivity," Science 280:69-77 (1998).
Fink, M. et al., "Cloning, Functional Expression and Brain Localization of a Novel Unconventional Outward Rectifier K+ Channel," EMBO J. 15(24):6854-6862 (1996).
Fink, M. et al., "A Neuronal Two P Domain K+ Channel Stimulated by Arachidonic Acid and Polyunsaturated Fatty Acids," EMBO J. 17(12):3297-3308 (1998).
Goldstein, S. A. et al., "ORK1, a Potassium-Selective Leak Channel with Two Pore Domains Cloned from *Drosphila melanogaster* by Expression in *Saccharomyces cerevisiae*," PHAS USA 93(23):13256-13261 (1996).
Goldstein, S. A. et al., "Sequence and Function of the Two P Domain Potassium Channels: Implications of an Emerging Superfamily," J. Mol. Med. 76:13-20 (1998).
Ketchum, K. A. et al., "A New Family of Outwardly Rectifying Potassium Channel Proteins with Two Pore Domains in Tandem," Nature 376(6542):690-695 (1995).
Leonoudakis, D. et al., "An Open Rectifier Potassium Channel with Two Pore Domains in Tandem Cloned from Rat Cerebellum," J. Neuroscience 18(3):868-877 (1998).

(Continued)

*Primary Examiner*—Marianne P Allen
(74) *Attorney, Agent, or Firm*—Banner & Witcoff, Ltd.

(57) ABSTRACT

The invention provides isolated nucleic acids molecules, designated TWIK nucleic acid molecules, which encode proteins involved in potassium channel mediated activities. The invention also provides antisense nucleic acid molecules, recombinant expression vectors containing TWIK nucleic acid molecules, host cells into which the expression vectors have been introduced, and nonhuman transgenic animals in which a TWIK gene has been introduced or disrupted. The invention still further provides isolated TWIK proteins, fusion proteins, antigenic peptides and anti-TWIK antibodies. Diagnostic methods utilizing compositions of the invention are also provided.

6 Claims, 26 Drawing Sheets

OTHER PUBLICATIONS

Lesage, F. et al., "Dimerization of TWIK-1 K+ Channel Subunits Via a Disulfide Bridge," EMBO J. 15(23):6400-6407 (1996).

Lesage, F. et al., "TWIK-1, a Ubiquitous Human Weakly Inward Rectifying K+ Channel with a Novel Structure," EMBO J. 15(5):1004-1011 (1996).

Lesage, F. et al., "The Structure, Function and Distribution of the Mouse TWIK-1 K+ Channel," FEBS Lett. 402(1):28-32 (1997).

Martin-Gallardo, A. et al., "Automated DNA Sequencing and Analysis of 106 Kilobases from Human Chromosome 19q13.3," Nature Genet. 1:34-30 (1992).

Miosga, T. et al., "Sequence and Function analysis of a 9.46 kb Fragment of *Saccharomyces cerevisiae* Chromosome X," Yeast 10(7):965-973 (1994).

Pinaud, E. et al., "Identification of a Homolog of the C Alpha 3'/hs3 enhancer and of an Allelic Variant of the 3'lgH/hs1,2 Enhancer Downstream of the Human Immunoglobulin Alpha 1 Gene," Eur. J. Immunol. 27(11):2981-2985 (1997).

Reid, J. D. et al., "The *S. cerevisiae* Outwardly-Rectifying Potassium Channel (DUK1) Identifies a New Family of Channels with Duplicated Pore Domains," Recept. Channels 4(1):51-62 (1996).

Reyes, R. et al., "Cloning and Expression of a Novel pH-Sensitive Two Pore Domain K+ Channel from Human Kidney," J. Biol. Chem. 273(47):30863-30869 (1998).

Wilson, R. et al., "2.2 Mb of Contiguous Nucleotide Sequence from Chromosome III of *C. elegans*," Nature 368(6466):32-38 (1994).

Yamaguchi, M. et al., "The Primary Structure of the Rat Guanylyl A/Atrial Natriuretic Peptide Receptor Gene," J. Biol. Chem. 265(33):20414-20420 (1990).

GenBank Accession No. AA925138 for UI-R-A1-en-b-02-0-UI.s1 UI-R-A1 *Rattus norvegicus* cDNA Clone UI-R-A1-en-b-02-0-UI 3' similar to gi; 2809390; gb; AF031384 *Rattus norvegicus* TWIK-related acid Sensitive K+ channel (TASK) mRNA, complete cpds, mRNA sequence, Feb. 7, 1999.

GenBank Accession No. AAA81455 for Similar to Potassium Channel Proteins and to *C. elegans* Protein F22B7.7; Nov. 14, 1995.

GenBank Accession No. AAA83199 for Weak Similarity to a Short Region of Putative Potassium Channel Proteins; Dec. 12, 1995.

GenBank Accession No. AAA96127 for Coded for by *C. elegans* cDNA yk9g1.3; coded for by *C. elegans* cDNA yk9g1.5; coded for by *C. elegans* cDNA CEESU55F; Apr. 18, 1996.

GenBank Accession No. AAB01688 for TWIK-1, Jun. 7, 1996.

GenBank Accession No. AAB04567 for Weak Similarity to a Potassium Channel Protein, Jul. 22, 1996.

GenBank Accession No. AAB52940 for Weak Similarity to *S. cerevisiae* Outward-Rectifier Potassium Channel TOK1, Apr. 21, 1997.

GenBank Accession No. AAB54033 unidentified proten, May 12, 1997.

GenBank Accession No. AAB61602 for rabKCNK1, Jun. 18, 1997.

GenBank Accession No. AAC16973 for TWIK-1 K+ Channel, Sep. 29, 1998.

GenBank Accession No. AAC32854 for Putative Potassium Channel Subunit n2P17m1-2, Dec. 21, 1998.

GenBank Accession No. AAC32855 for Putative Potassium Channel Subunit n2P17m1-1, Dec. 21, 1998.

GenBank Accession No. AAC32856 for Putative Potassium Channel Subunit n2P16, Dec. 21, 1998.

GenBank Accession No. AAC32857 for Putative Potassium Channel Subunit n2P20, Dec. 21, 1998.

GenBank Accession No. AAC32858 for Putative Potassium Channel Subunit n2P17m2-2, Dec. 21, 1998.

GenBank Accession No. AAC32859 for Putative Potassium Channel Subunit n2P17m2-3.

GenBank Accession No. AAC32860 for Putative Potassium Channel Subunit n2P17m3, Dec. 21, 1998.

GenBank Accession No. ACC32861 for Putative Potassium Channel Subunit n2P18, Dec. 21, 1998.

GenBank Accession No. AAC32862 for Putative Potassium Channel Subunit n2P17m2-1, Dec. 21, 1998.

GenBank Accession No. AAC32863 for Putative Potassium Channel Subunit n2P38, Dec. 21, 1998.

GenBank Accession No. AAC32865 for Putative Potassium Channel Subunit n2P24, Dec. 21, 1998.

GenBank Accession No. AAC39952 for TWIK-related acid-sensitive K+ channel, Feb. 2, 1999.

GenBank Accession No. AAC40181 for TRAAK K+ channel subunit, Feb. 2, 1999.

GenBank Accession No. AAC47976 for Contains Similarity to K+ channel proteins, Feb. 26, 1998.

GenBank Accession No. AAC48050 for Similar *S. cerevisiae* Outward-Rectified Potassium channel TOK1, Jun. 2, 1999.

GenBank Accession No. AAC51777 for TWIK-related acid-sensitive K+ channel, Feb. 4, 1999.

GenBank Accession No. AAC53005 for TREK-1 K+ channel Subunit, Feb. 4, 1999.

GenBank Accession No. AAC53367 for TWIK-related acid-sensitive K+ channel, Feb. 4, 1999.

GenBank Accession No. AAC69250 for Two P domain Potassium channel ORK1, Oct. 29, 1998.

GenBank Accession No. AAC71141 for Proline-rich, Nov. 5, 1998.

GenBank Accession No. AAC71151 for Contains similarity to outward-rectified potassium channels, Nov. 5, 1998.

GenBank Accession No. AAC79458 for Two-pore domain K+ channel; TASK-2, Nov. 17, 1998.

GenBank Accession No. AAD01203 for Two-pore domain channel TPKC1, Jul. 2, 1997.

GenBank Accession No. AAD09336 for Putative potassium channel TWIK, Jan. 26, 1999.

GenBank Accession No. AAD09337 for Putative potassium channel DP3, Jan. 26, 1999.

GenBank Accession No. AAD09338 for Putative potassium channel DP4, Jan. 26, 1999.

GenBank Accession No. AB008537 for *Mus musculus* mRNA for cTBAK, complete cds, Feb. 13, 1999.

GenBank Accession No. AB013345 for *Mus musculus* mRNA for cTBAK, complete cds, May 21, 1998.

GenBank Accession No. AC005035 for *Homo sapiens* BAC clone NH0353P23 from 2, complete sequence, Dec. 3, 1998.

GenBank Accession No. AC005183 for *Homo sapiens* Chromosome 12p13.3, Aug. 21, 1998.

GenBank Accession No. AC005290 Unidentified protein, Dec. 10, 1998.

GenBank Accession No. AC005848 for *Homo sapiens* Chromosome 11 clone CIT987SK-1012F4, Oct. 22, 1998.

GenBank Accession No. AC006126 for *Homo sapiens* Chromosome 19, cosmid F18718, Dec. 17, 1998.

GenBank Accession No. AC006167 for *Homo sapiens* clone UWGC:Y67c092 from 6p21, Dec. 8, 1998.

GenBank Accession No. AF004695 for *Oryctolagus cuniculus* double-pore potassium channel rabKCNK1 mRNA, Jun. 25, 1997.

GenBank Accession No. AF006824 for *Mus musculus* TWIK-related acid-sensitive K+ channel (TASK) mRNA, Oct. 7, 1997.

GenBank Accession No. AF022821 for *Mus musculus* putative potassium channel DP4 mRNA, Jan. 26, 1999.

GenBank Accession No. AF033017 for *Mus musculus* TWIK-1 K+ channel mRNA, May 23, 1998.

GenBank Accession No. AF056492 for *Mus musculus* TRAAK K+ channel subunit mRNA, Jul. 21, 1998.

GenBank Accession No. AF084830 for *Homo sapiens* two pore domain K+ channel (TASK02) mRNA, Nov. 25, 1998.

GenBank Accession No. OMJ001356 for *Orchis morio* (Orchidaceae) microsatellite, Sep. 16, 1997.

GenBank Accession No. AQ240175 for CIT-HSP-2385B13.TR.1 CIT-HSP *Homo sapiens* genomic clone 2385B13, Sep. 29, 1998.

GenBank Accession No. AQ319946 for RPCI11-111L8.TJ RPCI-11 *Homo sapiens* genomic clone RPCI-11-111L8, May 5, 1999.
GenBank Accession No. B82804 for RPCI11-17N16.TP RPCI-11 *Homo sapiens* genomic clone RPCI-11-17N16, Apr. 8, 1999.
GenBank Accession No. BAA25436 for cTBAK, Feb. 13, 1999.
GenBank Accession No. CAA19494 for Similar to potassium channel protein, Dec. 18, 1998.
GenBank Accession No. CAA21041 for cDNA EST yk449e10.5 comes from this gene; cDNA EST EMBL: D35319 comes from this gene; cDNA EST EMBL: c12322 comes from this gene; cDNA EST EMBL: D32633 comes from this gene, Nov. 23, 1998.
GenBank Accession No. CAA21749 for Predicted using Genefinder; cDNA EST EMBL: Z14528 comes from this gene, Nov. 23, 1998.
GenBank Accession No. CAA64176 for Outward-rectifier potassium channel, Feb. 23, 1996.
GenBank Accession No. CAA84797 for Weak similarity with *Drosophila melanogaster* potassium channel proteins, Nov. 21, 1998.
GenBank Accession No. CAA90066 for Weak similarity to a protein domain (segment H5) thought to line the channel pore of potassium channels; cDNA EST EMBL: T00465 comes from this gene; cDNA EST EMBL: D36509 comes from this gene, Nov. 23, 1998.
GenBank Accession No. CAA90259 for M110.2, Nov. 23, 1998.
GenBank Accession No. CAA91376 for Similarity to potassium channel protein; cDNA EST EMBL: D70075 comes from this gene; cDNA EST EMBL: D66354 comes from this gene, Nov. 23, 1998.
GeneBank Accession No. CAA92504 for Similarity to *Drosophila* potassium channel protein (PIR Acc. No. JH0697); cDNA EST EMBL: M89234 comes from this gene; Dec. 14, 1998.
GenBank Accession No. CAA92568 for Similarity to *Drosophila* potassium channel protein (PIR Acc. No. JH0697); cDNA EST EMBL: D27674 comes from this gene; cDNA EST EMBL: D27673 comes from this gene; cDNA EST EMBL: D32607 comes from this gene; cDNA EST EMBL: D35287 comes from this gene; cDNA EST EMBL: D64971 comes from this gene; cDNA EST EMBL: D68246 comes from this gene, Nov. 23, 1998.
GenBank Accession No. CAA93875 for Similarity to yeast potassium channel protein; Nov. 23, 1998.
GenBank Accession No. CAA93881 for Similarity to potassium channel proteins, Nov. 23, 1998.
GenBank Accession No. CAA94204 for Predicted using Genefinder; Similarity to yeast potassium channel protein TOK1; Nov. 23, 1998.
GenBank Accession No. CAA95801 for Predicted using Genefinder; weak similarity to yeast potassium channel protein TOK1; Nov. 23, 1998.
GenBank Accession No. CAA98271 for Similar to potassium channel protein like; Dec. 18, 1998.
GenBank Accession No. CAA98957 for Predicted using Genefinder; Similarity to potassium channel protein, Nov. 23, 1998.
GenBank Accession No. CAA99871 for Similar to potassium channel protein; Nov. 23, 1998.
GenBank Accession No. CAB01238 Predicted using Genefinder; similarity to worm potassium channel proteins; Nov. 23, 1998.
GenBank Accession No. CAB01740 for Similar to potassium channel protein; Nov. 23, 1998.
GenBank Accession No. CAB02119 for Similar to potassium channel protein like; Nov. 23, 1998.
GenBank Accession No. CAB03071 Predicted using Genefinder; similarity to potassium channel proteins; Nov. 23, 1998.
GenBank Accession No. CAB03109 Similar to potassium channel protein; Nov. 23, 1998.
GenBank Accession No. CAB03914 for C24H11.8, Nov. 23, 1998.
GenBank Accession No. CAB04251 for cDNA EST yk240f2.5 comes from this gene; cDNA EST yk354h3.5 comes from this gene; cDNA EST yk354h3.3 comes from this gene; cDNA EST yk240f2.3 comes from this gene, Nov. 23, 1998.
GenBank Accession No. CAB04923 for cDNA EST EMBL: D66510 comes from this gene; cDNA EST EMBL: D70321 comes from this gene, Nov. 23, 1998.
GenBank Accession No. CAB04926 for cDNA EST yk224a2.3 comes from this gene; cDNA EST yk224a2.5 comes from this gene, Nov. 23, 1998.
GenBank Accession No. CAB05769 Similar to potassium channel protein; Nov. 23, 1998.
GenBank Accession No. CAB07286 for T28A8.1, Nov. 23, 1998.
GenBank Accession No. CAB07375 for F31D4.7, Nov. 23, 1998.
GenBank Accession No. CAB07854 for R12G8.2, Nov. 23, 1998.
GenBank Accession No. J05677 for RAT guanylyl cyclase A/atrial natriuretic peptide receptor (GC-A) gene, Jan. 15, 1991.
GenBank Accession No. L17688 for Human STS UT5089, May 28, 1993.
GenBank Accession No. M63796 for Human DNA from cosmid MMDA from Chromosome 19q13.3, Apr. 9, 1992.
GenBank Accession No. P34410 for TWK-8 protein, Jul. 15, 1998.
GenBank Accession No. P40310 for Outward-rectifier potassium channel TOK1 (Two-domain outward rectifier K+ channel York), Nov. 1, 1997.
GenBank Accession No. U31663 for *Mus musculus* Chromosome 2 marker um-m12 TC dinucleotide 2 DNA sequence, Aug. 30, 1995.
GenBank Accession No. U31761 for *Mus musculus* cGMP-phosphodiesterase beta-subunit gene, May 21, 1996.
GenBank Accession No. U.33632 for Human two P-domain K+ channel TWIK-1 mRNA, Jun. 5, 1996.
GenBank Accession No. U55321 for *Drosophila melanogaster* two P domain potassium channel ORK1 (ORK1) mRNA, Oct. 29, 1998.
GenBank Accession No. U73488 for *Mus musculus* TREK-1 K+ channel subunit mRNA, Jan. 25, 1997.
GenBank Accession No. U76996 for *Homo sapiens* two P domain channel subunit (HOHO1) mRNA, Jan. 29, 1998.
GenBank Accession No. U90065 for Human potassium channel KCNO1 mRNA, Apr. 1, 1997.
GenBank Accession No. Y14406 for *Homo sapiens* DNA for 3' IgH locus control region, HS3 enhancer, Feb. 12, 1998.
GenBank Accession No. Z55211 for *Homo sapiens* CpG island DNA genomic Mse1 fragment, clone 26g4, Forward Read CPG26G4. FT1B, Oct. 17, 1995.
GenBank Accession No. Z75539 for *Caenorhabditis elegans* cosmid F28C1, Dec. 14, 1998.
GenBank Accession No. AC005661 for citb_54_o_2, DNA; Nov. 30, 1999.
GenBank Accession No. AC005880 for citb_43_a_11, DNA; Nov. 5, 1999.
GenBank Accession No. Z78198 for *Caenorhabditis elegans* cosmid F55C5, DNA; Jan. 26, 2000.
GenBank Accession No. Z81475 for *Caenorhabditis elegans* cosmid C24H11, DNA; Dec. 14, 1999.
GenBank Accession No. Z92813 for *Caenorhabditis elegans* cosmid T28A8, DNA; Dec. 14, 1999.

* cited by examiner

TWIK 2

Input file FthKa020g04.seq; Output File FthKa020g04.tra
Sequence length 3452

```
                     M   V   D   R   G   P   L   L   T   S   A   I   I   F   Y   L   A
TCGGGAGCC ATG GTG GAC CGG GGC CCT CTG CTC ACC TCG GCC ATC ATC TTC TAC CTG GCC
      I   G   A   A   I   F   E   V   L   E   E   P   H   W   K   E   A   K   K   N
ATC GGG GCG GCG ATC TTC GAA GTG CTG GAG GAG CCA CAC TGG AAG GAG GCC AAG AAA AAC
      Y   Y   T   Q   K   L   H   L   L   K   E   F   P   C   L   G   Q   E   G   L
TAC TAC ACA CAG AAG CTG CAT CTG CTC AAG GAG TTC CCG TGC CTG GGT CAG GAG GGC CTG
      D   K   I   L   E   V   V   S   D   A   A   G   Q   G   V   A   I   T   G   N
GAC AAG ATC CTA GAG GTG GTA TCT GAT GCT GCA GGA CAG GGT GTG GCC ATC ACA GGG AAC
      Q   T   F   N   N   W   N   W   P   N   A   M   I   F   A   A   T   V   I   T
CAG ACC TTC AAC AAC TGG AAC TGG CCC AAT GCA ATG ATT TTT GCA GCG ACC GTC ATT ACC
      T   I   G   Y   G   N   V   A   P   K   T   P   A   G   R   L   F   C   V   F
ACC ATT GGA TAT GGC AAT GTG GCT CCC AAG ACC CCC GCC GGT CGC CTC TTC TGT GTT TTC
      Y   G   L   F   G   V   P   L   C   L   T   W   I   S   A   L   G   K   F   F
TAT GGT CTC TTC GGG GTG CCG CTC TGC CTG ACG TGG ATC AGT GCC CTG GGC AAG TTC TTC
      G   G   R   A   K   R   L   G   Q   F   L   T   K   R   G   V   S   L   R   K
GGG GGA CGT GCC AAG AGA CTA GGG CAG TTC CTT ACC AAG AGA GGT GTG AGT CTG CGG AAG
      A   Q   I   T   C   T   V   I   F   I   V   W   G   V   L   V   H   L   V   I
GCG CAG ATC ACG TGC ACA GTC ATC TTC ATC GTG TGG GGC GTC CTA GTC CAC CTG GTG ATC
      P   P   F   V   F   M   V   T   E   G   W   N   Y   I   E   G   L   Y   Y   S
CCA CCC TTC GTA TTC ATG GTG ACT GAG GGG TGG AAC TAC ATC GAG GGC CTC TAC TAC TCC
      F   I   T   I   S   T   I   G   F   G   D   F   V   A   G   V   N   P   S   A
TTC ATC ACC ATC TCC ACC ATC GGC TTC GGT GAC TTT GTG GCC GGT GTG AAC CCC AGC GCC
      N   Y   H   A   L   Y   R   Y   F   V   E   L   W   I   Y   L   G   L   A   W
AAC TAC CAC GCC CTG TAC CGC TAC TTC GTG GAG CTC TGG ATC TAC TTG GGG CTG GCC TGG
      L   S   L   F   V   N   W   K   V   S   M   F   V   E   V   H   K   A   I   K
CTG TCC CTT TTT GTC AAC TGG AAG GTG AGC ATG TTT GTG GAA GTC CAC AAA GCC ATT AAG
      K   R   R   R   R   K   E   S   F   E   S   S   P   H   S   R   K   A   L
AAG CGG CGG CGG CGA CGG AAG GAG TCC TTT GAG AGC TCC CCA CAC TCC CGG AAG GCC CTG
      Q   V   K   G   S   T   A   S   K   D   V   N   I   F   S   F   L   S   K   K
CAG GTG AAG GGG AGC ACA GCC TCC AAG GAC GTC AAC ATC TTC AGC TTT CTT TCC AAG AAG
      E   E   T   Y   N   D   L   I   K   Q   I   G   K   K   A   M   K   T   S   G
GAA GAG ACC TAC AAC GAC CTC ATC AAG CAG ATC GGG AAG AAG GCC ATG AAG ACA AGC GGG
      G   G   E   T   G   P   G   P   G   L   G   P   Q   G   G   L   P   A   L
GGT GGG GAG ACG GGC CCG GGC CCA GGG CTG GGG CCT CAA GGC GGT GGG CTC CCA GCA CTG
      P   P   S   L   V   P   L   V   V   Y   S   K   N   R   V   P   T   L   E   E
CCC CCT TCC CTG GTG CCC CTG GTA GTC TAC TCC AAG AAC CGG GTG CCC ACC TTG GAA GAG
      V   S   Q   T   L   R   S   K   G   H   V   S   R   S   P   D   E   E   A   V
GTG TCA CAG ACA CTG AGG AGC AAA GGC CAC GTA TCA AGG TCC CCA GAT GAG GAG GCT GTG
      A   R   A   P   E   D   S   S   P   A   P   E   V   F   M   N   Q   L   D   R
GCA CGG GCC CCT GAA GAC AGC TCC CCT GCC CCC GAG GTG TTC ATG AAC CAG CTG GAC CGC
      I   S   E   E   C   E   P   W   D   A   Q   D   Y   H   P   L   I   F   Q   D
ATC AGC GAG GAA TGC GAG CCA TGG GAC GCC CAG GAC TAC CAC CCA CTC ATC TTC CAG GAC
      A   S   I   T   F   V   N   T   E   A   G   L   S   D   E   E   T   S   K   S
GCC AGC ATC ACC TTC GTG AAC ACG GAG GCT GGC CTC TCA GAC GAG GAG ACC TCC AAG TCC
      S   L   E   D   N   L   A   G   E   E   S   P   Q   Q   G   A   E   A   K   A
TCG CTA GAG GAC AAC TTG GCA GGG GAG GAG AGC CCC CAG CAG GGG GCT GAA GCC AAG GCG
```

Fig. 1

```
P   L   N   M   G   E   F   P   S   S   S   E   S   T   F   T   S   T   E   S
CCC CTG AAC ATG GGC GAG TTC CCC TCC TCC TCC GAG TCC ACC TTC ACC AGC ACT GAG TCT
E   L   S   V   P   Y   E   Q   L   M   N   E   Y   N   K   A   N   S   P   K
GAG CTC TCT GTG CCT TAC GAA CAG CTG ATG AAT GAG TAC AAC AAG GCT AAC AGC CCC AAG
G   T   *
GGC ACA TGA
```

GGCAGGGCCGGCTCCCCACCCCACCTTTGATGGCCTCTTCCCCCCTCACCCTAGGGTGTCCCAAGATGACCGGGACGCC

TGGCCCCTGGTGGGGGGGCAGCCTCGGAACTGGGAGTGGGGGGCCAGGGGCCTTCCTAACCTTCCATCATCCTCAGCTA

GATGTATGCCCGGGACAGGGCCTCTGTTCTCCAGCTGAACCATACCCTGGCTGTGGGGGCATCTGTCCTGAGCTTGGCT

GGTGTATCTCACAATGCAAAGACATGCTGGCTGGCGGGACAGGTGGGCAGGACTGACCCTGAGGAGGCCTTGCCTGCAG

GGTCTTTGTCTCACCATTTGGTGGAGTATCACACGGTTCTCTGAGGTCTGGGGCCTCAGCTGTTTAAGTTTACCGGTAT

TACTGAGCTCGGCATTTGGAGAGGGAGCTCTGAAGTGTCTGGGGAGGTACCGCTGTGCGTGGGGTCAGGTGTTTCCGTA

CCACAGCAGGAGCAGGGCCTGCCCGCATCCCAGCTGTGGGCCTGCCGGTCAGGTCGGGCACCTACTACAAACCGTAGTG

GGGTGGAGGCTGCTGGAGGTGGGAGTGAGGAGATGAGGGCAGGGTCTCAAACAGTCCTGACTCACAGGGCCTGGAAACA

AGTCCTATGTGGGCCTGGGGCCTGGGGTCCTCATCCTCCTTGTTGGTCTACTCAGGCCCAGCCCAGAGCTGTGTTCCCT

GTCTCAGGTCAAGCAGTGGCAGACGCAAGGCTTTCTGTGGGCCCCCAAGTGGTAGGAGGGAGAGTAGCAGAGCATGGGT

TACTGGAAGCCGGGACTGCTAGGGCTGGTGGCCAGGGAGCTGCAAGAGTGAGGCTCAGCTCTGGCTGGTTCTGCCCTTA

CCCCTCCTGCCCGCCTGAGAACTGCACACCCTGCCCGCTGGCCCCAGGACCTGCACTCCCAATCCTGCTGTCTTCTCCT

TCCCTGTGCCCTGAACAAGGACCTCACTGCCCGCCTTCCCCTCCCACCAGCCCCCTTGGGCCAGGCAGGGTGAGGCCAA

ATTGCTCTTGGCCCACAAATGGGTGATGGTCAGATATGTGAATCAAGCTCCTTTCTCTAGCTAGTGTTTGATGTGCACG

TGTGTGTGCACAGTGCGTGTGTGCACACGCACACCTGTGCACTCGTGTGTGTTTAAGAAAGGAAAGGATTTGGGCTGGG

GAGCAAAAGATAATGTGAAACTGTTGGTGGACTCTCTGGTGAGGGGTGGGCAGAACTTGCTGCTACTAGAGTTCTTGGG

TTCTCCATGATGTTCACCCTGGGGCTGGCCCACTGTGTCCTGAATGTTTTTGTTATTTTTGTTTTATTTTTAAACAA

ACTGCTGTTTTTATATACCTGGAATCTGTTGTTGGCTTCAGAGCCAGTGGTTAAAGAGCAGGGTCCCAAGGATTGGGAG

ATCTAGTGTCTGCCCTCCTGCCCTGCAACTCAATTGGGCCTTTTTCGGTGACCTCATCCAAGGCCATGATGTCAAGGGC

CATGTCCCCAAGCAGAGGTGGAGAAGGGGACACTGAGGTGAGCAAAAGCAGGAAGGGGCATCCACTGCGGGTGACTGGA

Fig. 1 (continued)

Input file Athua133f10.seq; Output File Athua133f10.tra
Sequence length 1575

```
CAACGCGTCCGCCGGGCACCAGCAGGCGTTTGCGAGAGGAGATACGAGCTGGACGCCTGGCCCTTCCCTCCCACCGGGT
                                                         M   Y   R   P   R   A   R   A   A
CCTAGTCCACCGCTCCCGGCGCCGGCTCCCCGCTCTCCCGCT ATG TAC CGA CCG CGA GCC CGG GCG GCT
 P   E   G   R   V   R   G   C   A   V   P   G   T   V   L   L   L   A   Y
CCC GAG GGC AGG GTC CGG GGC TGC GCG GTG CCC GGC ACC GTG CTC CTG CTG CTC GCC TAC
 L   A   Y   L   A   L   G   T   G   V   F   W   T   L   E   G   R   A   A   Q
CTG GCT TAC CTG GCG CTG GGC ACC GGC GTG TTC TGG ACG CTG GAG GGC CGC GCG GCG CAG
 D   S   S   R   S   F   Q   R   D   K   W   E   L   L   Q   N   F   T   C   L
GAC TCC AGC CGC AGC TTC CAG CGC GAC AAG TGG GAG CTG TTG CAG AAC TTC ACG TGT CTG
 D   R   P   A   L   D   S   L   I   R   D   V   V   Q   A   Y   K   N   G   A
GAC CGC CCG GCG CTG GAC TCG CTG ATC CGG GAT GTC GTC CAA GCA TAC AAA AAC GGA GCC
 S   L   L   S   N   T   T   S   M   G   R   W   E   L   V   G   S   F   F   F
AGC CTC CTC AGC AAC ACC ACC AGC ATG GGG CGC TGG GAG CTC GTG GGC TCC TTC TTC TTT
 S   V   S   T   I   T   T   I   G   Y   G   N   L   S   P   N   T   M   A   A
TCT GTG TCC ACC ATC ACC ACC ATT GGC TAT GGC AAC CTG AGC CCC AAC ACG ATG GCT GCC
 R   L   F   C   I   F   F   A   L   V   G   I   P   L   N   L   V   V   L   N
CGC CTC TTC TGC ATC TTC TTT GCC CTT GTG GGG ATC CCA CTC AAC CTC GTG GTG CTC AAC
 R   L   G   H   L   M   Q   Q   G   V   N   H   W   A   S   R   L   G   G   T
CGA CTG GGG CAT CTC ATG CAG CAG GGA GTA AAC CAC TGG GCC AGC AGG CTG GGG GGC ACC
 W   Q   D   P   D   K   A   R   W   L   A   G   S   G   A   L   L   S   G   L
TGG CAG GAT CCT GAC AAG GCG CGG TGG CTG GCG GGC TCT GGC GCC CTC CTC TCG GGC CTC
 L   L   F   L   L   L   P   P   L   F   S   H   M   E   G   W   S   Y   T
CTG CTC TTC CTG CTG CTG CCA CCG CTG CTC TTC TCC CAC ATG GAG GGC TGG AGC TAC ACA
 E   G   F   Y   F   A   F   I   T   L   S   T   V   G   F   G   D   Y   V   I
GAG GGC TTC TAC TTC GCC TTC ATC ACC CTC AGC ACC GTG GGC TTC GGC GAC TAC GTG ATT
 G   M   N   P   S   Q   R   Y   P   L   W   Y   K   N   M   V   S   L   W   I
GGA ATG AAC CCC TCC CAG AGG TAC CCA CTG TGG TAC AAG AAC ATG GTG TCC CTG TGG ATC
 L   F   G   M   A   W   L   A   L   I   I   K   L   I   L   S   Q   L   E   T
CTC TTT GGG ATG GCA TGG CTG GCC TTG ATC ATC AAA CTC ATC CTC TCC CAG CTG GAG ACG
 P   G   R   V   C   S   C   C   H   H   S   S   K   E   D   F   K   S   Q   S
CCA GGG AGG GTA TGT TCC TGC TGC CAC CAC AGC TCT AAG GAA GAC TTC AAG TCC CAA AGC
 W   R   Q   G   P   D   R   E   P   E   S   H   S   P   Q   Q   G   C   Y   P
TGG AGA CAG GGA CCT GAC CGG GAG CCA GAG TCC CAC TCC CCA CAG CAA GGA TGC TAT CCA
 E   G   P   M   G   I   I   Q   H   L   E   P   S   A   H   A   A   G   C   G
GAG GGA CCC ATG GGA ATC ATA CAG CAT CTG GAA CCT TCT GCT CAC GCT GCA GGC TGT GGC
 K   D   S   *
AAG GAC AGC TAG
TTATACTCCATTCTTTGGTCGTCGTCCTCGGTAGCAAGACCCCTGATTTTAAGCTTTGCACATGTCCACCCAAACTAAA
GACTACATTTTCCATCCACCCTAGAGGCTGGGTGCAGCTATATGATTAATTCTGCCCAATAGGGTATACAGAGACATGT
CCTGGGTGACATGGGATGTGACTTTCGGGTGTCGGGCAGCATGCCCTTCTCCCCCACTTCCTTACTTTAGCGGGCTGC
AATGCCGCCGATATGATGGCTGGGAGCTCTGGCAGCCATACGGCACCATGAAGTAGCGGCAATGTTTGAGCGGCACAAT
AAGATAGGAAGAGTCTGGATCTCTGATGATCACAGAGCCATCCTAACAAACGGAATATCACCCGACCTCCTTTATGTGA
GAGAGAAATAAACATCTTATGTAAAATACAAAAAAAAAAAAAAAAAAAAAAAGGGCGGCCGC
```

Fig. 3

TWIK 4
Input file AthTb005e07.seq; Output File AthTb005e07.tra
Sequence length 2287

TAAAAGCTGCGGAATTCTAATATCACTCACTATAGGGAGTCGACCCACGCGTCCGGGAACTAGGTGCCAGACGGTCCGG
                                                                M   R   R   G   A
AGGCGGGGGCCACGTCAGCGGGGCCACCCAGGGCTCGCGGGGTCCCGGTGGGTGCC ATG CGG AGG GGC GCG
 L   L   A   G   A   L   A   A   Y   A   A   Y   L   V   L   G   A   L   L   V
CTT CTG GCG GGC GCC TTG GCC GCG TAC GCC GCG TAC CTG GTG CTG GGC GCG CTG TTG GTG
 A   R   L   E   G   P   H   E   A   R   L   R   A   E   L   E   T   L   R   A
GCG CGG CTG GAG GGG CCG CAC GAA GCC AGG CTC CGA GCC GAG CTG GAG ACG CTG CGG GCG
 Q   L   L   Q   R   S   P   C   V   A   A   P   A   L   D   A   F   V   E   R
CAG CTG CTT CAG CGC AGC CCG TGT GTG GCT GCC CCC GCC CTG GAC GCC TTC GTG GAG CGA
 V   L   A   A   G   R   L   G   R   V   V   L   A   N   A   S   G   S   A   N
GTG CTG GCG GCC GGA CGG CTG GGG CGG GTC GTG CTT GCT AAC GCT TCG GGG TCC GCC AAC
 A   S   D   P   A   W   D   F   A   S   A   L   F   F   A   S   T   L   I   T
GCC TCG GAC CCC GCC TGG GAC TTC GCC TCT GCT CTC TTC TTC GCC AGC ACG CTG ATC ACC
 T   V   G   Y   G   Y   T   T   P   L   T   D   A   G   K   A   F   S   I   A
ACC GTG GGC TAT GGG TAC ACA ACG CCA CTG ACT GAT GCG GGC AAG GCC TTC TCC ATC GCC
 F   A   L   L   G   V   P   T   T   M   L   L   T   A   S   A   Q   R   L
TTT GCG CTC CTG GGC GTG CCG ACC ACC ATG CTG CTG CTG ACC GCC TCA GCC CAG CGC CTG
 S   L   L   T   H   V   P   L   S   W   L   S   M   R   W   G   W   D   P
TCA CTG CTG CTG ACT CAC GTG CCC CTG TCT TGG CTG AGC ATG CGT TGG GGC TGG GAC CCC
 R   R   A   A   C   W   H   L   V   A   L   L   G   V   V   V   T   V   C   F
CGG CGG GCG GCC TGC TGG CAC TTG GTG GCC CTG TTG GGG GTC GTA GTG ACC GTC TGC TTT
 L   V   P   A   V   I   F   A   H   L   E   E   A   W   S   F   L   D   A   F
CTG GTG CCG GCT GTG ATC TTT GCC CAC CTC GAG GAG GCC TGG AGC TTC TTG GAT GCC TTC
 Y   F   C   F   I   S   L   S   T   I   G   L   G   D   Y   V   P   G   E   A
TAC TTC TGC TTT ATC TCT CTG TCC ACC ATC GGC CTG GGC GAC TAC GTG CCC GGG GAG GCC
 P   G   Q   P   Y   R   A   L   Y   K   V   L   V   T   V   Y   L   F   L   G
CCT GGC CAG CCC TAC CGG GCC CTC TAC AAG GTG CTG GTC ACA GTC TAC CTC TTC CTG GGC
 L   V   A   M   V   L   V   L   Q   T   F   R   H   V   S   D   L   H   G   L
CTG GTG GCC ATG GTG CTG GTG CTG CAG ACC TTC CGC CAC GTG TCC GAC CTC CAC GGC CTC
 T   E   L   I   L   L   P   P   P   C   P   A   S   F   N   A   D   E   D   D
ACG GAG CTC ATC CTG CTG CCC CCT CCG TGC CCT GCC AGT TTC AAT GCG GAT GAG GAC GAT
 R   V   D   I   L   G   P   Q   P   E   S   H   Q   Q   L   S   A   S   S   H
CGG GTG GAC ATC CTG GGC CCC CAG CCG GAG TCG CAC CAG CAA CTC TCT GCC AGC TCC CAC
 T   D   Y   A   S   I   P   R
ACC GAC TAC GCT TCC ATC CCC AGG
TAGCTGGGGCAGCCTCTGCCAGGCTTGGGTGTGCCTGGCCTGGGACTGAGGGGTCCAGGCGACCAGAGCTGGCTGTACA
GGAATGTCCACGAGCACAGCAGGTGATCTTGAGGCCTTGCCGTCCACCGTCTCTCCTTTGTTTCCCAGCATCTGGCTGG
GATGTGAAGGGCAGCACTCCCTGTCCCCATGTCCCGGGCTCCACTGGGCACCAACATAACCTTGTTCTCTGTCCTTTCT

Fig. 5

```
CTCATCCTCTTTACACTGTGTCTCTCTGGCTCTCTGGCATTCTCGCTGCCTCTGTCTTTCCCTCTTGCTGTCTCTGGTT
CTCATTCTCTTTCATGTTCCGKCTGKGTCTCTCAATTAACCACTCGTCAACTGCTGATTCTACTGGGCTGTGGGCTCAG
ACCTCATTTCAGGCACCAGATTGGTCGCTACACCCTGGACAAGTGACTGCCCGTCTCTGAGCCTTGATTTCCTCAGCTG
CCAAATGGGAAGAATAGAAGAATTTGCCCCTAAACCCCTCCTGTGTGCTGGCCCTGTGCTAGACAGTGCTGGAGACATA
GTTGGGGGTGGAGAACTGCCCTTATGGAGCTTGCAGTCCAGTGAGGTGGACAGACCTGTCCCCAGACAGTGATGGCCCA
AAATGGTCAGGACTTTAATGGAGGARGTGAAGGTGTTGAAAGCACAGGCAGAGTGGGTCAGGKCTTGAAGTCGKAGAAG
CATARGGGVCTAGGCCCAATCCANGCCTGGAAAAGTMMGGGAGNGACNTTCCTAGAGGAACGGGACATCGAACTAAAGA
CCTGAANCTATGAGAAATAGGCAGGAAGAAGTTGTACCNTGACTCATTTTTTTCAGGTGTCTCCAGGGAGCAGGACCCA
TGGAGGGACCCCTGGTGTAGGCHTGGCCAGATAGACTCTTCACTCAGCAGCCTGGCAGGCAGGAARCAGWCATAGGMCC
CCAGCCCAGATYTGAATGGCMYSGGAGGTGCTGCCCTTWCCCRTGACACCATTGWAAGWGCTGYCCACATWTGTATGKT
GTGCCCTGGAANTCAGCCAGGTTGAGCTCAAATCCCAACTTAGCCASGTCTGGCCTGTGTCCTTGGGCAGTCACACTAC
CTCTCTGATTTTGTTTCMWWAATCATGTAAAATGGTGATCATCATAATACAACTTCAAAAGGAAAAAAAAAAAAAAAAA
AAAAAAAAAGGGCGGCCGCTAGACTAGT
```

Fig. 5 (continued)

Clustal W (1.74) multiple sequence alignment

```
AthTb005e07    ------------------------MRRGALLAGALAA----------------YAAYLVL
hTWIK-1        --------MLQSLAGSSCVRLVERHRSAWCFGFLVLG-----------------YLLYLVF
mTRAAK         ---------------------MRSTTLLALLAL--------------------VLLYLVS
mTREK-1        MAAPDLLDPKSAAQNSKPRLSFSSKPTVLASRVESDSAINVMKWKTVSTIFLVVVLYLII
Athua133f10    -------MYRPRARAAPEGRVRGCAVPGTVLLLLAY-----------------LAYLAL
FthKa20g4      ------------------MVDRGPLLTSAIIF---------------------YLAI
hTASK          ---------------------MKRQNVRTLALIVC------------------TFTYLLV
                                                                        :       **

AthTb005e07    GALLVARLEGPHEARLRAELETLRAQLLQRSPCVAAPALDAFVERVLAAGRLGRVVLANA
hTWIK-1        GAVVFSSVELPYEDLLRQELRKLKRRFLEEHECLSEQQLEQFLGRVLEASNYGVSVLSNA
mTRAAK         GALVFQALEQPHEQQAQKKMDHGRDQFLRDHPCVSQKSLEDFIKLLVEALGGGANPETSW
mTREK-1        GAAVFKALEQPQEISQRTTIVIQKQTFIAQHACVNSTELDELIQQIVAAINAGIIPLGNS
Athua133f10    GTGVFWTLEGRAAQDSSRSFQRDKWELLQNFTCLDRPALDSLIRDVVQAYKNGASLLSNT
FthKa20g4      GAAIFEVLEEPHWKEAKKNYYTQKLHLLKEFPCLGQEGLDKILEVVSDAAGQGVAITGNQ
hTASK          GAAVFDALESEPELIERQRLRLR-QQELRARYNLSQGGYEELERVVLRLKPHKAG--VQ-
               *:  :.   :*                      :      :    :   :      .

AthTb005e07    SGSANASDPAWDFASALFFASTLITTVGYGYTTPLTDAGKAFSIAFALLGVPTTMLLLTA
hTWIK-1        SGNWN-----WDFTSALFFASTVLSTTGYGHTVPLSDGGKAFCIIYSVIGIPFTLLFLTA
mTRAAK         TNSSNHSS-AWNLGSAFFFSGTIITTIGYGNIVLHTDAGRLFCIFYALVGIPLFGMLLAG
mTREK-1        SNQVSH----WDLGSSFFFAGTVITTIGFGNISPRTEGGKIFCIIYALLGIPLFGFLLAG
Athua133f10    TSMGR-----WELVGSFFFSVSTITTIGYGNLSPNTMAARLFCIFFALVGIPLNLVVLNR
FthKa20g4      TFN-N-----WNWPNAMIFAATVITTIGYGNVAPKTPAGRLFCVFYGLFGVPLCLTWISA
hTASK          ---------WRFAGSFYFAITVITTIGYGHAAPSTDGGKVFCMFYALLGIPLTLVMFQS
                         *  .::  *:  :  ::*  *:*     : ..:  *.: :.:.*:*    :

AthTb005e07    SAQRLSLLLTH--VPLSWLSMRWGWDPRRAACWHLVALLGVVVTVCFLVPAVIFAHLEEA
hTWIK-1        VVQRITVHVTR--RPVLYFHIRWGFSKQVVAIVHAVLLGFVTVSCFFFIPAAVFSVLEDD
mTRAAK         VGDRLGSSLRRGIGHIEAIFLKWHVPPGLVRSLSAVLFLLIGCLLFVLTPTFVFSYMES-
mTREK-1        VGDQLGTIFGKGIAKVEDTFIKWNVSQTKIRIISTIIFILFGCVLFVALPAVIFKHIEG-
Athua133f10    LGHLMQQGVNH---WASRLGGTWQD-PDKARWLAGSGALLSGLLLFLLLPPLLFSHMEG-
FthKa20g4      LGKFFGGRAKR----LGQFLTKRGVSLRKAQITCTVIFIVWGVLVHLVIPPFVFMVTEG-
hTASK          LGERINTLVRY---LLHRAKKGLGMRRADVSMANMVLIGFFSCISTLCIGAAAFSHYEH-
               .  :                                            .  . *  *

AthTb005e07    WSFLDAFYFCFISLSTIGLGDYVPGEAPGQ-----PYRALYKVLVTVYLFLGLVAMVLVL
hTWIK-1        WNFLESFYFCFISLSTIGLGDYVPGEGYNQ-----KFRELYKIGITCYLLLGLIAMLVVL
mTRAAK         WSKLEAIYFVIVTLTTVGFGDYVPGDGTGQNS-P-AYQPLVWFWILFGLAYFASVLTTIG
mTREK-1        WSALDAIYFVVITLTTIGFGDYVAGGSDIEYL-D-FYKPVVWFWILVGLAYFAAVLSMIG
Athua133f10    WSYTEGFYFAFITLSTVGFGDYVIGMNPSQRYPL-WYKNMVSLWILFGMAWLALIIKLIL
FthKa20g4      WNYIEGLYYSFITISTIGFGDFVAGVNPSANYHA-LYRYFVELWIYLGLAWLSLFVNWKV
hTASK          WTFFQAYYYCFITLTTIGFGDYVALQKDQALQTQPQYVAFSFVYILTGLTVIGAFLNLVV
               *.   :.  *:  .:::::*:*:**:*                 :  . : :    :

AthTb005e07    QTFRHVSDLHGLTELILLPPP----------------------------
hTWIK-1        ETFCELHELKKFRKMFYVKKDK----------------------------
mTRAAK         NWLRAVSRRTRAEMGGLTAQAA----------------------------
mTREK-1        DWLRVISKKTKEEVGEFRAHAA----------------------------
Athua133f10    SQLETPGRVCSCCHHSSKEDFK----------------------------
FthKa20g4      SMFVEVHKAIKKRRRRRKESFESSPHSRKALQVKGSTASKDVNIFSFLSKKEETYNDLIK
hTASK          LRFMTMNAEDEKRDAEHRALLTRN--------------------------
               :
```

Fig. 7

```
AthTb005e07    ------------------------------------CPASFNADEDDRV--------
hTWIK-1        ------------------------------------DEDQVHIIEHDQLSFSSIT--
mTRAAK         ------------------------------------SWTGTVTARVTQR-----T--
mTREK-1        ------------------------------------EWTANVTAEFKETR----R--
Athual33f10    ------------------------------------SQSWRQGPDREPES---HS--
FthKa20g4      QIGKKAMKTSGGGETGPGPGLGPQGGGLPALPPSLVPLVVYSKNRVPTLEEVSQTLRSKG
hTASK          ------------------------------------GQAGGGGGGGSAHTTDTAS--

AthTb005e07    -DILGPQPESHQQ---LSASSHTDYASIPR------------------------------
hTWIK-1        -DQAAGMKEDQKQNEPFVATQSSACVDGPANH----------------------------
mTRAAK         -GPSAPPPEKEQPLLPSSLPAPPAVVEPAGRPGSPA-PAEKVETPSPPTA-SALDYPSEN
mTREK-1        -RLSVEIYDKFQR---ATSVKRKLSAELAGNHNQELTPCMRTCL----------------
Athual33f10    -PQQGCYPEGPMG--IIQHLEPSAHAAGCGKDS---------------------------
FthKa20g4      HVSRSPDEEAVARAPEDSSPAPEVFMNQLDRISEECEPWDAQDYHPLIFQ-DASITFVNT
hTASK          -STAAAGGGGFRNVYAEVLHFQSMCSCLWYKSREKLQYSIPMIIPRDLSTSDTCVEQSHS AthTb005e07    ------------------------------------------------------------
hTWIK-1        ------------------------------------------------------------
mTRAAK         LAFIDESSDTQSERGCALPRAPRGRRRPNPSKKPSRPRGPGRLRDKAVPV----------
mTREK-1        ------------------------------------------------------------
Athual33f10    ------------------------------------------------------------
FthKa20g4      EAGLSDEETSKSSLEDNLAGEESPQQGAEAKAPLNMGEFPSSSESTFTSTESELSVPYEQ
hTASK          SPGGGGRYSDTPSRRCLCSGAPRSAISSVSTGLHSLSTFRGLMKRRSSV-----------

AthTb005e07    ---------------
hTWIK-1        ---------------
mTRAAK         ---------------
mTREK-1        ---------------
Athual33f10    ---------------
FthKa20g4      LMNEYNKANSPKGT
hTASK          ---------------
```

Fig. 7 (continued)

Clustal W (1.74) multiple sequence alignment

```
hTWIK-1       -------MLQSLAGSSCVRLVERHRSAWCFGFLVLG----------------YLLYLVF
AthTb005e07   --------------------MRRGALLAGALAA---------------YAAYLVL
mTRAAK        ------------------MRSTTLLALLAL----------------VLLYLVS
mTREK-1       MAAPDLLDPKSAAQNSKPRLSFSSKPTVLASRVESDSAINVMKWKTVSTIFLVVVLYLII
hTASK         -----------------MKRQNVRTLALIVC----------------TFTYLLV
                                                               **:

hTWIK-1       GAVVFSSVELPYEDLLRQELRKLKRRFLEEHECLSEQQLEQFLGRVLEASNYGVSVLSNA
AthTb005e07   GALLVARLEGPHEARLRAELETLRAQLLQRSPCVAAPALDAFVERVLAAGRLGRVVLANA
mTRAAK        GALVFQALEQPHEQQAQKKMDHGRDQFLRDHPCVSQKSLEDFIKLLVEALGGGANPETSW
mTREK-1       GAAVFKALEQPQEISQRTTIVIQKQTFIAQHACVNSTELDELIQQIVAAINAGIIPLGNS
hTASK         GAAVFDALESEPELIERQRLEL-RQQELRARYNLSQGGYEELERVVLRLKPHKAGVQ---
              ** :. :*    *    :   :    :     :     : :    ::

hTWIK-1       SGNWN-----WDFTSALFFASTVLSTTGYGHTVPLSDGGKAFCIIYSVIGIPFTLLFLTA
AthTb005e07   SGSANASDPAWDFASALFFASTLITTVGYGYTTPLTDAGKAFSIAFALLGVPTTMLLLTA
mTRAAK        TNSSNHSS-AWNLGSAFFFSGTIITTIGYGNIVLHTDAGRLFCIFYALVGIPLFGMLLAG
mTREK-1       SNQVSH----WDLGSSFFFAGTVITTIGFGNISPRTEGGKIFCIIYALLGIPLFGFLLAG
hTASK         ---------WRFAGSFYFAITVITTIGYGHAAPSTDGGKVFCMFYALLGIPLTLVMFQS
                       *  :  .:::*: *:::* *:*         ::.*: *.: ::::*:*   .:: .

hTWIK-1       VVQRITVHVTR--RPVLYFHIRWGFSKQVVAIVHAVLLGFVTVSCFFFIPAAVFSVLEDD
AthTb005e07   SAQRLSLLLTH--VPLSWLSMRWGWDPRRAACWHLVALLGVVVTVCFLVPAVIFAHLEEA
mTRAAK        VGDRLGSSLRRGIGHIEAIFLKWHVPPGLVRSLSAVLFLLIGCLLFVLTPTFVFSYMES-
mTREK-1       VGDQLGTIFGKGIAKVEDTFIKWNVSQTKIRIISTIIFILFGCVLFVALPAVIFKHIEG-
hTASK         LGERINTLVRY---LLHRAKKGLGMRRADVSMANMVLIGFFSCISTLCIGAAAFSHYEH-
              :::    .      :          :               : :  .    .: *   * hTWIK-1       WNFLESFYFCFISLSTIGLGDYVPGEGYNQ-----KFRELYKIGITCYLLLGLIAMLVVL
AthTb005e07   WSFLDAFYFCFISLSTIGLGDYVPGEAPGQ-----PYRALYKVLVTBYLFLGLVAMVLVL
mTRAAK        WSKLEAIYFVIVTLTTVGFGDYVPGDTGQNS--PAYQPLVWFWILFGLAYFASVLTTIG
mTREK-1       WSALDAIYFVVITLTTIGFGDYVAGGSDIEYL--DFYKPVVWFWILVGLAYFAAVLAMIG
hTASK         WTFFQAYYYCFITLTTIGFGDYVALQKDQALQTQPQYVAFSFVYILTGLTVIGAFLNLVV
              *. ::: *: .::*:*:*:****.      :    . :  *    :

hTWIK-1       ETFCELHELKKFRKMFYVKKDK--DEDQVHIIEHDQLSFSSITDQAAGMKEDQKQNEPFV
AthTb005e07   QTFRHVSDLHGLTELILLPPP---CPASFNADEDDRV------DILGPQPESHQQ---LS
mTRAAK        NWLRAVSRRTRAEMGGLTAQAA--SWTGTVTARVTQR-----TGPSAPPPEKEQPLLPSS
mTREK-1       DWLRVISKKTKEEVGEFRAHAA--EWTANVTAEFKETR----RRLSVEIYDKFQR---AT
hTASK         LRFMTMNAEDEKRDAEHRALLTRNGQAGGGGGGSAHTTDTASSTAAAGGGGTRNVYAEV
              :  :                                              :

hTWIK-1       ATQSSACVDGPANH----------------------------------
AthTb005e07   ASSHTDYASIPR----------------------------------
mTRAAK        LPAPPAVVEPAGRPGSPA-PAEKVETPSPPTASALDYPSENLA-FIDESSDTQSERGCAL
mTREK-1       SVKRKLSAELAGNHNQELTPCMRTCL----------------------
hTASK         LHFQSMCSCLWYKSREKLQYSIPMIIPRDLSTSDTCVEQSHSSPGGGGRYSDTPSRRCLC hTWIK-1       --------------------------------
AthTb005e07   --------------------------------
mTRAAK        PRAPRGRRRPNPSKKPSRPRGPGRLRDKAVPV
mTREK-1       --------------------------------
hTASK         SGAPRSAISSVSTGLHSLSTFRGLMKRRSSV-
```

Fig. 8

Clustal w (1.74) multiple sequence alignment

```
                                                       TM 1
Athua133f10  -MYRPRARAAPEGRVRGCAVPGTVLLLLAYLAYLALGTGVFWTLEGRAAQDSSRSFQRDK
h TASK2      ----------------MVDRGPLLTSAIIFYLAIGAAIFEVLEEPHWKEAKKNYYTQK
hTWIK-1      MLQSLAGSSCVRLVERHRSAWCFGFLVLGYLLYLVFGAVVFSSVELPYEDLLRQELRKLK
hTASK        --------------MKRQNVRTLALIVCTFTYLLVGAAVFDALESEPE-LIERQRLELR
                             *   :  ** .*: :*  :*    P-LOOP 1 ::    :

Athua133f10  WELLQNFTCLDRPALDSLIRDVVQAYKNGASLLSNTTSMGRWELVGSFFFSVSTITTIGY
h TASK2      LHLLKEFPCLGQEGLDKILEVVSDAAGQGVAITGNQTFNN-WNWPNAMIFAATVITTIGY
hTWIK-1      RRFLEEHECLSEQQLEQFLGRVLEASNYGVSVLSNASGNWNWDFTSALFFASTVLSTTGY
hTASK        QQELRARYNLSQGGYEELERVVLRLKPH---KAGVQ-----WRFAGSFYFAITVITTIGY
              .*.  *..  :.:  *         .    *     *    .:: *: :.:;* **
                                  TM 2             .
Athua133f10  GNLSPNTMAARLFCIFFALVGIPLNLVVLNRLGHLMQQGVNH--WASRLGGTWQDPDKAR
h TASK2      GNVAPKTPAGRLFCVFYGLFGVPLCLTWISALGKFFGGRAKR--LGQFLTKRGVSLRKAQ
hTWIK-1      GHTVPLSDGGKAFCIIYSVIGIPFTLLFLTAVVQRITVHVTRRPVLYFHIRWGFSKQVVA
hTASK        GHAAPSTDGGKVFCMFYALLGIPLTLVMFQSLGERINTLVRY-LLHRAKKGLGMRRADVS
             *:  *  :  ..: **:::.:.*:*: *   : : . .
              TM 3                                     P-LOOP 2
Athua133f10  WLAGSGALLSGLLLFLLLPPLLFSHMEG-WSYTEGFYFAFITLSTVGFGDYVIG-MNPSQ
h TASK2      ITCTVIFIVWGVLVHLVIPPFVFMVTEG-WNYIEGLYYSFITISTIGFGDFVAG-VNPSA
hTWIK-1      IVHAVLLGFVTVSCFFFIPAAVFSVLEDDWNFLESFYFCFISLSTIGLGDYVPG-EGYNQ
hTASK        MANMVLIGFFSCISTLCIGAAAFSHYEH-WTFFQAYYYCFITLTTIGFGDYVALQKDQAL
             :    :  . *     *  *.: :.  *:.**:::*:*:**;*
                TM 4
Athua133f10  RYPLWYKNMVSLWILFGMAWLALIIKLILSQLETPGRVCSCCHHSSKEDFKS--------
h TASK2      NYHALYRYFVELWIYLGLAWLSLFVNWKVSMFVEVHKAIKKRRRRRKESFESSPHSRKAL
hTWIK-1      KFRELYKIGITCYLLLGLIAM-LVVLETFCELHELKKFRKMFYVKKDKDEDQ--------
hTASK        QTTPQYVAFSFVYILTGLTVIGAFLNLVVLRFMTMNAEDEKRDAEHRALLTRNG------
               .    *    :: *: :   .:   . :

Athua133f10  -----------------------------------QSWRQGPDREPESHSPQQGCYPEG
h TASK2      QVKGSTASKDVNIFSFLSKKEETYNDLIKQIGKKAMKTSGGGETGPGPGLGPQGGGLPAL
hTWIK-1      -----------------------------------VHIIEHDQLSFSSITDQAAGMKED
hTASK        Q----------------------------------AGGGGGGGSAHTTDTASSTAAAGGGG
                                                                              .
Athua133f10  PMGIIQHLEPSAHAAGCGKDS---------------------------------------
h TASK2      PPSLVPLVVYSKNRVPTLEEVSQTLRSKGHVSRSPDEEAVARAPEDSSPAPEVFMNQLDR
hTWIK-1      QKQNEPFVATQSSACVDGPANH--------------------------------------
hTASK        FRNVYAEVLHFQSMCSCLWYKSREKLQYSIPMIIPRDLSTSDTCVEQSHSSPGGGGRYSD
                                                                     :
Athua133f10  ------------------------------------------------------------
h TASK2      ISEECEPWDAQDYHPLIFQDASITFVNTEAGLSDEETSKSSLEDNLAGEESPQQGAEAKA
hTWIK-1      ------------------------------------------------------------
hTASK        TPSRRCLCSGAPRSAISSVSTGLHSLSTFRGLMKRRSSV---------------------

Athua133f10  --------------------------------------------
h TASK2      PLNMGEFPSSSESTFTSTESELSVPYEQLMNEYNKANSPKGT
hTWIK-1      --------------------------------------------
hTASK        --------------------------------------------
```

Fig. 9

GAP of: twik2.pep  check: 1565  from: 1  to: 499

TWIK2 FthKa20g4 to: twik3.pep  check: 8445  from: 1  to: 332

TWIK3 Athua133f10 - jthua133f10, 1575 bases, 18 checksum.

Symbol comparison table:
/usr/local/gcg_9.1/gcgcore/data/rundata/blosum62.cmp
CompCheck: 6430

```
          Gap Weight:      12      Average Match:    2.912
       Length Weight:       4      Average Mismatch: -2.003

Quality:     396             Length:      517
               Ratio:   1.193               Gaps:        3
   Percent Similarity:  40.764    Percent Identity:   32.166
```

Match display thresholds for the alignment(s):
| = IDENTITY
: = 2
. = 1 twik2.pep x twik3.pep

```
  1 ................MVDRGPLLTSAIIFYLAIGAAIFEVLEEPHWKE  33
                   |  || | : |||:|  :|  ||      .:
  1 MYRPRARAAPEGRVRGCAVPGTVLLLLAYLAYLALGTGVFWTLEGRAAQD  50

34 AKKNYYTQKLHLLKEFPCLGQEGLDKILEVVSDAAGQGVAITGNQT.FNN  82
    . :.:   |  ||. | ||  . || ::   |    |  .: | |
 51 SSRSFQRDKWELLQNFTCLDRPALDSLIRDVVQAYKNGASLLSNTTSMGR 100

83 WNWPNAMIFAATVITTIGYGNVAPKTPAGRLFCVFYGLFGVPLCLTWISA 132
    |   . |. . |||||||||..| | | |||:|:  | |:|| | :.
101 WELVGSFFFSVSTITTIGYGNLSPNTMAARLFCIFFALVGIPLNLVVLNR 150

133 LGKFFGGRAKRLGQFLTKRGVSLRKAQITCTVIFIVWGVLVHLVIPPFVF 182
    ||          |          ||.      :. |.|. |.:|| .|
151 LGHLMQQGVNHWASRLGGTWQDPDKARWLAGSGALLSGLLLFLLLPPLLF 200

183 MVTEGWNYIEGLYYSFITISTIGFGDFVAGVNPSANYHALYRYFVELWIY 232
    |||.| || |:.|||:||:|||||:| |.|||  | |: | |||
201 SHMEGWSYTEGFYFAFITLSTVGFGDYVIGMNPSQRYPLWYKNMVSLWIL 250

233 LGLAWLSLFVNWKVSMFVEVHKAIKKRRRRRKESFESSPHSRKALQVKGS 282
    |:|||.| :  .|     :      || |.|    |.  .
251 FGMAWLALIIKLILSQLETPGRVCSCCHHSSKEDFKSQSW.RQGPDREPE 299

283 TASKDVNIFSFLSKKEETYNDLIKQIGKKAMKTSGGGETGPGPGLGPQGG 332
    . |   :      |   :|.:  |     | :.
300 SHSPQQGCY......PEGPMGIIQHLEPSAHAAGCGKDS............ 332
```

Fig. 10

GAP of: twik4.pep  check: 9188  from: 1 to: 313

TWIK4 AthTb005e07 - jthTb005e07, 2287 bases, 4935 checksum.

to: twik2.pep  check: 1565  from: 1 to: 499

TWIK2 FthKa20g4

Symbol comparison table:
/usr/local/gcg_9.1/gcgcore/data/rundata/blosum62.cmp
CompCheck: 6430

```
        Gap Weight:     12      Average Match:     2.912
     Length Weight:      4      Average Mismatch: -2.003

Quality:    221             Length:      512
             Ratio:  0.706               Gaps:        5
 Percent Similarity: 37.667   Percent Identity:   27.333
```

Match display thresholds for the alignment(s):
```
          | = IDENTITY
          : = 2
          . = 1
``` twik4.pep x twik2.pep..

```
  1 .MRRGALLAGALAAYAAYLVLGALLVARLEGPHEARLRAELETLRAQLLQ  49
    . || ||  |:    || :|| :  || ||    :    |  :  ||.
  1 MVDRGPLLTSAI...IFYLAIGAAIFEVLEEPHWKEAKKNYYTQKLHLLK  47

50 RSPCVAAPALDAFVERVLAAGRLGRVVLANASGSANASDPAWDFASALFF  99
    ||.   || .||  |  |  |:  |  .       |.. .|: |
 48 EFPCLGQEGLDKILEVVSDAAGQGVAITGNQTFN......NWNWPNAMIF  91

100 ASTLITTVGYGYTTPLTDAGKAFSIAFALLGVPTTMLLLTASAQRLSLLL 149
    |.|.|||:|||   | | ||: |  :  :|  ||| : :.|  .
 92 AATVITTIGYGNVAPKTPAGRLFCVFYGLFGVPLCLTWISALGKFFGGRA 141

150 THVPLSWLSMRWGWDPRRAACWHLVALLGVVVTVCFLVPAVIFAHLEEAW 199
      | :|   |:|      |  :  ||  .:|  :|  . ||
142 KR..LGQFLTKRGVSLRKAQITCTVIFIVWGVLVHLVIPPFVFM.VTEGW 188

200 SFLDAFYFCFISLSTIGLGDYVPGEAPGQPYRALYKVLVTVYLFLGLVAM 249
    .:::   |:  ||.:||||  ||:|  |   | |||:  |  .::::||| |
189 NYIEGLYYSFITISTIGFGDFVAGVNPSANYHALYRYFVELWIYLGL.AW 237

250 VLVLQTFRHVSDLHGLTELILLPPPCPASFNADEDDRVDILGPQPESHQQ 299
    . .   .:   .       :              || .   |  :    . .
238 LSLFVNWKVSMFVEVHKAIKKRRRRRKESFESSPHSRKALQVKGSTASKD 287

300 LSASSHTDYASIPR................................... 313
    .. |
288 VNIFSFLSKKEETYNDLIKQIGKKAMKTSGGGETGPGPGLGPQGGGLPAL 337
```

Fig. 11

```
GAP of: twik3.pep   check: 8445   from: 1   to: 332

TWIK3 Athua133f10 - jthua133f10, 1575 bases, 18 checksum.

to: twik4.pep   check: 9188   from: 1   to: 313

TWIK4 AthTb005e07 - jthTb005e07, 2287 bases, 4935 checksum.

Symbol comparison table:
/usr/local/gcg_9.1/gcgcore/data/rundata/blosum62.cmp
 CompCheck: 6430

Gap Weight:       12        Average Match:    2.912
     Length Weight:        4        Average Mismatch: -2.003

Quality:      257               Length:      345
             Ratio:    0.821                 Gaps:        7
 Percent Similarity:  40.333        Percent Identity: 31.667

Match display thresholds for the alignment(s):
                    | = IDENTITY
                    : = 2
                    . = 1 twik3.pep x twik4.pep..

1 MYRPRARAAPEGRVRGCAVPGTVLLLLAYLAYLALGTGVFWTLEGRAAQD 50
               ||  . |   ||| ||| ||  . |    |||
  1 ...........MRRGALLAGA...LAAYAAYLVLGALLVARLEGPHEAR 35

51 SSRSFQRDKWELLQNFTCLDRPALDSLIRDVVQAYKNGASLLSNTTSMGR 100
     : ::|||   |. ||||.  |. | | .|. 
 36 LRAELETLRAQLLQRSPCVAAPALDAFVERVLAAGRLGRVVLANASGSAN 85

101 .....WELVGSFFFSVSTITTIGYGNLSPNTMAARLFCIFFALVGIPLNL 145
         |:  . ||.. |||:|||  .||| : |  |||.|:| :
 86 ASDPAWDFASALFFASTLITTVGYGYTTPLTDAGKAFSIAFALLGVPTTM 135

146 VVLNRLGHLMQQGVNHW.ASRLGGTW.QDPDKARWLAGSGALLSGLLLFL 193
    ..|    :   .| || |  | ||:|      |     . . 
136 LLLTASAQRLSLLLTHVPLSWLSMRWGWDPRRAACWHLVALLGVVVTVCF 185

194 LLPPLLFSHM.EGWSYTEGFYFAFITLSTVGFGDYVIGMNPSQRYPLWYK 242
    |.|  .:|.|: |  ||:  :|| ||.|||: |||||  |  |   ||
186 LVPAVIFAHLEEAWSFLDAFYFCFISLSTIGLGDYVPGEAPGQPYRALYK 235

243 NMVSLWILFGMAWLALIIKLILSQLETPG.....RVCSCCHHSSKEDFKS 287
    :|..::    |:  : |::.      : |    .  | | |
236 VLVTVYLFLGLVAMVLVLQTFRHVSDLHGLTELILLPPPCPASFNADEDD 285

288 QSWRQGPDREPESHSPQQGCYPEGPMGIIQHLEPSAHAAGCGKDS 332
      ||  :||||       | .
286 RVDILGP..QPESHQQLSASSHTDYASIPR............... 313
```

Fig. 12

```
GAP of: htwik-1.pep  ch ck: 4093   from: 1  to: 336 hTWIK-1 U33632 Human two P-domain K+ channel TWIK-1 mRNA, complete cds.

to: twik2.pep   check: 1565   from: 1  to: 499

TWIK2 FthKa20g4

Symbol comparison table:
/usr/local/gcg_9.1/gcgcore/data/rundata/blosum62.cmp
 CompCheck: 6430

Gap Weight:     12       Average Match:    2.912
       Length Weight:      4       Average Mismatch: -2.003

Quality:   269               Length:    521
                Ratio:  0.801                Gaps:      4
   Percent Similarity: 36.943    Percent Identity: 26.433

Match display thresholds for the alignment(s):
                   | = IDENTITY
                   : = 2
                   . = 1 htwik-1.pep x twik2.pep

1 MLQSLAGSSCVRLVERHRSAWCFGFLVLGYLLYLVFGAVVFSSVELPYED  50
                        | : ||   || :|  .| |:
     1 ..................MVDRGPLLTSAIIFYLAIGAAIFEVLEEPHWK  32

51 LLRQELRKLKRRFLEEHECLSEQQLEQFLGRVLEASNYGVSVLSNASGNW 100
       :.        |    |.|   ||  :: |:. |   |:|. ||.:   |  . |
    33 EAKKNYYTQKLHLLKEFPCLGQEGLDKILEVVSDAAGQGVAITGNQTFN.  81

101 NWDFTSALFFASTVLSTTGYGHTVPLSDGGKAFCIIYSVIGIPFTLLFLT 150
       ||.. .|: ||.||:.| |||.   |   .   |: ||: |  .|:|   | .:.
    82 NWNWPNAMIFAATVITTIGYGNVAPKTPAGRLFCVFYGLFGVPLCLTWIS 131

151 AVVQRITVHVTRRPVLYFHIRWGFSKQVVAIVHAVLLGFVTVSCFFFIPA 200
       |..     |   .   |   :||  .   |  |:    |        ||
   132 ALGKFFGGRAKR..LGQFLTKRGVSLRKAQITCTVIFIVWGVLVHLVIPP 179

201 AVFSVLEDDWNFLESFYFCFISLSTIGLGDYVPGEGYNQKFRELYKIGIT 250
       ||||  ||::|  |: ||.:||||  ||:|   .  :  ||:  :
   180 FVFMVTE.GWNYIEGLYYSFITISTIGFGDFVAGVNPSANYHALYRYFVE 228

251 CYLLLGL..IAMLVVLETFCELHELKKFRKMFYVKKDKDEDQVHIIEHDQ 298
       :: |||  :.:|   .   .     |:|    :|:  |   |   . |
   229 LWIYLGLAWLSLFVNWKVSMFVEVHKAIKKRRRRRKESFESSPHSRKALQ 278

299 LSFSSITDQAAGMKEDQKQNEPFVATQSSACVDGPANH............ 336
         . |..          |.| :
   279 VKGSTASKDVNIFSFLSKKEETYNDLIKQIGKKAMKTSGGGETGPGPGLG 328
```

Fig. 13

GAP of: htwik-1.pep   check: 4093   from: 1   to: 336 hTWIK-1 U33632 Human two P-domain K+ channel TWIK-1 mRNA, complete cds.

to: twik3.pep   check: 8445   from: 1   to: 332

TWIK3 Athua133f10 - jthua133f10, 1575 bases, 18 checksum.

Symbol comparison table:
/usr/local/gcg_9.1/gcgcore/data/rundata/blosum62.cmp
 CompCheck:  6430

```
         Gap Weight:       12      Average Match:     2.912
      Length Weight:        4      Average Mismatch: -2.003

Quality:      199             Length:       337
              Ratio:    0.599               Gaps:         3
  Percent Similarity:  31.420    Percent Identity:  22.961
```

Match display thresholds for the alignment(s):
```
                | = IDENTITY
                : =    2
                . =    1
``` htwik-1.pep x twik3.pep..

```
  1 MLQSLAGSSCVRLVERHRSAWCFGFLVLGYLLYLVFGAVVFSSVELPYED  50
    :             |.    |.|||  ||  |  ||  ..|
  1 .MYRPRARAAPEGRVRGCAVPGTVLLLLAYLAYLALGTGVFWTLEGRAAQ  49

51 LLRQELRKLKRRFLEEHECLSEQQLEQFLGRVLEASNYGVSVLSNASGNW 100
     . .:  |   |:   ||     |:  :  |.:    ||.|||.
 50 DSSRSFQRDKWELLQNFTCLDRPALDSLIRDVVQAYKNGASLLSNTTSMG  99

101 NWDFTSALFFASTVLSTTGYGHTVPLSDGGKAFCIIYSVIGIPFTLLFLT 150
    |:  . ||. . :.| |||.  | .  : ||| :..:|||  |. |
100 RWELVGSFFFSVSTITTIGYGNLSPNTMAARLFCIFFALVGIPLNLVVLN 149

151 AVVQRITVHVTRRPVLYFHIRWGFSKQVVAIVHAVLLGFVTVSCFFFIPA 200
          |              |              ||  .  |  :|
150 RLGHLMQQGVNHWASRLGGTWQDPDKARWLAGSGALLSGLLL..FLLLPP 197

201 AVFSVLEDDWNFLESFYFCFISLSTIGLGDYVPGEGYNQKFRELYKIGIT 250
    .||  :|  |.: |  ||| ||.|||:| ||||  | .|::  || :.
198 LLFSHME.GWSYTEGFYFAFITLSTVGFGDYVIGMNPSQRYPLWYKNMVS 246

251 CYLLLGLIAMLVVLE.TFCELHELKKFRKMFYVKKDKDEDQVHIIEHDQL 299
    ::|  |:  :  .::.     :|    :     .|        :
247 LWILFGMAWLALIIKLILSQLETPGRVCSCCHHSSKEDFKSQSWRQGPDR 296

300 SFSSITDQAAGMKEDQKQNEPFVATQSSACVDGPANH 336
    |  .|    |    | .  .|    |  .
297 EPESHSPQQGCYPEGPMGIIQHLEPSAHAAGCGKDS. 332
```

Fig. 14

GAP of: htwik-1.pep  check: 4093  from: 1  to: 336 hTWIK-1 U33632 Human two P-domain K+ channel TWIK-1 mRNA, complete cds.

to: twik4.pep  check: 9188  from: 1  to: 313

TWIK4 AthTb005e07 - jthTb005e07, 2287 bases, 4935 checksum.

Symbol comparison table:
/usr/local/gcg_9.1/gcgcore/data/rundata/blosum62.cmp
CompCheck: 6430

```
         Gap Weight:      12        Average Match:    2.912
      Length Weight:       4     Average Mismatch:   -2.003

Quality:     575              Length:      353
              Ratio:   1.837                Gaps:        4
  Percent Similarity:  55.405    Percent Identity:   46.28
         Match display thresholds for the alignment(s):
                      | = IDENTITY
                      : =    2
                      . =    1
htwik-1.pep x twik4.pep..
                 .         .         .         .         .
    1 MLQSLAGSSCVRLVERHRSAWCFGFLVLGYLLYLVFGAVVFSSVELPYED 50
                       ||  ||   |    |  |||  ||... .|  :|
    1 ..............MRRGALLAGALA.AYAAYLVLGALLVARLEGPHEA 34

.         .         .         .         .
   51 LLRQELRKLKRRFLEEHECLSEQQLEQFLGRVLEASNYGVSVLSNASGNW 100
      || ||   |: . |:     |..    |: |.|||| |   ||.||||.
   35 RLRAELETLRAQLLQRSPCVAAPALDAFVERVLAAGRLGRVVLANASGSA 84

.         .         .         .         .
  101 N.....WDFTSALFFASTVLSTTGYGHTVPLSDGGKAFCIIYSVIGIPFT 145
      |     ||| ||||||||.:.|  |||:| ||.| ||||  |:..:|:| |
   85 NASDPAWDFASALFFASTLITTVGYGYTTPLTDAGKAFSIAFALLGVPTT 134

.         .         .         .         .
  146 LLFLTAVVQRITVHVTRRPVLYFHIRWGFSKQVVAIVHAVLLGFVTVSCF 195
      :|  |||   ||:...|   |. :  .|||.  .  |   |||| ||  |.
  135 MLLLTASAQRLSLLLTHVPLSWLSMRWGWDPRRAACWHLVALLGVVVTVC 184

.         .         .         .         .
  196 FFIPAAVFSVLEDDWNFLESFYFCFISLSTIGLGDYVPGEGYNQKFRELY 245
      | :|| :|. ||: |.||:.||||||||||||||||||  :|  ||
  185 FLVPAVIFAHLEEAWSFLDAFYFCFISLSTIGLGDYVPGEAPGQPYRALY 234

.         .         .         .         .
  246 KIGITCYLLLGLIAMLVVLETFCELHELKKFRKMFYVK.......KDKDE 288
      |: :| || |||:||..||:||  .:|   .:  .            ::
  235 KVLVTVYLFLGLVAMVLVLQTFRHVSDLHGLTELILLPPPCPASFNADED 284

.         .         .         .         .
  289 DQVHII.....EHDQLSFSSITDQAAGMKEDQKQNEPFVATQSSACVDGP 333
      |.| |:     |  ||| || ||  |.   :
  285 DRVDILGPQPESHQQLSASSHTDYASIPR..................... 313
                 .
                 .
                 .
```

Fig. 15

GAP of: htask2.pep  check: 1565  from: 1  to: 499 hTASK2 3925427 in GenPept to: twik2.pep  check: 1565  from: 1  to: 499

TWIK2 FthKa20g4

Symbol comparison table:
/usr/local/gcg_9.1/gcgcore/data/rundata/blosum62.cmp
CompCheck: 6430

```
         Gap Weight:       12       Average Match:      2.912
      Length Weight:        4       Average Mismatch:  -2.003

Quality:     2613               Length:       499
              Ratio:    5.236                 Gaps:         0
  Percent Similarity:  100.000     Percent Identity:   100.000
```

Match display thresholds for the alignment(s):
| = IDENTITY
: = 2
. = 1 htask2.pep x twik2.pep..

```
  1 MVDRGPLLTSAIIFYLAIGAAIFEVLEEPHWKEAKKNYYTQKLHLLKEFP  50
    |||||||||||||||||||||||||||||||||||||||||||||||||
  1 MVDRGPLLTSAIIFYLAIGAAIFEVLEEPHWKEAKKNYYTQKLHLLKEFP  50

51 CLGQEGLDKILEVVSDAAGQGVAITGNQTFNNWNWPNAMIFAATVITTIG 100
    |||||||||||||||||||||||||||||||||||||||||||||||||
 51 CLGQEGLDKILEVVSDAAGQGVAITGNQTFNNWNWPNAMIFAATVITTIG 100

101 YGNVAPKTPAGRLFCVFYGLFGVPLCLTWISALGKFFGGRAKRLGQFLTK 150
    |||||||||||||||||||||||||||||||||||||||||||||||||
101 YGNVAPKTPAGRLFCVFYGLFGVPLCLTWISALGKFFGGRAKRLGQFLTK 150

151 RGVSLRKAQITCTVIFIVWGVLVHLVIPPFVFMVTEGWNYIEGLYYSFIT 200
    |||||||||||||||||||||||||||||||||||||||||||||||||
151 RGVSLRKAQITCTVIFIVWGVLVHLVIPPFVFMVTEGWNYIEGLYYSFIT 200

201 ISTIGFGDFVAGVNPSANYHALYRYFVELWIYLGLAWLSLFVNWKVSMFV 250
    |||||||||||||||||||||||||||||||||||||||||||||||||
201 ISTIGFGDFVAGVNPSANYHALYRYFVELWIYLGLAWLSLFVNWKVSMFV 250

251 EVHKAIKKRRRRRKESFESSPHSRKALQVKGSTASKDVNIFSFLSKKEET 300
    |||||||||||||||||||||||||||||||||||||||||||||||||
251 EVHKAIKKRRRRRKESFESSPHSRKALQVKGSTASKDVNIFSFLSKKEET 300

301 YNDLIKQIGKKAMKTSGGGETGPGPGLGPQGGGLPALPPSLVPLVVYSKN 350
    |||||||||||||||||||||||||||||||||||||||||||||||||
301 YNDLIKQIGKKAMKTSGGGETGPGPGLGPQGGGLPALPPSLVPLVVYSKN 350
```

Fig. 16

```
351 RVPTLEEVSQTLRSKGHVSRSPDEEAVARAPEDSSPAPEVFMNQLDRISE 400
    ||||||||||||||||||||||||||||||||||||||||||||||||||
351 RVPTLEEVSQTLRSKGHVSRSPDEEAVARAPEDSSPAPEVFMNQLDRISE 400

401 ECEPWDAQDYHPLIFQDASITFVNTEAGLSDEETSKSSLEDNLAGEESPQ 450
    ||||||||||||||||||||||||||||||||||||||||||||||||||
401 ECEPWDAQDYHPLIFQDASITFVNTEAGLSDEETSKSSLEDNLAGEESPQ 450

451 QGAEAKAPLNMGEFPSSSESTFTSTESELSVPYEQLMNEYNKANSPKGT 499
    |||||||||||||||||||||||||||||||||||||||||||||||||
451 QGAEAKAPLNMGEFPSSSESTFTSTESELSVPYEQLMNEYNKANSPKGT 499
```

Fig. 16 (continued)

>human TWIK 5
CTAGGGAGGGCGCCATCTGAGTAGTTCGGAAGAACTGAACATGATGAGTT
GCCGGCTGCTTCCTGAGTCCTTGGGGAAGCACACGCACCATCCACTTAGC
ACTGGAGCCTGGCTGTTCTCCGGGCACTCCTACCCCATCTTCCTGGCGGG
GCTTAGATGCTCCTGCCTCTTCCACCAGCTCCTCTTGCCCTGCATGCTTC
AGGGACGATGGAGGTCTCGGGGCACCCCCAGGCCAGGAGATGCTGCCCAG
AGGCCCTGGGAAAGCTCTTCCCTGGCCTCTGCTTCCTCTGCTTTCTGGTG
ACCTACGCCCTGGTGGGTGCTGTGGTCTTCTCTGCCATTGAGGACGGCCA
GGTCCTGGTGGCAGCAGATGATGGAGAGTTTGAGAAGTTCTTGGAGGAGC
TCTGCAGAATCTTGAACTGCAGTGAAACAGTGGTGGAAGACAGAAAACAG
GATCTCCAGGGGCATCTGCAGAAGGTGAAGCCTCAGTGGTTTAACAGGAC
CACACACTGGTCCTTCCTGAGCTCGCTCTTTTTCTGCTGCACGGTGTTCA
GCACCGTGGGCTATGGCTACATCTACCCCGTCACCAGGCTTGGCAAGTAC
TTGTGCATGCTCTATGCTCTCTTTGGTATCCCCCTGATGTTCCTCGTTCT
CACGGACACAGGCGACATCCTGGCAACCATCTTATCTACATCTTATAATC
GGTTCCGAAAATTCCCTTTCTTTACCCGCCCCCTCCTCTCCAAGTGGTGC
CCCAAATCTCTCTTCAAGAAAAAACCGGACCCCAAGCCCGCAGATGAAGC
TGTCCCTCAGATCATCATCAGTGCTGAAGAGCTTCCAGGCCCCAAACTTG
GCACATGTCCTTCACGCCCAAGCTGCAGCATGGAGCTGTTTGAGAGATCT
CATGCGCTAGAGAAACAGAACACACTGCAACTGCCCCCACAAGCCATGGA
GAGGAGTAACTCGTGTCCCGAACTGGTGTTGGGAAGACTCTCATACTCCA
TCATCAGCAACCTGGATGAAGTTGGACAGCAGGTGGAGAGGTTGGACATC
CCCCTCCCCATCATTGCCCTTATTGTTTTTGCCTACATTTCCTGTGCAGC
TGCCATCCTCCCCTTCTGGGAGACACAGTTGGATTTCGAGAATGCCTTCT
ATTTCTGCTTTGTCACACTCACCACCATTGGGTTTGGGGATACTGTTTTA
GAACACCCTAACTTCTTCCTGTTCTTCTCCATTTATATCATCGTTGGAAT
GGAGATTGTGTTCATTGCTTTCAAGTTGGTGCAAAACAGGCTGATTGACA
TATACAAAAATGTTATGCTATTCTTTGCAAAAGGGAAGTTTTACCACCTT
GTTAAAAAGTGAAGGTTTCATTATCTCTCAGGTGACAGACACTGGCTGAG
CTGGTTTTCTTGTGTTGTCTTTCAGGGTCATGCAGCCTGTCACCTGAGAC
CTTCAGTCTTGGAGACAAATCCCTTATGAGAGCCAAGTTCAGTCTTGAGG
CCCTGC MLLPLPPAPLALHASGTMEVSGHPQARRCCPEALGKLFPGLCFLCFLVTYALVGAVV
FSAIEDGQVLVAADDGEFEKFLEELCRILNCSETVVEDRKQDLQGHLQKVKPQWFNR
TTHWSFLSSLFFCCTVFSTVGYGYIYPVTRLGKYLCMLYALFGIPLMFLVLTDTGDI
LATILSTSYNRFRKFPFFTRPLLSKWCPKSLFKKKPDPKPADEAVPQIIISAEELPG
PKLGTCPSRPSCSMELFERSHALEKQNTLQLPPQAMERSNSCPELVLGRLSYSIISN
LDEVGQQVERLDIPLPIIALIVFAYISCAAAILPFWETQLDFENAFYFCFVTLTTIG
FGDTVLEHPNFFLFFSIYIIVGMEIVFIAFKLVQNRLIDIYKNVMLFFAKGKFYHLV
KK

Fig. 17

GAP of: ORBa005gy  ch ck: 9848  from: 1 to: 401

TWIK-5 protein (analysis onl - Import - compl t to: PRBa005gy  check: 4672  from: 1 to: 394

2465542 in GenPept

Symbol comparison table: /prod/ddm/seqanal/BLAST/matrix/aa/PAM250
CompCheck:  5553

```
        Gap Weight:       25        Average Match:    2.617
     Length Weight:        1        Average Mismatch: -3.416

Quality:      166               Length:      538
             Ratio:    0.421                 Gaps:        5
Percent Similarity:   49.805      Percent Identity:   29.183
```

Match display thresholds for the alignment(s):
  | = IDENTITY
  : = 2
  . = 1

ORBa005gy x PRBa005gy

```
  1 MLLPLPPAPLALHASGTMEVSGHPQARRCCPEALGKLFPGLCFLCFLVTY  50
                                       . ::        ||
  1 ..............................MKRQNVRTLALIVCTFTY  18

51 ALVGAVVFSAIEDGQVLVAADDGEFEKFLEELCRILNCSETVVEDRKQDL 100
    ||||  ||  |:    | :   : |: .    .|     : :.   ::|
 19 LLVGAAVFDALESEPELIERQRLELRQ......QELRARYNLSQGGYEEL  62

101 QGHLQKVKPQWFNRTTHWSFLSSLFFCCTVFSTVGYGYIYPVTRLGKYLC 150
    :  :::||:   .   :|  |  .|::|  ||..|:|||    |  || :|
 63 ERVVLRLKPH..KAGVQWRFAGSFYFAITVITTIGYGHAAPSTDGGKVFC 110

151 MLYALFGIPLMFLVLTDTGDILATILSTSYNRFRKFPFFTRPLLSKWCPK 200
    |:||||:|||  ::::    |: :  |:::        :|  :|
111 MFYALLGIPLTLVMFQSLGERINTLVRYLLHRAKK............... 145

251 LEKQNTLQLPPQAMERSNSCPELVLGRLSYSIISNLDEVGQQVERLDIPL 300
                                              |  :  |  |:..:
146 .........................................GLGMRRADVSM 156

301 PIIALIVF...AYISCAAAILPFWETQLDFENAFYFCFVTLTTIGFGD.. 345
    . :||| |   | .|    :  |.|:|:||:||||||||
157 ANMVLIGFFSCISTLCIGAAAFSHYEHWTFFQAYYYCFITLTTIGFGDYV 206

346 ......TVLEHPNFFLFFSIYIIVGMEIVFIAFKLVQNRLIDIYKNVMLF 389
          .: :|.: | :||: |: ::    :.||   |:: :  .
207 ALQKDQALQTQPQYVAFSFVYILTGLTVIGAFLNLVVLRFMTMNAEDEKR 256

390 FAKGKFYHLVKK..................................... 401
    |  |  :  .
257 DAEHRALLTRNGQAGGGGGGGSAHTTDTASSTAAAGGGGFRNVYAEVLHF 306
```

Fig. 19

```
GAP of: GRBa005gy  ch ck: 9848  from: 1  to: 401
TWIK-5 prot in (analysis onl - Import - complet
to: HRBa005gy  check: 2856  from: 1  to: 426
4101566 in GenPept Symbol comparison table: /prod/ddm/seqanal/BLAST/matrix/aa/PAM250
CompCheck: 5553

Gap Weight:     25        Average Match:    2.617
       Length Weight:      1        Average Mismatch: -3.416

Quality:     77              Length:    563
                Ratio:  0.192                Gaps:      6
  Percent Similarity: 44.697      Percent Identity: 27.273

Match display thresholds for the alignment(s):
                 | = IDENTITY
                 : = 2
                 . = 1

GRBa005gy x HRBa005gy

1 ............................MLLPLPPAPLALHASGTM  18
                                |.:.   | |  .
  1 MLPSASRERPGYRAGVAAPDLLDPKSAAQNSKPRLSFSTKPTVLASRVES  50

19 EVSGHPQARRCCPEALGKLFPGLCFLCFLVTYALVGAVVFSAIEDGQVLV  68
    : . : ::  .         .: :| | ::|| ||  |:|:  :
 51 DTTINVMKWKTVST..........IFLVVVLYLIIGATVFKALEQPHEIS  90

69 AADDGEFEK..FLEELCRILNCSETVVEDRKQDLQGHLQKVKPQWFNRTT 116
    .:|    |: :    : .  : :.         .|. .
 91 QRTTIVIQKQTFISQHSCVNSTELDELIQQIVAAINAGIIPLGNTSNQIS 140

117 HWSFLSSLFFCCTVFSTVGYGYIYPVTRLGKYLCMLYALFGIPLMFLVLT 166
    || : ||:|:|:..:|:|| | | :|:|||| :||| ::|.
141 HWDLGSSFFFAGTVITTIGFGNISPRTEGGKIFCIIYALLGIPLFGFLLA 190

167 DTGDILATILSTSYNRFRKFPFFTRPLLSKWCPKSLFKKKPDPKPADEAV 216
    .  || |.||:..
191 GVGDQLGTIFGKG.................................... 203
                                                :
                                                :
                                                :
267 SNSCPELVLGRLSYSIISNLDEVGQQVERLDIPLPIIALIVFAYISCA.. 314
    |..:::::     . .  :  : ||.|:| ..|
204 ...............IAKVEDTFIKWNVSQTKIRIISTIIFILFGCVLF 237

315 ...AAILPFWETQLDFENAFYCFVTLTTIGFGDTVLEHPNFFLFFSIYI 361
       .||:       :|.||  :|||||||||||           |:
238 VALPAIIFKHIEGWSALDAIYFVVITLTTIGFGD...............YV 273

362 IVGMEIVFIAFKLVQNRLIDIYKNVMLFFAKGKFYHLVKK.......... 401
    | :| ::| |           |||:| |     :  :
274 AGGSDIEYLDF..........YKPVVWFWILVGLAYFAAVLSMIGRLVRV 313
                                                :

Fig. 20
```

POTASSIUM CHANNEL MOLECULES AND USES THEREFOR

RELATED APPLICATIONS

This application is a division of Ser. No. 09/561,763 filed Apr. 28, 2000, now issued as U.S. Pat. No. 6,664,373, which is a continuation-in-part of Ser. No. 09/431,367 filed Nov. 1, 1999, now issued as U.S. Pat. No. 6,670,149, which is a continuation-in-part of Ser. No. 09/259,951 filed on Mar. 1, 1999, now abandoned. These applications are incorporated herein in their entirety by reference.

BACKGROUND OF THE INVENTION

Potassium ($K^+$) channels are ubiquitous proteins which are involved in the setting of the resting membrane potential as well as in the modulation of the electrical activity of cells. In excitable cells, $K^+$ channels influence action potential waveforms, firing frequency, and neurotransmitter secretion (Rudy, B. (1988) *Neuroscience*, 25, 729-749; Hille, B. (1992) *Ionic Channels of Excitable Membranes*, 2nd Ed.). In non-excitable cells, they are involved in hormone secretion, cell volume regulation and potentially in cell proliferation and differentiation (Lewis et al. (1995) *Annu. Rev. Immunol.*, 13, 623-653). Developments in electrophysiology have allowed the identification and the characterization of an astonishing variety of $K^+$ channels that differ in their biophysical properties, pharmacology, regulation and tissue distribution (Rudy, B. (1988) *Neuroscience*, 25, 729-749; Hille, B. (1992) *Ionic Channels of Excitable Membranes*, 2nd Ed.). More recently, cloning efforts have shed considerable light on the mechanisms that determine this functional diversity. Furthermore, analyses of structure-function relationships have provided an important set of data concerning the molecular basis of the biophysical properties (selectivity, gating, assembly) and the pharmacological properties of cloned $K^+$ channels.

Functional diversity of $K^+$ channels arises mainly from the existence of a great number of genes coding for pore-forming subunits, as well as for other associated regulatory subunits. Two main structural families of pore-forming subunits have been identified. The first one consists of subunits with a conserved hydrophobic core containing six transmembrane domains (TMDs). These $K^+$ channel α subunits participate in the formation of outward rectifier voltage-gated (Kv) and $Ca^{2+}$-dependent $K^+$ channels. The fourth TMD contains repeated positive charges involved in the voltage gating of these channels and hence in their outward rectification (Logothetis et al. (1992) *Neuron*, 8, 531-540; Bezanilla et al. (1994) *Biophys. J* 66, 1011-1021).

The second family of pore-forming subunits have only two TMDs. They are essential subunits of inward-rectifying (IRK), G-protein-coupled (GIRK) and ATP-sensitive ($K_{ATP}$) $K^+$ channels. The inward rectification results from a voltage-dependent block by cytoplasmic $Mg^{2+}$ and polyamines (Matsuda, H. (1991) *Annu. Rev. Physiol.*, 53, 289-298). A conserved domain, called the P domain, is present in all members of both families (Pongs, O. (1993) *J. Membr. Biol.*, 136, 1-8; Heginbotham et al. (1994) *Biophys. J* 66,1061-1067; Mackinnon, R. (1995) *Neuron*, 14, 889-892; Pascual et al., (1995) *Neuron.*, and 14, 1055-1063). This domain is an essential element of the aqueous $K^+$-selective pore. In both groups, the assembly of four subunits is necessary to form a functional $K^+$ channel (Mackinnon, R. (1991) *Nature*, 350, 232-235; Yang et al., (1995) *Neuron*, 15, 1441-1447.

In both six TMD and two TMD pore-forming subunit families, different subunits coded by different genes can associate to form heterotetramers with new channel properties (Isacoff et al., (1990) *Nature*, 345, 530-534). A selective formation of heteropolymeric channels may allow each cell to develop the best $K^+$ current repertoire suited to its function. Pore-forming α subunits of Kv channels are classified into different subfamilies according to their sequence similarity (Chandy et al. (1993) *Trends Pharmacol. Sci.*, 14, 434). Tetramerization is believed to occur preferentially between members of each subgroup (Covarrubias et al. (1991) *Neuron*, 7, 763-773). The domain responsible for this selective association is localized in the N-terminal region and is conserved between members of the same subgroup. This domain is necessary for hetero- but not homomultimeric assembly within a subfamily and prevents co-assembly between subfamilies. Recently, pore-forming subunits with two TMDs were also shown to co-assemble to form heteropolymers (Duprat et al. (1995) *Biochem. Biophys. Res. Commun.*, 212, 657-663. This heteropolymerization seems necessary to give functional GIRKs. IRKs are active as homopolymers but also form heteropolymers.

New structural types of $K^+$ channels were identified recently in both humans and yeast. These channels have two P domains in their functional subunit instead of only one (Ketchum et al. (1995) *Nature*, 376, 690-695; Lesage et al. (1996) *J. Biol. Chem*, 271, 41834187; Lesage et al. (1996) *EMBO J*, 15, 1004-1011; Reid et al. (1996) *Receptors Channels* 4, 51-62). The human channel called TWIK-1, has four TMDs. TWIK-1 is expressed widely in human tissues and is particularly abundant in the heart and the brain. TWIK-1 currents are time independent and inwardly rectifying. These properties suggest that TWIK1 channels are involved in the control of the background $K^+$ membrane conductance (Lesage et al. (1996) *EMBO J.*, 15, 1004-1011).

Table of Contents
Summary of the Invention
Brief Description of the Drawings
Detailed Description of the Invention
I. Isolated Nucleic Acid Molecules
II. Isolated TWIK Proteins and Anti-TWIK Antibodies
III. Recombinant Expression Vectors and Host Cells
IV. Pharmaceutical Compositions
V. Uses and Methods of the Invention
   A. Screening Assays
   B. Detection Assays
      1. Chromosome Mapping
      2. Tissue Typing
      3. Use of Partial TWIK Sequences in Forensic Biology
   C. Predictive Medicine
      1. Diagnostic Assays
      2. Prognostic Assays
      3. Monitoring of Effects During Clinical Trials
   D. Methods of Treatment
      1. Prophylactic Methods
      2. Therapeutic Methods
      3. Pharmacogenomics
Examples

SUMMARY OF THE INVENTION

The present invention is based, at least in part, on the discovery of novel members of the TWIK (for Tandem of P domains in a Weak Inward rectifying $K^+$ channel) family of potassium channels, referred to herein as TWIK-2, TWIK-3, TWIK-4, and TWIK-5 nucleic acid and protein molecules. The TWIK-2, TWIK-3, TWIK-4, and TWIK-5 molecules of the present invention are useful as targets for developing modulating agents to regulate a variety of cellular processes. Accordingly, in one aspect, this invention provides isolated nucleic acid molecules encoding TWIK proteins or biologically active portions thereof, as well as nucleic acid fragments suitable as primers or hybridization probes for the detection of TWIK-encoding nucleic acids.

In one embodiment, a TWIK nucleic acid molecule of the invention is at least 50%, 55%, 60%, 65%, 70%, 75%, 80%, 85%, 90%, 95%, 98%, 99% or more identical to the nucleotide sequence (e.g., to the entire length of the nucleotide sequence) shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:10, SEQ ID NO:12, or the nucleotide sequence of the DNA insert of the plasmid deposited with ATCC as Accession Number PTA-1640, or a complement thereof.

In a preferred embodiment, the isolated nucleic acid molecule includes the nucleotide sequence shown SEQ ID NO:1 or 3, or a complement thereof. In another embodiment, the nucleic acid molecule includes SEQ ID NO:3 and nucleotides 1-9 of SEQ ID NO:1. In yet another embodiment, the nucleic acid molecule includes SEQ ID NO:3 and nucleotides 1507-3452 of SEQ ID NO:1. In another preferred embodiment, the nucleic acid molecule has the nucleotide sequence shown in SEQ ID NO:1 or 3. In another preferred embodiment, the nucleic acid molecule includes a fragment of at least 1644 nucleotides of the nucleotide sequence of SEQ ID NO:1, SEQ ID NO:3, or a complement thereof.

In another preferred embodiment, the isolated nucleic acid molecule includes the nucleotide sequence shown SEQ ID NO:4 or 6, or a complement thereof. In another embodiment, the nucleic acid molecule includes SEQ ID NO:6 and nucleotides 1-121 of SEQ ID NO:4. In yet another embodiment, the nucleic acid molecule includes SEQ ID NO:6 and nucleotides 1118-1575 of SEQ ID NO:4. In another preferred embodiment, the nucleic acid molecule has the nucleotide sequence shown in SEQ ID NO:4 or 6. In another preferred embodiment, the nucleic acid molecule includes a fragment of at least 369 nucleotides of the nucleotide sequence of SEQ ID NO:4, SEQ ID NO:6, or a complement thereof.

In another preferred embodiment, the isolated nucleic acid molecule includes the nucleotide sequence shown SEQ ID NO:7 or 9, or a complement thereof. In another embodiment, the nucleic acid molecule includes SEQ ID NO:9 and nucleotides 1-135 of SEQ ID NO:7. In yet another embodiment, the nucleic acid molecule includes SEQ ID NO:9 and nucleotides 1075-2287 of SEQ ID NO:7. In another preferred embodiment, the nucleic acid molecule has the nucleotide sequence shown in SEQ ID NO:7 or 9. In another preferred embodiment, the nucleic acid molecule includes a fragment of at least 537 nucleotides of the nucleotide sequence of SEQ ID NO:7, SEQ ID NO:9, or a complement thereof.

In yet another preferred embodiment, the isolated nucleic acid molecule includes the nucleotide sequence shown SEQ ID NO:10 or 12, or a complement thereof. In another embodiment, the nucleic acid molecule includes SEQ ID NO:12 and nucleotides 1-156 of SEQ ID NO:10. In yet another embodiment, the nucleic acid molecule includes SEQ ID NO:12 and nucleotides 1361-1506 of SEQ ID NO:10. In another preferred embodiment, the nucleic acid molecule has the nucleotide sequence shown in SEQ ID NO:10 or 12.

In another embodiment, a TWIK nucleic acid molecule includes a nucleotide sequence encoding a protein having an amino acid sequence sufficiently identical to the amino acid sequence of SEQ ID NO: 2, SEQ ID NO:5, SEQ ID NO:8, SEQ ID NO:11, SEQ ID NO:11, or an amino acid sequence encoded by the DNA insert of the plasmid deposited with ATCC as Accession Number PTA-1640. In a preferred embodiment, a TWIK nucleic acid molecule includes a nucleotide sequence encoding a protein having an amino acid sequence at least 40%, 45%, 50%, 55%, 60%, 65%, 70%, 75%, 80%, 85%, 90%, 95% or more identical to the amino acid sequence of SEQ ID NO: 2, SEQ ID NO:5, SEQ ID NO:8, or SEQ ID NO:11, or the amino acid sequence encoded by the DNA insert of the plasmid deposited with ATCC as Accession Number PTA-1640.

In another preferred embodiment, an isolated nucleic acid molecule encodes the amino acid sequence of human TWIK-2, TWIK-3, TWIK-4, or TWIK-5. In yet another preferred embodiment, the nucleic acid molecule includes a nucleotide sequence encoding a protein having the amino acid sequence of SEQ ID NO: 2, SEQ ID NO:5, SEQ ID NO:8, SEQ ID NO:11, or SEQ ID NO:11, or the amino acid sequence encoded by the DNA insert of the plasmid deposited with ATCC as Accession Number PTA-1640. In yet another preferred embodiment, the nucleic acid molecule is at least 537 nucleotides in length and encodes a protein having a TWIK activity (as described herein).

Another embodiment of the invention features nucleic acid molecules, preferably TWIK nucleic acid molecules, which specifically detect TWIK nucleic acid molecules relative to nucleic acid molecules encoding non-TWIK proteins. For example, in one embodiment, such a nucleic acid molecule is at least 369, 400-450, 450-500, 500-550, 550-600, 600-650, 650-700, 700-750, 750-800 or more nucleotides in length and hybridizes under stringent conditions to a nucleic acid molecule comprising the nucleotide sequence shown in SEQ ID NO:4, the nucleotide sequence of the DNA insert of the plasmid deposited with ATCC as Accession Number PTA-1640, or a complement thereof. In preferred embodiments, the nucleic acid molecules are at least 15 (e.g., contiguous) nucleotides in length and hybridize under stringent conditions to nucleotides 1-397, 586-670, 904-1111, or 1573-1575 of SEQ ID NO:4. In other preferred embodiments, the nucleic acid molecules comprise nucleotides 1-397, 5 86-670, 904-1111, or 1573-1575 of SEQ ID NO:4.

In another particularly preferred embodiment, the nucleic acid molecule comprises a fragment of at least 537, 550-600, 600-650, 650-700, 700-750, 750-800 or more nucleotides in length and hybridizes under stringent conditions to a nucleic acid molecule comprising the nucleotide sequence shown in SEQ ID NO:7, the nucleotide sequence of the DNA insert of the plasmid deposited with ATCC as Accession Number PTA-1640, or a complement thereof. In preferred embodiments, the nucleic acid molecules are at least 15 (e.g., contiguous) nucleotides in length and hybridize under stringent conditions to nucleotides 1-164, 207-404, 1037-1789, 1818-1869, 1972-1985, or 2258-2287 of SEQ ID NO:7. In other preferred embodiments, the nucleic acid molecules include nucleotides 1-164, 207-404, 1037-1789, 1818-1869, 1972-1985, or 2258-2287 of SEQ ID NO:7.

In another particularly preferred embodiment, the nucleic acid molecule comprises a fragment of at least 550-600, 600-650, 650-700, 700-750, 750-800, 805, 850-900 or more nucleotides in length and hybridizes under stringent conditions to a nucleic acid molecule comprising the nucleotide sequence shown in SEQ ID NO:10, the nucleotide sequence of the DNA insert of the plasmid deposited with ATCC as Accession Number PTA-1640, or a complement thereof.

In other preferred embodiments, the nucleic acid molecule encodes a naturally occurring allelic variant of a polypeptide comprising the amino acid sequence of SEQ ID NO:2, 5, 8, 11, or an amino acid sequence encoded by the DNA insert of the plasmid deposited with ATCC as Accession Number PTA- 1640, wherein the nucleic acid molecule hybridizes to a nucleic acid molecule comprising SEQ ID NO:1, 3, 4, 6, 7, 9, 10, or 12 under stringent conditions.

Another embodiment of the invention provides an isolated nucleic acid molecule which is antisense to a TWIK nucleic acid molecule, e.g., the coding strand of a TWIK nucleic acid molecule.

Another aspect of the invention provides a vector comprising a TWIK nucleic acid molecule. In certain embodiments, the vector is a recombinant expression vector. In another embodiment, the invention provides a host cell containing a vector of the invention. The invention also provides a method for producing a protein, preferably a TWIK protein, by culturing in a suitable medium, a host cell, e.g., a mammalian host cell such as a non-human mammalian cell, of the invention containing a recombinant expression vector, such that the protein is produced.

Another aspect of this invention features isolated or recombinant TWIK proteins and polypeptides. In one embodiment, the isolated protein, preferably a TWIK protein, includes at least one transmembrane domain. In another embodiment, the isolated protein, preferably a TWIK protein, includes at least one P-loop. In another embodiment, the isolated protein, preferably a TWIK protein, includes at least one transmembrane domain and at least one P-loop. In a preferred embodiment, the protein, preferably a TWIK protein, includes at least one transmembrane domain and at least one P-loop and has an amino acid sequence at least about 50%, 55%, 60%, 65%, 70%, 75%, 80%, 85%, 90%, 95% or more identical to the amino acid sequence of SEQ ID NO: 2, SEQ ID NO:5, SEQ ID NO:8, SEQ ID NO:11 or the amino acid sequence encoded by the DNA insert of the plasmid deposited with ATCC as Accession Number PTA-1640. In another preferred embodiment, the protein, preferably a TWIK protein, includes at least one transmembrane domain and plays a role in generating an electrical potential across a plasma membrane, e.g., a neuronal plasma membrane or a muscle plasma membrane. In another preferred embodiment, the protein, preferably a TWIK protein, includes at least one P-loop and plays a role in generating an electrical potential across a plasma membrane, e.g., a neuronal plasma membrane or a muscle plasma membrane. In another preferred embodiment, the protein, preferably a TWIK protein, includes at least one transmembrane domain and at least one P-loop, and plays a role in generating an electrical potential across a plasma membrane, e.g., a neuronal plasma membrane or a muscle plasma membrane. In yet another preferred embodiment, the protein, preferably a TWIK protein, includes at least one transmembrane domain and at least one P-loop and is encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:10, or SEQ ID NO:12.

In another embodiment, the invention features fragments of the proteins having the amino acid sequence of SEQ ID NO: 2, SEQ ID NO:5, SEQ ID NO:8, or SEQ ID NO:11, wherein the fragment comprises at least 15 amino acids (e.g., contiguous amino acids) of the amino acid sequence of SEQ ID NO: 2, SEQ ID NO:5, SEQ ID NO:8, SEQ ID NO:11, or an amino acid sequence encoded by the DNA insert of the plasmid deposited with the ATCC as Accession Number PTA-1640 In another embodiment, the protein, preferably a TWIK protein, has the amino acid sequence of SEQ ID NO: 2, SEQ ID NO:5, SEQ ID NO:8, or SEQ ID NO: 11.

In another embodiment, the invention features an isolated protein, preferably a TWIK protein, which is encoded by a nucleic acid molecule having a nucleotide sequence at least about 50%, 55%, 60%, 65%, 70%, 75%, 80%, 85%, 90%, 95% or more identical to a nucleotide sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, or a complement thereof.

This invention further features an isolated protein, preferably a TWIK protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or a complement thereof.

The proteins of the present invention or biologically active portions thereof, can be operatively linked to a non-TWIK polypeptide (e.g., heterologous amino acid sequences) to form fusion proteins. The invention further features antibodies, such as monoclonal or polyclonal antibodies, that specifically bind proteins of the invention, preferably TWIK proteins. In addition, the TWIK proteins or biologically active portions thereof can be incorporated into pharmaceutical compositions, which optionally include pharmaceutically acceptable carriers.

In another aspect, the present invention provides a method for detecting the presence of a TWIK nucleic acid molecule, protein or polypeptide in a biological sample by contacting the biological sample with an agent capable of detecting a TWIK nucleic acid molecule, protein or polypeptide such that the presence of a TWIK nucleic acid molecule, protein or polypeptide is detected in the biological sample.

In another aspect, the present invention provides a method for detecting the presence of TWIK activity in a biological sample by contacting the biological sample with an agent capable of detecting an indicator of TWIK activity such that the presence of TWIK activity is detected in the biological sample.

In another aspect, the invention provides a method for modulating TWIK activity comprising contacting a cell capable of expressing TWIK with an agent that modulates TWIK activity such that TWIK activity in the cell is modulated. In one embodiment, the agent inhibits TWIK activity. In another embodiment, the agent stimulates TWIK activity. In one embodiment, the agent is an antibody that specifically binds to a TWIK protein. In another embodiment, the agent modulates expression of TWIK by modulating transcription of a TWIK gene or translation of a TWIK mRNA. In yet another embodiment, the agent is a nucleic acid molecule having a nucleotide sequence that is antisense to the coding strand of a TWIK mRNA or a TWIK gene.

In one embodiment, the methods of the present invention are used to treat a subject having a disorder characterized by aberrant TWIK protein or nucleic acid expression or activity by administering an agent which is a TWIK modulator to the subject. In one embodiment, the TWIK modulator is a TWIK protein. In another embodiment the TWIK modulator is a TWIK nucleic acid molecule. In yet another embodiment, the TWIK modulator is a peptide, peptidomimetic, or other small molecule. In a preferred embodiment, the disorder characterized by aberrant TWIK protein or nucleic acid expression is a CNS disorder.

The present invention also provides a diagnostic assay for identifying the presence or absence of a genetic alteration characterized by at least one of (i) aberrant modification or mutation of a gene encoding a TWIK protein; (ii) mis-regulation of the gene; and (iii) aberrant post-translational modification of a TWIK protein, wherein a wild-type form of the gene encodes a protein with a TWIK activity.

In another aspect the invention provides a method for identifying a compound that binds to or modulates the activity of a TWIK protein, by providing an indicator composition comprising a TWIK protein having TWIK activity, contacting the indicator composition with a test compound, and determining the effect of the test compound on TWIK activity in the indicator composition to identify a compound that modulates the activity of a TWIK protein.

Other features and advantages of the invention will be apparent from the following detailed description and claims.

BRIEF DESCRIPTION OF THE DRAWINGS

FIG. 1 depicts the cDNA sequence and predicted amino acid sequence of human TWIK-2. The nucleotide sequence corresponds to nucleic acids 1 to 3452 of SEQ ID NO:1. The amino acid sequence corresponds to amino acids 1 to 499 of SEQ ID NO:2. The coding region without the 5' and 3' untranslated regions of the human TWIK-2 gene is shown in SEQ ID NO:3.

FIG. 3 depicts the cDNA sequence and predicted amino acid sequence of human TWIK-3. The nucleotide sequence corresponds to nucleic acids 1 to 1575 of SEQ ID NO:4. The amino acid sequence corresponds to amino acids 1 to 332 of SEQ ID NO:5. The coding region without the 5' and 3' untranslated regions of the human TWIK-3 gene is shown in SEQ ID NO:6.

FIG. 5 depicts the cDNA sequence and predicted amino acid sequence of human TWIK-4. The nucleotide sequence corresponds to nucleic acids 1 to 2287 of SEQ ID NO:7. The amino acid sequence corresponds to amino acids 1 to 313 of SEQ ID NO:8. The coding region without the 5' and 3' untranslated regions of the human TWIK-4 gene is shown in SEQ ID NO:9.

FIG. 7 depicts a multiple sequence alignment of the amino acid sequence of human TWIK-4, human TWIK-1, murine TRAAK, murine TREK-1, human TWIK-3, human TWIK-2, and human TASK.

FIG. 8 depicts a multiple sequence alignment of the amino acid sequence of human TWIK-1, human TWIK-4, murine TRAAK, murine TREK-1, and human TASK.

FIG. 9 depicts a multiple sequence alignment of the amino acid sequence of human TWIK-3, human TASK2, human TWIK-1, and human TASK.

FIG. 10 depicts an alignment of the TWIK-2 protein with the TWIK-3 protein using the GAP program in the GCG software package (Blosum 62 matrix) and a gap weight of 12 and a length weight of 4.

FIG. 11 depicts an alignment of the TWIK-2 protein with the TWIK-4 protein using the GAP program in the GCG software package (Blosum 62 matrix) and a gap weight of 12 and a length weight of 4.

FIG. 12 depicts an alignment of the TWIK-3 protein with the TWIK-4 protein using the GAP program in the GCG software package (Blosum 62 matrix) and a gap weight of 12 and a length weight of 4.

FIG. 13 depicts an alignment of the TWIK-1 protein with the TWIK-2 protein using the GAP program in the GCG software package (Blosum 62 matrix) and a gap weight of 12 and a length weight of 4.

FIG. 14 depicts an alignment of the TWIK-1 protein with the TWIK-3 protein using the GAP program in the GCG software package (Blosum 62 matrix) and a gap weight of 12 and a length weight of 4.

FIG. 15 depicts an alignment of the TWIK-1 protein with the TWIK-4 protein using the GAP program in the GCG software package (Blosum 62 matrix) and a gap weight of 12 and a length weight of 4.

FIG. 16 depicts an alignment of the hTASK-2 protein with the TWIK-2 protein using the GAP program in the GCG software package (Blosum 62 matrix) and a gap weight of 12 and a length weight of 4.

FIG. 17 depicts the cDNA sequence and predicted amino acid sequence of human TWIK-5. The nucleotide sequence corresponds to nucleic acids 1 to 1506 of SEQ ID NO:10. The amino acid sequence corresponds to amino acids 1 to 401 of SEQ ID NO:11. The coding region without the 5' and 3' untranslated regions of the human TWIK-5 gene is shown in SEQ ID NO:12.

FIG. 19 depicts an alignment of the TWIK-5 protein with the hTASK-2 protein using the GAP program in the GCG software package (PAM250 matrix) and a gap weight of 25 and a length weight of 1.

FIG. 20 depicts an alignment of the TWIK-5 protein with the mouse TREK protein using the GAP program in the GCG software package (PAM250 matrix) and a gap weight of 25 and a length weight of 1.

DETAILED DESCRIPTION OF THE INVENTION

Figure 2:
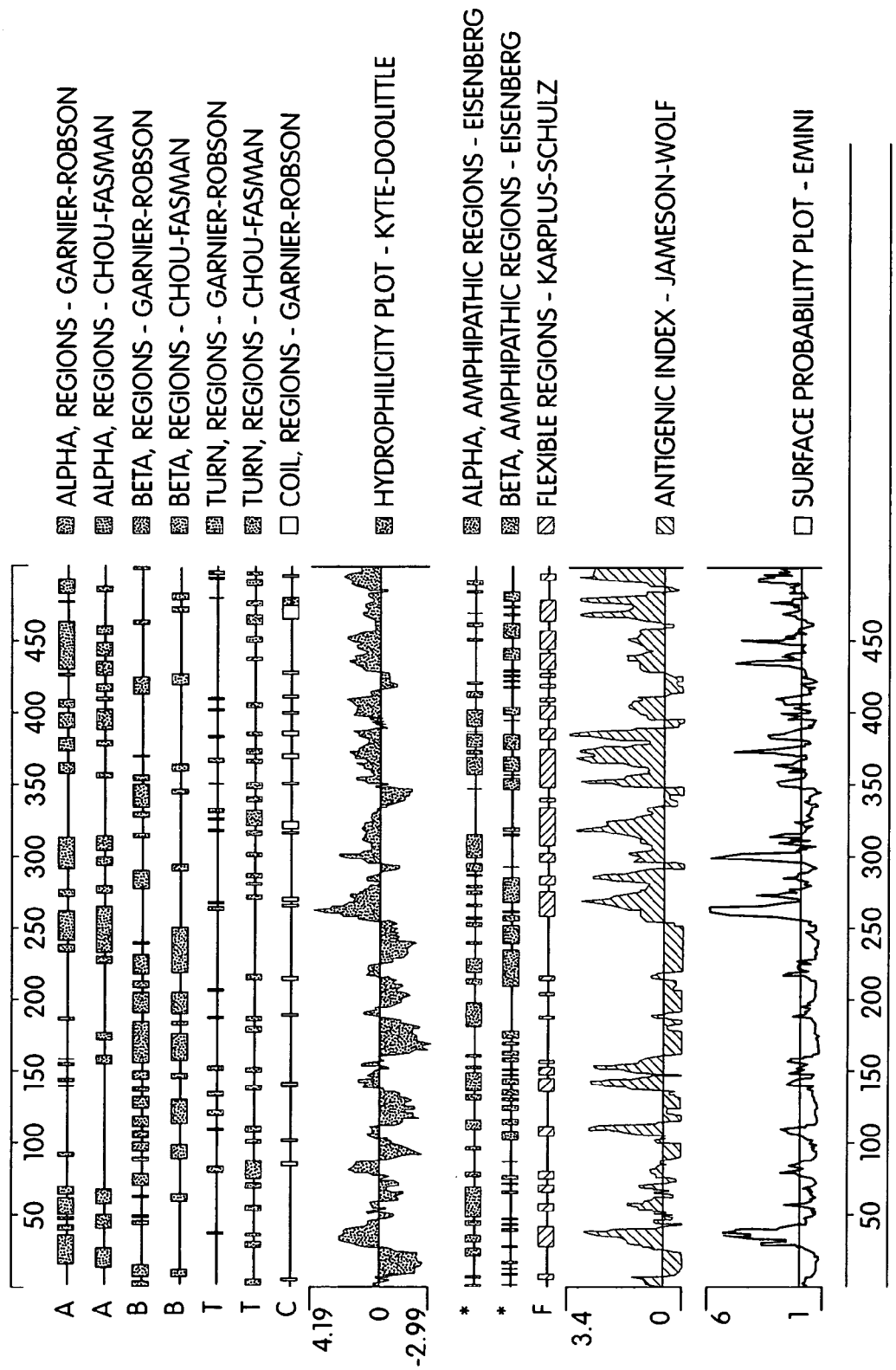
FIG. 2 depicts a structural, hydrophobicity, and antigenicity analysis of the human TWIK-2 protein.
Figure 4:
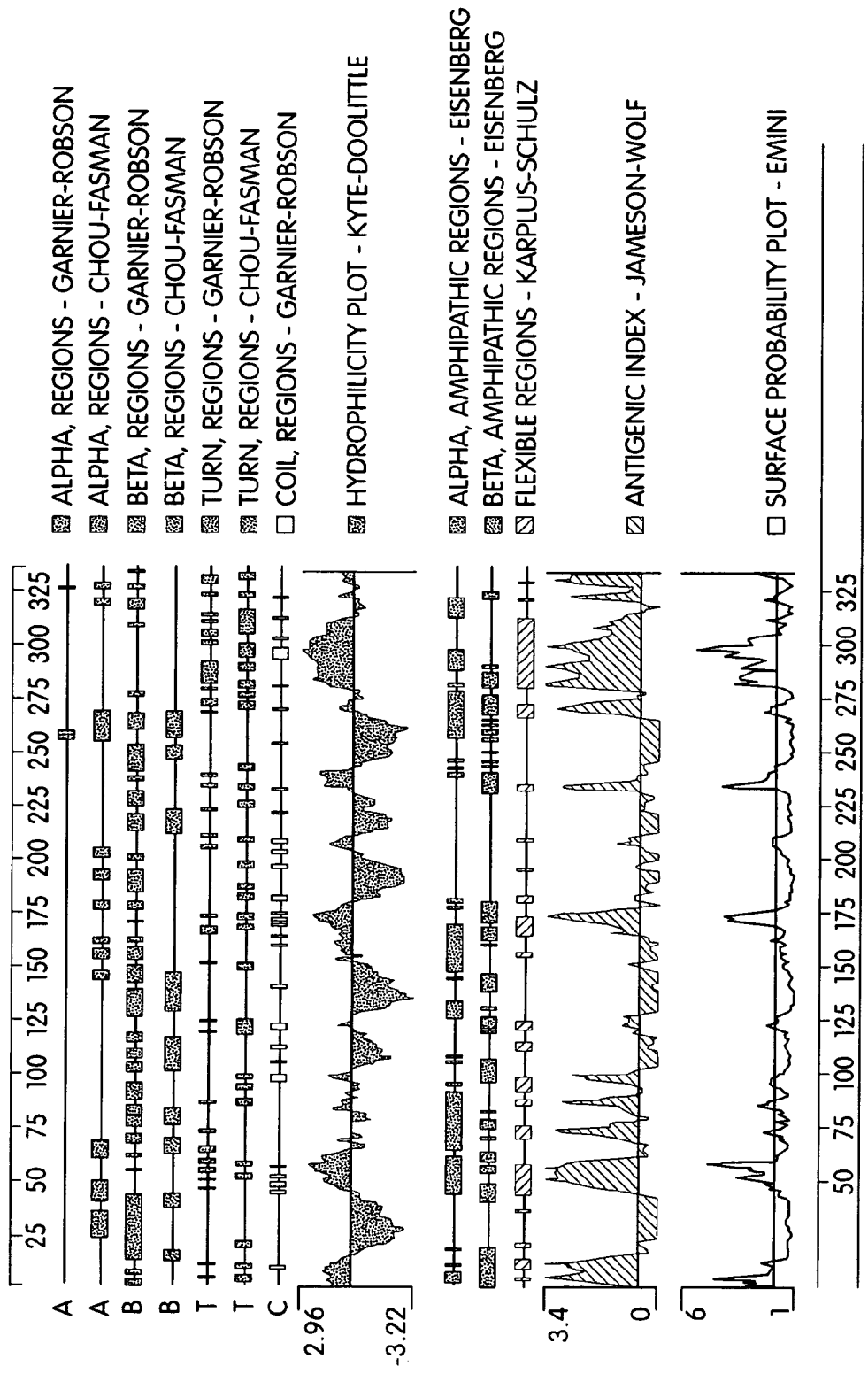
FIG. 4 depicts a structural, hydrophobicity, and antigenicity analysis of the human TWIK-3 protein.
Figure 6:
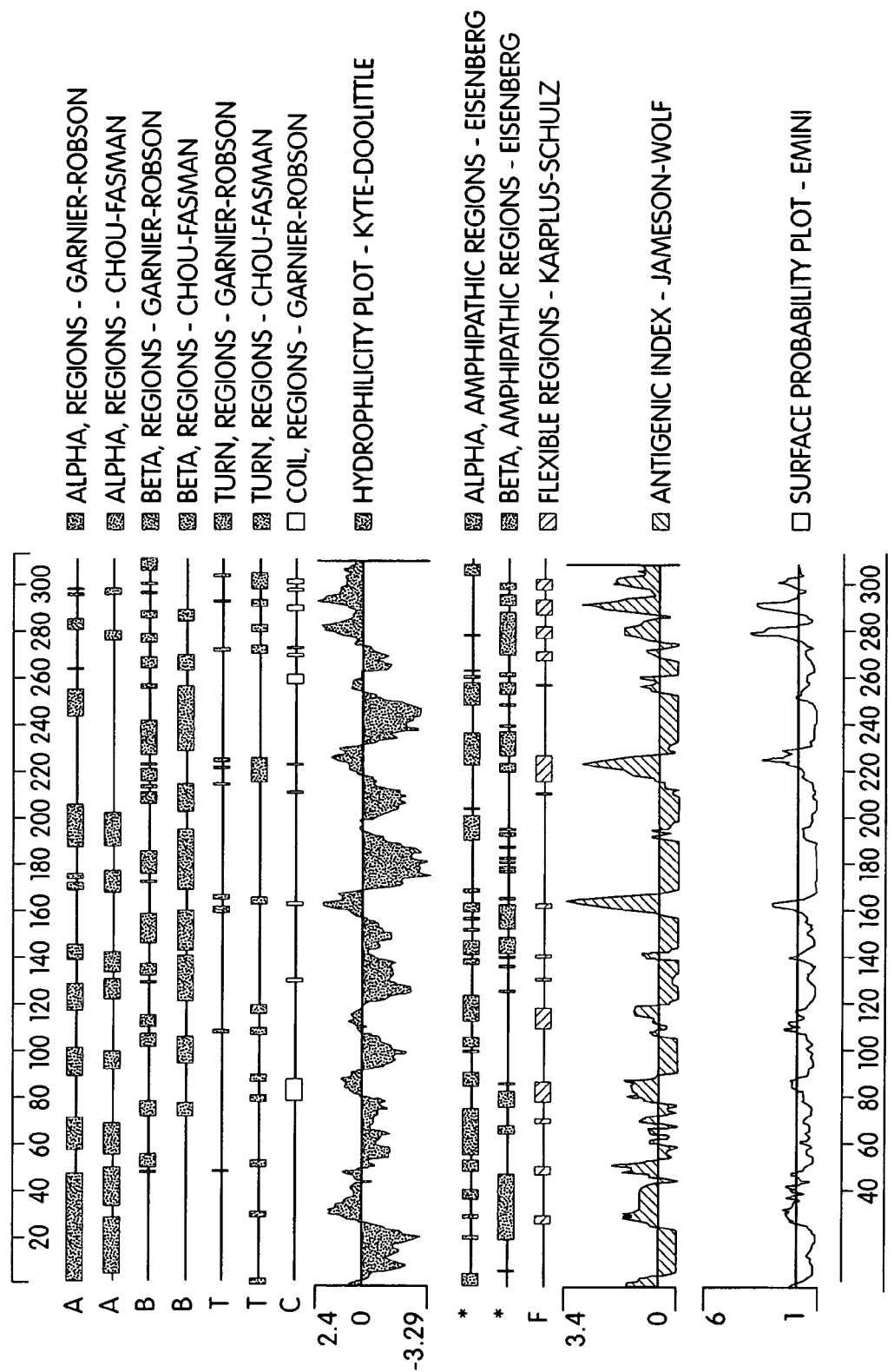
FIG. 6 depicts a structural, hydrophobicity, and antigenicity analysis of the human TWIK-4 protein.
Figure 18:
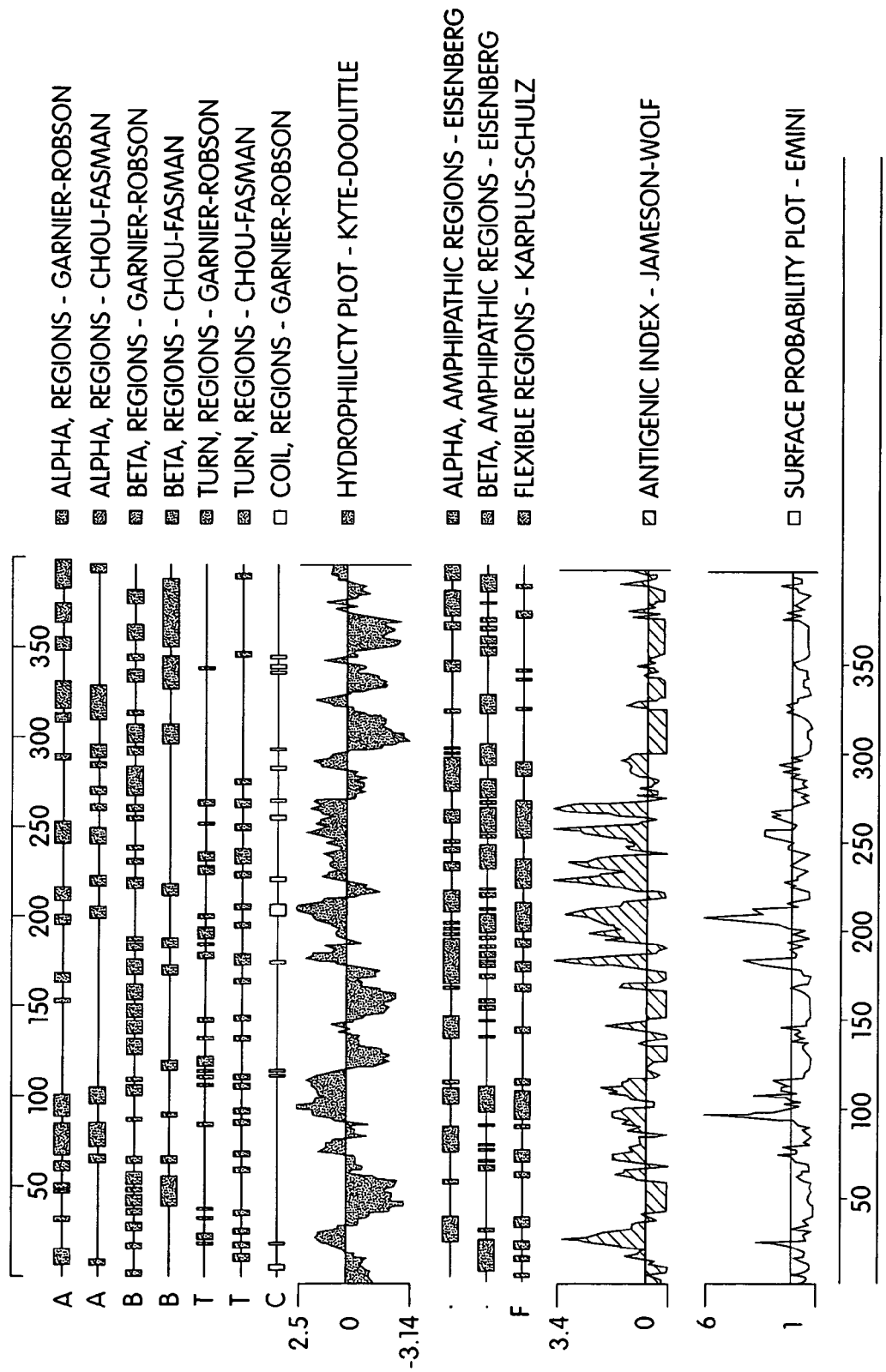
FIG. 18 depicts a structural, hydrophobicity, and antigenicity analysis of the human TWIK-5 protein.

The present invention is based, at least in part, on the discovery of novel molecules, referred to herein as TWIK-2, TWIK-3, TWIK-4, and TWIK-5 nucleic acid and protein molecules, which are novel members of the TWIK (for Tandem of P domains in a Weak Inward rectifying $K^+$ channel) family of potassium channels. These novel molecules are capable of, for example, modulating a potassium channel mediated activity in a cell, e.g., a neuronal cell or a muscle cell.

As used herein, a "potassium channel" includes a protein or polypeptide which is involved in receiving, conducting, and transmitting signals, in an electrically excitable cell, e.g., a neuronal cell or a muscle cell. Potassium channels are potassium ion selective, and can determine membrane excitability (the ability of, for example, a neuron to respond to a stimulus and convert it into an impulse). Potassium channels can also influence the resting potential of membranes, wave forms and frequencies of action potentials, and thresholds of excitation. Potassium channels are typically expressed in electrically excitable cells, e.g., neurons, muscle, endocrine, and egg cells, and may form heteromultimeric structures, e.g., composed of pore-forming α and cytoplasmic β subunits. Examples of potassium channels include: (1) the voltage-gated potassium channels, (2) the ligand-gated potassium channels, e.g., cyclic nucleotide-gated potassium channels, and (3) the mechanically-gated potassium channels. Voltage-gated and ligand-gated potassium channels are expressed in the brain, e.g., in brainstem monoaminergic and forebrain cholinergic neurons, where they are involved in the release of neurotransmitters, or in the dendrites of hippocampal and neocortical pyramidal cells, where they are involved in the processes of learning and memory formation. For a detailed description of potassium channels, see Kandel E. R.. et al., Principles of Neural Science, second edition, (Elsevier Science Publishing Co., Inc., N.Y. (1985)), the contents of which are incorporated herein by reference. As the TWIK proteins of the present invention may modulate potassium channel mediated activities, they may be useful for developing novel diagnostic and therapeutic agents for potassium channel associated disorders.

As used herein, a "potassium channel associated disorder" includes a disorder, disease or condition which is characterized by a misregulation of a potassium channel mediated activity. Potassium channel associated disorders can detrimentally affect conveyance of sensory impulses from the periphery to the brain and/or conductance of motor impulses from the brain to the periphery; integration of reflexes; interpretation of sensory impulses; and emotional, intellectual (e.g., learning and memory), or motor processes. Examples of potassium channel associated disorders include CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, korsakoff's psychosis, mania, anxiety disorders, or phobic disorders; learning or memory disorders, e.g., amnesia or age-related memory loss; and neurological disorders, e.g., migraine. Further examples of potassium channel associated disorders include obesity; cardiac disorders, e.g., cardiac arrhythmias; and pain disorders, e.g., pain disorders associated with various forms of tissue injury, such as inflammation, infection, and ischemia, usually referred to as hyperalgesia (described in, for example, Fields, H. L. (1987) *Pain*, New York:McGraw-Hill), tooth pain, headaches (e.g., tension headache or migraine), back pain, cancer pain, arthritis pain, psychogenic pain, pain associated with surgery, or neuropathic pain.

As used herein, a "potassium channel mediated activity" includes an activity which involves a potassium channel, e.g., a potassium channel in a neuronal cell or a muscle cell, associated with receiving, conducting, and transmitting signals in, for example, the nervous system. Potassium channel mediated activities include release of neurotransmitters, e.g., dopamine or norepinephrine, from cells, e.g., neuronal cells; modulation of resting potential of membranes, wave forms and frequencies of action potentials, and thresholds of excitation; and modulation of processes such as integration of sub-threshold synaptic responses and the conductance of back-propagating action potentials in, for example, neuronal cells or muscle cells.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

For example, the family of TWIK proteins comprise at least one "transmembrane domain" and preferably four transmembrane domains. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al. (1996) *Annu. Rev. Neurosci.* 19: 235-63, the contents of which are incorporated herein by reference. Amino acid residues 7-23, 113-134, 160-184, and 225-242 of the human TWIK-2 protein, amino acid residues 23-43, 131-148, 178-200, and 244-264 of the human TWIK-3 protein, amino acid residues 7-26, 121-140, 169-193, and 236-253 of the human TWIK-4 protein comprise transmembrane domains, and amino acid residues 37-61, 148-165, 298-321, and 353-372 of the human TWIK-5 protein comprise transmembrane domains.

In another embodiment, a TWIK molecule of the present invention is identified based on the presence of a P-loop. As used herein, the term "P-loop" (also known as an H5 domain) includes an amino acid sequence of about 15-45 amino acid residues in length, preferably about 15-35 amino acid residues in length, and most preferably about 15-25 amino acid residues in length, which is involved in lining the potassium channel pore. A P-loop is typically found between transmembrane domains of potassium channels and is believed to be a major determinant of ion selectivity in potassium channels. Preferably, P-loops contain a G-[HYDROPHOBIC AMINO ACID]-G sequence, e.g., a GYG, GLG, or GFG sequence. P-loops are described in, for example, Warmke et al. (1991) *Science* 252:1560-1562; Zagotta W. N. et al., (1996) *Annu. Rev. Neurosci.* 19:235-63 Pongs, O. (1993) *J. Membr. Biol.*, 136, 1-8; Heginbotham et al. (1994) *Biophys. J.* 66,1061-1067; Mackinnon, R. (1995) *Neuron*, 14, 889-892; Pascual et al., (1995) *Neuron.*, 14, 1055-1063, the contents of which are incorporated herein by reference. Amino acid residues 88-105 and 194-213 of the human TWIK-2 protein, amino acid residues 103-119 and 212-229 of the human TWIK-3 protein, amino acid residues 93-109 and 204-22 1 of the human TWIK-4 protein comprise a P-loop, and amino acid residues 118-139 and 328-345 of the human TWIK-5 protein comprise a P-loop.

In a preferred embodiment, the TWIK molecules of the invention include an intracellular amino- and carboxyl-terminus, four transmembrane domains, and two P-loops. The P-loops are preferably located between transmembrane domains 1 and 2, and 3 and 4. The TWIK molecules of the present invention can further include a cysteine residue between the first transmembrane domain and the first P-loop, which may be involved in the formation of a TWIK dimer (through a disulfide bridge). For example, TWIK-2 contains such a cysteine residue at position 51, TWIK-3 contains such a cysteine residue at position 68, TWIK-4 contains such a cysteine residue at position 53, and TWIK-5 contains such a cysteine residue at position 83.

Isolated proteins of the present invention, preferably TWIK-2, TWIK-3, TWIK-4, and TWIK-5 proteins, have an amino acid sequence sufficiently identical to the amino acid sequence of SEQ ID NO: 2, SEQ ID NO:5, SEQ ID NO:8, SEQ ID NO:11 or are encoded by a nucleotide sequence sufficiently identical to SEQ ID NO:1, SEQ ID NO:3, SEQ ID NO:4, SEQ ID NO:6, SEQ ID NO:7, SEQ ID NO:9, SEQ ID NO:10, or SEQ ID NO:12. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90-95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% homology and share a common functional activity are defined herein as sufficiently identical.

As used interchangeably herein, a "TWIK activity", "biological activity of TWIK" or "functional activity of TWIK", refers to an activity exerted by a TWIK protein, polypeptide or nucleic acid molecule on a TWIK responsive cell or on a TWIK protein substrate, as determined in vivo, or in vitro, according to standard techniques. In one embodiment, a TWIK activity is a direct activity, such as an association with a TWIK-target molecule. As used herein, a "target molecule" or "binding partner" is a molecule with which a TWIK protein binds or interacts in nature, such that TWIK-mediated function is achieved. A TWIK target molecule can be a non-TWIK molecule or a TWIK protein or polypeptide of the present invention. In an exemplary embodiment, a TWIK target molecule is a TWIK ligand. Alternatively, a TWIK activity is an indirect activity, such as a cellular signaling activity mediated by interaction of the TWIK protein with a TWIK ligand. The biological activities of TWIK are described herein. For example, the TWIK proteins of the present invention can have one or more of the following activities: (1) modulate the release of neurotransmitters, (2) modulate membrane excitability, (3) influence the resting potential of membranes, (4) modulate wave forms and frequencies of action potentials, (5) modulate thresholds of excitation, and (6) modulate processes which underlie learning and memory, such as integration of sub-threshold synaptic responses and the conductance of back-propagating action potentials.

Accordingly, another embodiment of the invention features isolated TWIK proteins and polypeptides having a TWIK activity. Preferred proteins are TWIK proteins having at least one transmembrane domain, at least one P-loop and, preferably, a TWIK activity. Other preferred proteins are TWIK proteins having at least one transmembrane domain and, preferably, a TWIK activity. Other preferred proteins are TWIK proteins having at least one P-loop, and, preferably, a TWIK activity. Other preferred proteins are TWIK proteins having at least one transmembrane domain, at least one P-loop, and are, preferably, encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12.

The nucleotide sequence of the isolated human TWIK-2 cDNA and the predicted amino acid sequence of the human TWIK-2 polypeptide are shown in FIG. 1 and in SEQ ID NOs:1 and 2, respectively.

The human TWIK-2 gene, which is approximately 3452 nucleotides in length, encodes a protein having a molecular weight of approximately 57.4 kD and which is approximately 499 amino acid residues in length.

The nucleotide sequence of the isolated human TWIK-3 cDNA and the predicted amino acid sequence of the human TWIK-3 polypeptide are shown in FIG. 3 and in SEQ ID NOs:4 and 5, respectively.

The human TWIK-3 gene, which is approximately 1575 nucleotides in length, encodes a protein having a molecular weight of approximately 38.2 kD and which is approximately 332 amino acid residues in length.

The nucleotide sequence of the isolated human TWIK-4 cDNA and the predicted amino acid sequence of the human TWIK-4 polypeptide are shown in FIG. 5 and in SEQ ID NOs:7 and 9, respectively.

The human TWIK-4 gene, which is approximately 2287 nucleotides in length, encodes a protein having a molecular weight of approximately 36 kD and which is approximately 313 amino acid residues in length.

The nucleotide sequence of the isolated human TWIK-5 cDNA and the predicted amino acid sequence of the human TWIK-5 polypeptide are shown in FIG. 17 and in SEQ ID NOs:10 and 11, respectively. A plasmid containing the nucleotide sequence encoding human TWIK-5 was deposited with American Type Culture Collection (ATCC). 10801 University Boulevard, Manassas. Va. 20110-2209. on Apr. 5, 2000 and assigned Accession Number PTA-1640. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The human TWIK-5 gene, which is approximately 1506 nucleotides in length, encodes a protein having a molecular weight of approximately 46.1 kD and which is approximately 401 amino acid residues in length.

Various aspects of the invention are described in further detail in the following subsections:

I. Isolated Nucleic Acid Molecules

One aspect of the invention pertains to isolated nucleic acid molecules that encode TWIK proteins or biologically active portions thereof, as well as nucleic acid fragments sufficient for use as hybridization probes to identify TWIK-encoding nucleic acid molecules (e.g., TWIK mRNA) and fragments for use as PCR primers for the amplification or mutation of TWIK nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated TWIK nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, or a portion thereof, can be isolated using standard molecular biology techniques and the sequence information provided herein. Using all or portion of the nucleic acid sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, as a hybridization probe, TWIK nucleic acid molecules can be isolated using standard hybridization and cloning techniques (e.g., as described in Sambrook, J., Fritsh, E. F., and Maniatis, T. *Molecular Cloning. A Laboratory Manual. 2nd, ed., Cold Spring Harbor Laboratory,* Cold Spring Harbor Laboratory Press, Cold Spring Harbor, N.Y., 1989).

Moreover, a nucleic acid molecule encompassing all or a portion of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640 can be isolated by the polymerase chain reaction (PCR) using synthetic oligonucleotide primers designed based upon the sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to TWIK nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human TWIK-2 cDNA. This cDNA comprises sequences encoding the human TWIK-2 protein (i.e., "the coding region", from nucleotides 10-1506), as well as 5' untranslated sequences (nucleotides 1-9) and 3' untranslated sequences (nucleotides 1507-3452). Alternatively, the nucleic acid molecule can comprise only the coding region of SEQ ID NO:1 (e.g., nucleotides 10-1506, corresponding to SEQ ID NO:3).

In another preferred embodiment, an isolated nucleic acid molecule of the invention comprises the nucleotide sequence shown in SEQ ID NO:4. The sequence of SEQ ID NO:4 corresponds to the human TWIK-3 cDNA. This cDNA comprises sequences encoding the human TWIK-3 protein (i.e., "the coding region", from nucleotides 122-1117), as well as 5' untranslated sequences (nucleotides 1-121) and 3' untranslated sequences (nucleotides 1118-1575). Alternatively, the nucleic acid molecule can comprise only the coding region of SEQ ID NO:4 (e.g., nucleotides 122-1117, corresponding to SEQ ID NO:6).

In yet another preferred embodiment, an isolated nucleic acid molecule of the invention comprises the nucleotide sequence shown in SEQ ID NO:7. The sequence of SEQ ID NO:7 corresponds to the human TWIK-4 cDNA. This cDNA comprises sequences encoding the human TWIK-4 protein (i.e., "the coding region", from nucleotides 136-1074), as well as 5' untranslated sequences (nucleotides 1-135) and 3' untranslated sequences (nucleotides 1075-2287). Alternatively, the nucleic acid molecule can comprise only the coding region of SEQ ID NO:7 (e.g., nucleotides 136-1074, corresponding to SEQ ID NO:9).

In a preferred embodiment, an isolated nucleic acid molecule of the invention comprises the nucleotide sequence shown in SEQ ID NO:10. The sequence of SEQ ID NO:10 corresponds to the human TWIK-5 cDNA. This cDNA comprises sequences encoding the human TWIK-5 protein (i.e., "the coding region", from nucleotides 157-1359), as well as 5' untranslated sequences (nucleotides 1-156) and 3' untranslated sequences (nucleotides 1360-1506). Alternatively, the nucleic acid molecule can comprise only the coding region of SEQ ID NO:10 (e.g., nucleotides 157-1359, corresponding to SEQ ID NO:12).

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, or a portion of any of these nucleotide sequences. A nucleic acid molecule which is complementary to the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, is one which is sufficiently complementary to the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, such that it can hybridize to the nucleotide sequence shown in SEQ ID NO:10, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95% or more identical to the entire length of the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the entire length of the nucleotide sequence of the DNA insert of the plasmid deposited with ATCC as Accession Number PTA-1640, or a portion of any of these nucleotide sequences.

Moreover, the nucleic acid molecule of the invention can comprise only a portion of the nucleic acid sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, for example a fragment which can be used as a probe or primer or a fragment encoding a biologically active portion of a TWIK protein. The nucleotide sequence determined from the cloning of the TWIK gene allows for the generation of probes and primers designed for use in identifying and/or cloning other TWIK family members, as well as TWIK homologues from other species.

The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, of an anti-sense sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, or of a naturally occurring allelic variant or mutant of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640. In an exemplary embodiment, a nucleic acid molecule of the present invention comprises a nucleotide sequence which is 369, 350-400, 400-450, 450-500, 500-550, 537, 550-600, 600-650, 650-700, 700-750, 750-800, 800-850, 850-900, 949, 950-1000, 1575, 2287, or 3452 nucleotides in length and hybridizes under stringent hybridization conditions to a nucleic acid molecule of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640.

Probes based on the TWIK nucleotide sequences can be used to detect transcripts or genomic sequences encoding the same or identical proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a TWIK protein, such as by measuring a level of a TWIK-encoding nucleic acid in a sample of cells from a subject e.g., detecting TWIK mRNA levels or determining whether a genomic TWIK gene has been mutated or deleted.

A nucleic acid fragment encoding a "biologically active portion of a TWIK protein" can be prepared by isolating a portion of the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, which encodes a polypeptide having a TWIK biological activity (the biological activities of the TWIK proteins are described herein), expressing the encoded portion of the TWIK protein (e.g., by recombinant expression in vitro) and assessing the activity of the encoded portion of the TWIK protein.

The invention further encompasses nucleic acid molecules that differ from the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12 or the nucleotide sequence of the DNA insert of the plasmid deposited with ATCC as Accession Number PTA-1640, due to degeneracy of the genetic code and thus encode the same TWIK proteins as those encoded by the nucleotide sequence shown in SEQ ID NO:1, SEQ ID NO:3, SEQ ID NO:4, SEQ ID NO:6, SEQ ID NO:7, SEQ ID NO:9, SEQ ID NO: 10, SEQ ID NO: 12 or the nucleotide sequence of the DNA insert of the plasmid deposited with ATCC as Accession Number PTA-1640. In another embodiment, an isolated nucleic acid molecule of the invention has a nucleotide sequence encoding a protein having an amino acid sequence shown in SEQ ID NO: 2, SEQ ID NO:5, SEQ ID NO:8, or SEQ ID NO:11.

In addition to the TWIK nucleotide sequences shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, it will be appreciated by those skilled in the art that DNA sequence polymorphisms that lead to changes in the amino acid sequences of the TWIK proteins may exist within a population (e.g., the human population). Such genetic polymorphism in the TWIK genes may exist among individuals within a population due to natural allelic variation. As used herein, the terms "gene" and "recombinant gene" refer to nucleic acid molecules which include an open reading frame encoding a TWIK protein, preferably a mammalian TWIK protein, and can further include non-coding regulatory sequences, and introns.

Allelic variants of human TWIK include both functional and non-functional TWIK proteins. Functional allelic variants are naturally occurring amino acid sequence variants of the human TWIK protein that maintain the ability to bind a TWIK ligand and/or modulate any of the TWIK activities described herein. Functional allelic variants will typically contain only conservative substitution of one or more amino acids of SEQ ID NO: 2, SEQ ID NO:5, SEQ ID NO:8, or SEQ ID NO:11 or substitution, deletion or insertion of non-critical residues in non-critical regions of the protein.

Non-functional allelic variants are naturally occurring amino acid sequence variants of the human TWIK protein that do not have the ability to either bind a TWIK ligand and/or modulate any of the TWIK activities described herein. Non-functional allelic variants will typically contain a non-conservative substitution, a deletion, or insertion or premature truncation of the amino acid sequence of SEQ ID NO: 2, SEQ ID NO:5, SEQ ID NO:8, or SEQ ID NO:11 or a substitution, insertion or deletion in critical residues or critical regions.

The present invention further provides non-human orthologues of the human TWIK protein. Orthologues of the human TWIK protein are proteins that are isolated from non-human organisms and possess the same TWIK ligand binding and/or potassium channel mediated activities of the human TWIK protein. Orthologues of the human TWIK protein can readily be identified as comprising an amino acid sequence that is substantially identical to SEQ ID NO: 2, SEQ ID NO:5, SEQ ID NO:8, or SEQ ID NO:11.

Moreover, nucleic acid molecules encoding other TWIK family members and, thus, which have a nucleotide sequence which differs from the TWIK sequences of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640 are intended to be within the scope of the invention. For example, another TWIK cDNA can be identified based on the nucleotide sequence of human TWIK. Moreover, nucleic acid molecules encoding TWIK proteins from different species, and thus which have a nucleotide sequence which differs from the TWIK sequences of SEQ ID NO:1, SEQ ID NO:3, SEQ ID NO:4, SEQ ID NO:6, SEQ ID NO:7, SEQ ID NO:9, SEQ ID NO:10, SEQ ID NO:12 or the nucleotide sequence of the DNA insert of the plasmid deposited with ATCC as Accession Number PTA-1640 are intended to be within the scope of the invention. For example, a mouse TWIK cDNA can be identified based on the nucleotide sequence of a human TWIK.

Nucleic acid molecules corresponding to natural allelic variants and homologues of the TWIK cDNAs of the invention can be isolated based on their homology to the TWIK nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12 or the nucleotide sequence of the DNA insert of the plasmid deposited with ATCC as Accession Number PTA-1640. In other embodiment, the nucleic acid is at least 30, 50, 100, 150, 200, 250, 300, 307, 350, 400, 450, 500, 550, 600, 650, 700, 750, 800, 850, 900, 949, or 950 nucleotides in length. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2× SSC, 0.1% SDS at 50° C., preferably at 55° C., and more preferably at 60° C. or 65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the TWIK sequences that may exist in the population, the skilled artisan will further appreciate that changes can be introduced by mutation into the nucleotide sequences of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, thereby leading to changes in the amino acid sequence of the encoded TWIK proteins, without altering the functional ability of the TWIK proteins. For example, nucleotide substitutions leading to amino acid substitutions at "non-essential" amino acid residues can be made in the sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640. A "non-essential" amino acid residue is a residue that can be altered from the wild-type sequence of TWIK (e.g., the sequence of SEQ ID NO:2) without altering the biological activity, whereas an "essential" amino acid residue is required for biological activity. For example, amino acid residues that are conserved among the TWIK proteins of the present invention, are predicted to be particularly unamenable to alteration. Furthermore, additional amino acid residues that are conserved between the TWIK proteins of the present invention and other members of the TWIK potassium channel families are not likely to be amenable to alteration.

Accordingly, another aspect of the invention pertains to nucleic acid molecules encoding TWIK proteins that contain changes in amino acid residues that are not essential for activity. Such TWIK proteins differ in amino acid sequence from SEQ ID NO: 2, SEQ ID NO:5, SEQ ID NO:8, or SEQ ID NO:11, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95% or more identical to SEQ ID NO: 2, SEQ ID NO:5, SEQ ID NO:8, or SEQ ID NO:11.

An isolated nucleic acid molecule encoding a TWIK protein identical to the protein of SEQ ID NO: 2, SEQ ID NO:5, SEQ ID NO:8, or SEQ ID NO:11 can be created by introducing one or more nucleotide substitutions, additions or deletions into the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, such that one or more amino acid substitutions, additions or deletions are introduced into the encoded protein. Mutations can be introduced into SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, seine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a TWIK protein is preferably replaced with another amino acid residue from the same side chain family. Alternatively, in another embodiment, mutations can be introduced randomly along all or part of a TWIK coding sequence, such as by saturation mutagenesis, and the resultant mutants can be screened for TWIK biological activity to identify mutants that retain activity. Following mutagenesis of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640, the encoded protein can be expressed recombinantly and the activity of the protein can be determined.

In a preferred embodiment, a mutant TWIK protein can be assayed for the ability to (1) interact with a non-TWIK protein molecule; (2) activate a TWIK-dependent signal transduction pathway; (3) modulate the release of neurotransmitters, (4) modulate membrane excitability, (5) influence the resting potential of membranes, wave forms and frequencies of action potentials, and thresholds of excitation, and (6) modulate processes which underlie learning and memory, such as integration of sub-threshold synaptic responses and the conductance of back-propagating action potentials.

In addition to the nucleic acid molecules encoding TWIK proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire TWIK coding strand, or to only a portion thereof. In one embodiment, an antisense nucleic acid molecule is antisense to a "coding region" of the coding strand of a nucleotide sequence encoding TWIK. The term "coding region" refers to the region of the nucleotide sequence comprising codons which are translated into amino acid residues (e.g., the coding region of human TWIK-2 corresponds to SEQ ID NO:3). In another embodiment, the antisense nucleic acid molecule is antisense to a "noncoding region" of the coding strand of a nucleotide sequence encoding TWIK. The term "noncoding region" refers to 5' and 3' sequences which flank the coding region that are not translated into amino acids (i.e., also referred to as 5' and 3' untranslated regions).

Given the coding strand sequences encoding TWIK disclosed herein (e.g., SEQ ID NO:3, SEQ ID NO:6, SEQ ID NO:9, and SEQ ID NO:12), antisense nucleic acids of the invention can be designed according to the rules of Watson and Crick base pairing. The antisense nucleic acid molecule can be complementary to the entire coding region of TWIK mRNA, but more preferably is an oligonucleotide which is antisense to only a portion of the coding or noncoding region of TWIK mRNA. For example, the antisense oligonucleotide can be complementary to the region surrounding the translation start site of TWIK mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a TWIK protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585-591)) can be used to catalytically cleave TWIK mRNA transcripts to thereby inhibit translation of TWIK mRNA. A ribozyme having specificity for a TWIK-encoding nucleic acid can be designed based upon the nucleotide sequence of a TWIK cDNA disclosed herein (i.e., SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the nucleotide sequence of the DNA insert of the plasmid deposited with ATCC as Accession Number PTA-1640). For example, a derivative of a Tetrahymena L-19 IVS RNA can be constructed in which the nucleotide sequence of the active site is complementary to the nucleotide sequence to be cleaved in a TWIK-encoding mRNA. See, e.g., Cech et al. U.S. Pat. No. 4,987,071; and Cech et al. U.S. Pat. No. 5,116, 742. Alternatively, TWIK mRNA can be used to select a catalytic RNA having a specific ribonuclease activity from a pool of RNA molecules. See, e.g., Bartel, D. and Szostak, J. W. (1993) Science 261:1411-1418.

Alternatively, TWIK gene expression can be inhibited by targeting nucleotide sequences complementary to the regulatory region of the TWIK (e.g., the TWIK promoter and/or enhancers) to form triple helical structures that prevent transcription of the TWIK gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

In yet another embodiment, the TWIK nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670-675.

PNAs of TWIK nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of TWIK nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of TWIK can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of TWIK nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

II. Isolated TWIK Proteins and Anti-TWIK Antibodies

One aspect of the invention pertains to isolated TWIK proteins, and biologically active portions thereof, as well as polypeptide fragments suitable for use as immunogens to raise anti-TWIK antibodies. In one embodiment, native TWIK proteins can be isolated from cells or tissue sources by an appropriate purification scheme using standard protein purification techniques. In another embodiment, TWIK proteins are produced by recombinant DNA techniques. Alternative to recombinant expression, a TWIK protein or polypeptide can be synthesized chemically using standard peptide synthesis techniques.

An "isolated" or "purified" protein or biologically active portion thereof is substantially free of cellular material or other contaminating proteins from the cell or tissue source from which the TWIK protein is derived, or substantially free from chemical precursors or other chemicals when chemically synthesized. The language "substantially free of cellular material" includes preparations of TWIK protein in which the protein is separated from cellular components of the cells from which it is isolated or recombinantly produced. In one embodiment, the language "substantially free of cellular material" includes preparations of TWIK protein having less than about 30% (by dry weight) of non-TWIK protein (also referred to herein as a "contaminating protein"), more preferably less than about 20% of non-TWIK protein, still more preferably less than about 10% of non-TWIK protein, and most preferably less than about 5% non-TWIK protein. When the TWIK protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of TWIK protein in which the protein is separated from chemical precursors or other chemicals which are involved in the synthesis of the protein. In one embodiment, the language "substantially free of chemical precursors or other chemicals" includes preparations of TWIK protein having less than about 30% (by dry weight) of chemical precursors or non-TWIK chemicals, more preferably less than about 20% chemical precursors or non-TWIK chemicals, still more preferably less than about 10% chemical precursors or non-TWIK chemicals, and most preferably less than about 5% chemical precursors or non-TWIK chemicals.

As used herein, a "biologically active portion" of a TWIK protein includes a fragment of a TWIK protein which participates in an interaction between a TWIK molecule and a non-TWIK molecule. Biologically active portions of a TWIK protein include peptides comprising amino acid sequences sufficiently identical to or derived from the amino acid sequence of the TWIK protein, e.g., the amino acid sequence shown in SEQ ID NO: 2, SEQ ID NO:5, SEQ ID NO:8, or SEQ ID NO:11, which include less amino acids than the full length TWIK proteins, and exhibit at least one activity of a TWIK protein. Typically, biologically active portions comprise a domain or motif with at least one activity of the TWIK protein, e.g., binding of a cyclic nucleotide. A biologically active portion of a TWIK protein can be a polypeptide which is, for example, 10, 25, 50, 100, 200, 313, 332, or 499 amino acids in length. Biologically active portions of a TWIK protein can be used as targets for developing agents which modulate a potassium channel mediated activity.

In one embodiment, a biologically active portion of a TWIK protein comprises at least one transmembrane domain. In another embodiment, a biologically active portion of a TWIK protein comprises at least one P-loop. In yet another embodiment a biologically active portion of a TWIK protein comprises at least one transmembrane domain and at least one P-loop.

It is to be understood that a preferred biologically active portion of a TWIK protein of the present invention may contain at least one of the above-identified structural domains. A more preferred biologically active portion of a TWIK protein may contain at least two of the above-identified structural domains. Moreover, other biologically active portions, in which other regions of the protein are deleted, can be prepared by recombinant techniques and evaluated for one or more of the functional activities of a native TWIK protein.

In a preferred embodiment, the TWIK protein has an amino acid sequence shown in SEQ ID NO: 2, SEQ ID NO:5, SEQ ID NO:8, or SEQ ID NO:11. In other embodiments, the TWIK protein is substantially homologous to SEQ ID NO: 2, SEQ ID NO:5, SEQ ID NO:8, or SEQ ID NO:11, and retains the functional activity of the protein of SEQ ID NO: 2, SEQ ID NO:5, SEQ ID NO:8, or SEQ ID NO:11, yet differs in amino acid sequence due to natural allelic variation or mutagenesis, as described in detail in subsection I above. Accordingly, in another embodiment, the TWIK protein is a protein which comprises an amino acid sequence at least about 50%, 55%, 60%, 65%, 70%, 75%, 80%, 85%, 90%, 95% or more identical to SEQ ID NO: 2, SEQ ID NO:5, SEQ ID NO:8, or SEQ ID NO:11.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the TWIK amino acid sequence of SEQ ID NO:2, 5, or 8 having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to TWIK nucleic acid molecules of the invention. BLAST protein searches can be performed with the XBLAST program, score=50, wordlength=3 to obtain amino acid sequences homologous to TWIK protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The invention also provides TWIK chimeric or fusion proteins. As used herein, a TWIK "chimeric protein" or "fusion protein" comprises a TWIK polypeptide operatively linked to a non-TWIK polypeptide. An "TWIK polypeptide" refers to a polypeptide having an amino acid sequence corresponding to TWIK, whereas a "non-TWIK polypeptide" refers to a polypeptide having an amino acid sequence corresponding to a protein which is not substantially homologous to the TWIK protein, e.g., a protein which is different from the TWIK protein and which is derived from the same or a different organism. Within a TWIK fusion protein the TWIK polypeptide can correspond to all or a portion of a TWIK protein. In a preferred embodiment, a TWIK fusion protein comprises at least one biologically active portion of a TWIK protein. In another preferred embodiment, a TWIK fusion protein comprises at least two biologically active portions of a TWIK protein. Within the fusion protein, the term "operatively linked" is intended to indicate that the TWIK polypeptide and the non-TWIK polypeptide are fused in-frame to each other. The non-TWIK polypeptide can be fused to the N-terminus or C-terminus of the TWIK polypeptide.

For example, in one embodiment, the fusion protein is a GST-TWIK fusion protein in which the TWIK sequences are fused to the C-terminus of the GST sequences. Such fusion proteins can facilitate the purification of recombinant TWIK.

In another embodiment, the fusion protein is a TWIK protein containing a heterologous signal sequence at its N-terminus. In certain host cells (e.g., mammalian host cells), expression and/or secretion of TWIK can be increased through use of a heterologous signal sequence.

The TWIK fusion proteins of the invention can be incorporated into pharmaceutical compositions and administered to a subject in vivo. The TWIK fusion proteins can be used to affect the bioavailability of a TWIK substrate. Use of TWIK fusion proteins may be useful therapeutically for the treatment of CNS disorders, e.g., neurodegenerative disorders such as Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy and Jakob-Creutzfieldt disease; psychiatric disorders, e.g., depression, schizophrenic disorders, korsakoff's psychosis, mania, anxiety disorders, or phobic disorders; learning or memory disorders, e.g., amnesia or age-related memory loss; neurological disorders; e.g., migraine; and obesity.

Moreover, the TWIK-fusion proteins of the invention can be used as immunogens to produce anti-TWIK antibodies in a subject, to purify TWIK ligands and in screening assays to identify molecules which inhibit the interaction of TWIK with a TWIK substrate.

Preferably, a TWIK chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A TWIK-encoding nucleic acid can be cloned into such an expression vector such that the fusion moiety is linked in-frame to the TWIK protein.

The present invention also pertains to variants of the TWIK proteins which function as either TWIK agonists (mimetics) or as TWIK antagonists. Variants of the TWIK proteins can be generated by mutagenesis, e.g., discrete point mutation or truncation of a TWIK protein. An agonist of the TWIK proteins can retain substantially the same, or a subset, of the biological activities of the naturally occurring form of a TWIK protein. An antagonist of a TWIK protein can inhibit one or more of the activities of the naturally occurring form of the TWIK protein by, for example, competitively modulating a potassium channel mediated activity of a TWIK protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the TWIK protein.

In one embodiment, variants of a TWIK protein which function as either TWIK agonists (mimetics) or as TWIK antagonists can be identified by screening combinatorial libraries of mutants, e.g., truncation mutants, of a TWIK protein for TWIK protein agonist or antagonist activity. In one embodiment, a variegated library of TWIK variants is generated by combinatorial mutagenesis at the nucleic acid level and is encoded by a variegated gene library. A variegated library of TWIK variants can be produced by, for example, enzymatically ligating a mixture of synthetic oligonucleotides into gene sequences such that a degenerate set of potential TWIK sequences is expressible as individual polypeptides, or alternatively, as a set of larger fusion proteins (e.g., for phage display) containing the set of TWIK sequences therein. There are a variety of methods which can be used to produce libraries of potential TWIK variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential TWIK sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a TWIK protein coding sequence can be used to generate a variegated population of TWIK fragments for screening and subsequent selection of variants of a TWIK protein. In one embodiment, a library of coding sequence fragments can be generated by treating a double stranded PCR fragment of a TWIK coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the TWIK protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of TWIK proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify TWIK variants (Arkin and Youvan (1992) *Proc. Natl. Acad. Sci. USA* 89:7811-7815; Delgrave et al. (1993) *Protein Eng.* 6(3):327-331).

In one embodiment, cell based assays can be exploited to analyze a variegated TWIK library. For example, a library of expression vectors can be transfected into a cell line which ordinarily synthesizes TWIK. The transfected cells are then cultured such that TWIK and a particular mutant TWIK are expressed and the effect of expression of the mutant on TWIK activity in the cells can be detected, e.g., by any of a number of enzymatic assays or by detecting the release of a neurotransmitter. Plasmid DNA can then be recovered from the cells which score for inhibition, or alternatively, potentiation of TWIK activity, and the individual clones further characterized.

An isolated TWIK protein, or a portion or fragment thereof, can be used as an immunogen to generate antibodies that bind TWIK using standard techniques for polyclonal and monoclonal antibody preparation. A full-length TWIK protein can be used or, alternatively, the invention provides antigenic peptide fragments of TWIK for use as immunogens. The antigenic peptide of TWIK comprises at least 8 amino acid residues of the amino acid sequence shown in SEQ ID NO: 2, SEQ ID NO:5, SEQ ID NO:8, or SEQ ID NO:11 and encompasses an epitope of TWIK such that an antibody raised against the peptide forms a specific immune complex with TWIK. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of TWIK that are located on the surface of the protein, e.g., hydrophilic regions, as well as regions with high antigenicity (see, for example, FIGS. 2, 4, 6, and 18).

A TWIK immunogen typically is used to prepare antibodies by immunizing a suitable subject, (e.g., rabbit, goat, mouse or other mammal) with the immunogen. An appropriate immunogenic preparation can contain, for example, recombinantly expressed TWIK protein or a chemically synthesized TWIK polypeptide. The preparation can further include an adjuvant, such as Freund's complete or incomplete adjuvant, or similar immunostimulatory agent. Immunization of a suitable subject with an immunogenic TWIK preparation induces a polyclonal anti-TWIK antibody response.

Accordingly, another aspect of the invention pertains to anti-TWIK antibodies. The term "antibody" as used herein refers to immunoglobulin molecules and immunologically active portions of immunoglobulin molecules, i.e., molecules that contain an antigen binding site which specifically binds (immunoreacts with) an antigen, such as TWIK. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind TWIK. The term "monoclonal antibody" or "monoclonal antibody composition", as used herein, refers to a population of antibody molecules that contain only one species of an antigen binding site capable of immunoreacting with a particular epitope of TWIK. A monoclonal antibody composition thus typically displays a single binding affinity for a particular TWIK protein with which it immunoreacts.

Polyclonal anti-TWIK antibodies can be prepared as described above by immunizing a suitable subject with a TWIK immunogen. The anti-TWIK antibody titer in the immunized subject can be monitored over time by standard techniques, such as with an enzyme linked immunosorbent assay (ELISA) using immobilized TWIK. If desired, the antibody molecules directed against TWIK can be isolated from the mammal (e.g., from the blood) and further purified by well known techniques, such as protein A chromatography to obtain the IgG fraction. At an appropriate time after immunization, e.g., when the anti-TWIK antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem* 0.255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a TWIK immunogen as described above, and the culture supernatants of the resulting hybridoma cells are screened to identify a hybridoma producing a monoclonal antibody that binds TWIK.

Any of the many well known protocols used for fusing lymphocytes and immortalized cell lines can be applied for the purpose of generating an anti-TWIK monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind TWIK, e.g., using a standard ELISA assay.

Alternative to preparing monoclonal antibody-secreting hybridomas, a monoclonal anti-TWIK antibody can be identified and isolated by screening a recombinant combinatorial immunoglobulin library (e.g., an antibody phage display library) with TWIK to thereby isolate immunoglobulin library members that bind TWIK. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al. U.S. Pat. No. 5,223, 409; Kang et al. PCT International Publication No. WO 92/18619; Dower et al. PCT International Publication No. WO 91/17271; Winter et al. PCT International Publication No. WO 92/20791; Markland et al. PCT International Publication No. WO 92/15679; Breitling et al. PCT International Publication No. WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acid Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-TWIK antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et at. International Application No. PCT/US86/02269; Akira, et at. European Patent Application 184,187; Taniguchi, M., European Patent Application 171,496; Morrison et at. European Patent Application No. 173,494; Neuberger et at. PCT International Publication No. WO 86/01533; Cabilly et at. U.S. Pat. No. 4,816,567; Cabilly et at. European Patent Application No 125,023; Better et at. (1988) i Science 240:1041-1043; Liu et at. (1987) *Proc. Natl. Acad. Sci. USA* 84:3439-3443; Liu et al. (1987) *J. Immunol.* 139: 3521-3526; Sun et at. (1987) *Proc. Natl. Acad. Sci. USA* 84:214-218; Nishimura et at. (1987) *Cancer Res.* 47:999-1005; Wood et at. (1985) *Nature* 314:446-449; and Shaw et at. (1988) *J. Natl. Cancer Inst.* 80:1553-1559); Morrison, S. L. (1985) *Science* 229:1202-1207; Oi et at. (1986) *BioTechniques* 4:214; Winter U.S. Pat. No. 5,225,539; Jones et at. (1986) *Nature* 321:552-525; Verhoeyen et al. (1988) *Science* 239:1534; and Beidler et al. (1988) *J. Immunol.* 141:4053-4060.

An anti-TWIK antibody (e.g., monoclonal antibody) can be used to isolate TWIK by standard techniques, such as affinity chromatography or immunoprecipitation. An anti-TWIK antibody can facilitate the purification of natural TWIK from cells and of recombinantly produced TWIK expressed in host cells. Moreover, an anti-TWIK antibody can be used to detect TWIK protein (e.g., in a cellular lysate or cell supernatant) in order to evaluate the abundance and pattern of expression of the TWIK protein. Anti-TWIK antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a TWIK protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., TWIK proteins, mutant forms of TWIK proteins, fusion proteins, and the like).

The recombinant expression vectors of the invention can be designed for expression of TWIK proteins in prokaryotic or eukaryotic cells. For example, TWIK proteins can be expressed in bacterial cells such as E. coli, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in TWIK activity assays, (e.g., direct assays or competitive assays described in detail below), or to generate antibodies specific for TWIK proteins, for example. In a preferred embodiment, a TWIK fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion E. coli expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111-2118). Such alteration of nucleic acid sequences of the invention can be carried out by standard DNA synthesis techniques.

In another embodiment, the TWIK expression vector is a yeast expression vector. Examples of vectors for expression in yeast S. cerevisiae include pYepSec1 (Baldari, et al., (1987) *EMBO J.* 6:229-234), pMFa (Kurjan and Herskowitz, (1982) Cett 30:933-943), pJRY88 (Schultz et al, (1987) *Gene* 54:113-123), pYES2 (Invitrogen Corporation, San Diego, Calif.), and picZ (Invitrogen Corporation, San Diego, Calif.).

Alternatively, TWIK proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to TWIK mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a TWIK protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a TWIK protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a TWIK protein. Accordingly, the invention further provides methods for producing a TWIK protein using the host cells of the invention. In one embodiment, the method comprises culturing the host cell of invention (into which a recombinant expression vector encoding a TWIK protein has been introduced) in a suitable medium such that a TWIK protein is produced. In another embodiment, the method further comprises isolating a TWIK protein from the medium or the host cell.

The host cells of the invention can also be used to produce non-human transgenic animals. For example, in one embodiment, a host cell of the invention is a fertilized oocyte or an embryonic stem cell into which TWIK-coding sequences have been introduced. Such host cells can then be used to create non-human transgenic animals in which exogenous TWIK sequences have been introduced into their genome or homologous recombinant animals in which endogenous TWIK sequences have been altered. Such animals are useful for studying the function and/or activity of a TWIK and for identifying and/or evaluating modulators of TWIK activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous TWIK gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a TWIK-encoding nucleic acid into the male pronuclei of a fertilized oocyte, e.g., by microinjection, retroviral infection, and allowing the oocyte to develop in a pseudopregnant female foster animal. The TWIK cDNA sequence of SEQ ID NO:1 can be introduced as a transgene into the genome of a non-human animal. Alternatively, a nonhuman homologue of a human TWIK gene, such as a mouse or rat TWIK gene, can be used as a transgene. Alternatively, a TWIK gene homologue, such as another TWIK potassium channel family member, can be isolated based on hybridization to the TWIK cDNA sequences of SEQ ID NO:1, SEQ ID NO:3, SEQ ID NO:4, SEQ ID NO:6, SEQ ID NO:7, SEQ ID NO:9, SEQ ID NO:10, SEQ ID NO:12 or the DNA insert of the plasmid deposited with ATCC as Accession Number PTA-1640 (described further in subsection I above) and used as a transgene. Intronic sequences and polyadenylation signals can also be included in the transgene to increase the efficiency of expression of the transgene. A tissue-specific regulatory sequence(s) can be operably linked to a TWIK transgene to direct expression of a TWIK protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a TWIK transgene in its genome and/or expression of TWIK mRNA in tissues or cells of the animals. A transgenic founder animal can then be used to breed additional animals carrying the transgene.

Moreover, transgenic animals carrying a transgene encoding a TWIK protein can further be bred to other transgenic animals carrying other transgenes.

To create a homologous recombinant animal, a vector is prepared which contains at least a portion of a TWIK gene into which a deletion, addition or substitution has been introduced to thereby alter, e.g., functionally disrupt, the TWIK gene. The TWIK gene can be a human gene (e.g., the cDNA of SEQ ID NO:3, 6, 9, or 12), but more preferably, is a non-human homologue of a human TWIK gene (e.g., a cDNA isolated by stringent hybridization with the nucleotide sequence of SEQ ID NO:1, 4, 7, or 10). For example, a mouse TWIK gene can be used to construct a homologous recombination vector suitable for altering an endogenous TWIK gene in the mouse genome. In a preferred embodiment, the vector is designed such that, upon homologous recombination, the endogenous TWIK gene is functionally disrupted (i.e., no longer encodes a functional protein; also referred to as a "knock out" vector). Alternatively, the vector can be designed such that, upon homologous recombination, the endogenous TWIK gene is mutated or otherwise altered but still encodes functional protein (e.g., the upstream regulatory region can be altered to thereby alter the expression of the endogenous TWIK protein). In the homologous recombination vector, the altered portion of the TWIK gene is flanked at its 5' and 3' ends by additional nucleic acid sequence of the TWIK gene to allow for homologous recombination to occur between the exogenous TWIK gene carried by the vector and an endogenous TWIK gene in an embryonic stem cell. The additional flanking TWIK nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced TWIK gene has homologously recombined with the endogenous TWIK gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The TWIK nucleic acid molecules, fragments of TWIK proteins, and anti-TWIK antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a TWIK protein or an anti-TWIK antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein.

When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a TWIK protein of the invention has one or more of the following activities: (1) it can modulate the release of neurotransmitters, (2) it can modulate membrane excitability, (3) it can influence the resting potential of membranes, (4) it can modulate wave forms and frequencies of action potentials, (5) it can modulate thresholds of excitation, and (6) it can modulate processes which underlie learning and memory, such as integration of sub-threshold synaptic responses and the conductance of back-propagating action potentials, and, thus, can be used to, for example, (1) modulate the release of neurotransmitters, (2) modulate membrane excitability, (3) influence the resting potential of membranes, (4) modulate wave forms and frequencies of action potentials, (5) modulate thresholds of excitation, and (6) modulate processes which underlie learning and memory, such as integration of sub-threshold synaptic responses and the conductance of back-propagating action potentials.

The isolated nucleic acid molecules of the invention can be used, for example, to express TWIK protein (e.g., via a recombinant expression vector in a host cell in gene therapy applications), to detect TWIK mRNA (e.g., in a biological sample) or a genetic alteration in a TWIK gene, and to modulate TWIK activity, as described further below. The TWIK proteins can be used to treat disorders characterized by insufficient or excessive production of a TWIK substrate or production of TWIK inhibitors. In addition, the TWIK proteins can be used to screen for naturally occurring TWIK substrates, to screen for drugs or compounds which modulate TWIK activity, as well as to treat disorders characterized by insufficient or excessive production of TWIK protein or production of TWIK protein forms which have decreased or aberrant activity compared to TWIK wild type protein (e.g., CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy and Jakob-Creutzfieldt disease; psychiatric disorders, e.g., depression, schizophrenic disorders, korsakoff's psychosis, mania, anxiety disorders, or phobic disorders; learning or memory disorders, e.g., amnesia or age-related memory loss; neurological disorders, e.g., migraine; obesity; and cardiac disorders, e.g., cardiac arrhythmia). Moreover, the anti-TWIK antibodies of the invention can be used to detect and isolate TWIK proteins, regulate the bioavailability of TWIK proteins, and modulate TWIK activity.

A. Screening Assays

The invention provides a method (also referred to herein as a "screening assay") for identifying modulators, i.e., candidate or test compounds or agents (e.g., peptides, peptidomimetics, small molecules or other drugs) which bind to TWIK proteins, have a stimulatory or inhibitory effect on, for example, TWIK expression or TWIK activity, or have a stimulatory or inhibitory effect on, for example, the expression or activity of TWIK substrate.

In one embodiment, the invention provides assays for screening candidate or test compounds which are substrates of a TWIK protein or polypeptide or biologically active portion thereof. In another embodiment, the invention provides assays for screening candidate or test compounds which bind to or modulate the activity of a TWIK protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a TWIK protein or biologically active portion thereof is contacted with a test compound and the ability of the test compound to modulate TWIK activity is determined. Determining the ability of the test compound to modulate TWIK activity can be accomplished by monitoring, for example, the release of a neurotransmitter form a cell which expresses TWIK. The cell, for example, can be of mammalian origin. Determining the ability of the test compound to modulate the ability of TWIK to bind to a substrate can be accomplished, for example, by coupling the TWIK substrate with a radioisotope or enzymatic label such that binding of the TWIK substrate to TWIK can be determined by detecting the labeled TWIK substrate in a complex. For example, compounds (e.g., TWIK substrates) can be labeled with $^{125}I$, $^{35}S$, $^{14}C$, or $^{3}H$, either directly or indirectly, and the radioisotope detected by direct counting of radio emission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., TWIK substrate) to interact with TWIK without the labeling of any of the interactants. For example, a microphysiometer can be used to detect the interaction of a compound with TWIK without the labeling of either the compound or the TWIK. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and TWIK.

In another embodiment, an assay is a cell-based assay comprising contacting a cell expressing a TWIK target molecule (e.g., a TWIK substrate) with a test compound and determining the ability of the test compound to modulate (e.g. stimulate or inhibit) the activity of the TWIK target molecule. Determining the ability of the test compound to modulate the activity of a TWIK target molecule can be accomplished, for example, by determining the ability of the TWIK protein to bind to or interact with the TWIK target molecule.

Determining the ability of the TWIK protein or a biologically active fragment thereof, to bind to or interact with a TWIK target molecule can be accomplished by one of the methods described above for determining direct binding. In a preferred embodiment, determining the ability of the TWIK protein to bind to or interact with a TWIK target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a TWIK protein or biologically active portion thereof is contacted with a test compound and the ability of the test compound to bind to the TWIK protein or biologically active portion thereof is determined. Preferred biologically active portions of the TWIK proteins to be used in assays of the present invention include fragments which participate in interactions with non-TWIK molecules, e.g., cyclic nucleotides, or fragments with high surface probability scores (see, for example, FIGS. 2, 4, 6, and 18). Binding of the test compound to the TWIK protein can be determined either directly or indirectly as described above. In a preferred embodiment, the assay includes contacting the TWIK protein or biologically active portion thereof with a known compound which binds TWIK to form an assay mixture, contacting the assay mixture with a test compound, and determining the ability of the test compound to interact with a TWIK protein, wherein determining the ability of the test compound to interact with a TWIK protein comprises determining the ability of the test compound to preferentially bind to TWIK or biologically active portion thereof as compared to the known compound.

In another embodiment, the assay is a cell-free assay in which a TWIK protein or biologically active portion thereof is contacted with a test compound and the ability of the test compound to modulate (e.g., stimulate or inhibit) the activity of the TWIK protein or biologically active portion thereof is determined. Determining the ability of the test compound to modulate the activity of a TWIK protein can be accomplished, for example, by determining the ability of the TWIK protein to bind to a TWIK target molecule by one of the methods described above for determining direct binding. Determining the ability of the TWIK protein to bind to a TWIK target molecule can also be accomplished using a matrix technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a TWIK protein can be accomplished by determining the ability of the TWIK protein to further modulate the activity of a downstream effector of a TWIK target molecule. For example, the activity of the effector molecule on an appropriate target can be determined or the binding of the effector to an appropriate target can be determined as previously described.

In yet another embodiment, the cell-free assay involves contacting a TWIK protein or biologically active portion thereof with a known compound which binds the TWIK protein to form an assay mixture, contacting the assay mixture with a test compound, and determining the ability of the test compound to interact with the TWIK protein, wherein determining the ability of the test compound to interact with the TWIK protein comprises determining the ability of the TWIK protein to preferentially bind to or modulate the activity of a TWIK target molecule.

The cell-free assays of the present invention are amenable to use of both soluble and/or membrane-bound forms of isolated proteins (e.g., TWIK proteins or biologically active portions thereof). In the case of cell-free assays in which a membrane-bound form an isolated protein is used (e.g., a potassium channel) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either TWIK or its target molecule to facilitate separation of complexed from uncomplexed forms of one or both of the proteins, as well as to accommodate automation of the assay. Binding of a test compound to a TWIK protein, or interaction of a TWIK protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-Stransferase/TWIK fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or TWIK protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of TWIK binding or activity determined using standard techniques.

Other techniques for immobilizing proteins on matrices can also be used in the screening assays of the invention. For example, either a TWIK protein or a TWIK target molecule can be immobilized utilizing conjugation of biotin and streptavidin. Biotinylated TWIK protein or target molecules can be prepared from biotin-NHS(N-hydroxysuccinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with TWIK protein or target molecules but which do not interfere with binding of the TWIK protein to its target molecule can be derivatized to the wells of the plate, and unbound target or TWIK protein trapped in the wells by antibody conjugation. Methods for detecting such complexes, in addition to those described above for the GST-immobilized complexes, include immunodetection of complexes using antibodies reactive with the TWIK protein or target molecule, as well as enzyme-linked assays which rely on detecting an enzymatic activity associated with the TWIK protein or target molecule.

In another embodiment, modulators of TWIK expression are identified in a method wherein a cell is contacted with a candidate compound and the expression of TWIK mRNA or protein in the cell is determined. The level of expression of TWIK mRNA or protein in the presence of the candidate compound is compared to the level of expression of TWIK mRNA or protein in the absence of the candidate compound. The candidate compound can then be identified as a modulator of TWIK expression based on this comparison. For example, when expression of TWIK mRNA or protein is greater (statistically significantly greater) in the presence of the candidate compound than in its absence, the candidate compound is identified as a stimulator of TWIK mRNA or protein expression. Alternatively, when expression of TWIK mRNA or protein is less (statistically significantly less) in the presence of the candidate compound than in its absence, the candidate compound is identified as an inhibitor of TWIK mRNA or protein expression. The level of TWIK mRNA or protein expression in the cells can be determined by methods described herein for detecting TWIK mRNA or protein.

In yet another aspect of the invention, the TWIK proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with TWIK ("TWIK-binding proteins" or "TWIK-bp") and are involved in TWIK activity. Such TWIK-binding proteins are also likely to be involved in the propagation of signals by the TWIK proteins or TWIK targets as, for example, downstream elements of a TWIK-mediated signaling pathway. Alternatively, such TWIK-binding proteins are likely to be TWIK inhibitors.

The two-hybrid system is based on the modular nature of most transcription factors, which consist of separable DNA-binding and activation domains. Briefly, the assay utilizes two different DNA constructs. In one construct, the gene that codes for a TWIK protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a TWIK-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the TWIK protein.

This invention further pertains to novel agents identified by the above-described screening assays. Accordingly, it is within the scope of this invention to further use an agent identified as described herein in an appropriate animal model. For example, an agent identified as described herein (e.g., a TWIK modulating agent, an antisense TWIK nucleic acid molecule, a TWIK-specific antibody, or a TWIK-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the TWIK nucleotide sequences, described herein, can be used to map the location of the TWIK genes on a chromosome. The mapping of the TWIK sequences to chromosomes is an important first step in correlating these sequences with genes associated with disease.

Briefly, TWIK genes can be mapped to chromosomes by preparing PCR primers (preferably 15-25 bp in length) from the TWIK nucleotide sequences. Computer analysis of the TWIK sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the TWIK sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the TWIK nucleotide sequences to design oligonucleotide primers, sublocalization can be achieved with panels of fragments from specific chromosomes. Other mapping strategies which can similarly be used to map a TWIK sequence to its chromosome include in situ hybridization (described in Fan, Y. et al. (1990) *Proc. Natl. Acad. Sci. USA,* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available online through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783-787.

Moreover, differences in the DNA sequences between individuals affected and unaffected with a disease associated with the TWIK gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The TWIK sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the TWIK nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The TWIK nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:4, SEQ ID NO:7, or SEQ ID NO:10 can comfortably provide positive individual identification with a panel of perhaps 10 to 1,000 primers which each yield a noncoding amplified sequence of 100 bases. If predicted coding sequences, such as those in SEQ ID NO:3, SEQ ID NO:6, SEQ ID NO:9, or SEQ ID NO:12 are used, a more appropriate number of primers for positive individual identification would be 500-2,000.

If a panel of reagents from TWIK nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial TWIK Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to non-coding regions of SEQ ID NO:1, SEQ ID NO:4, SEQ ID NO:7, or SEQ ID NO:10 are particularly appropriate for this use as greater numbers of polymorphisms occur in the noncoding regions, making it easier to differentiate individuals using this technique. Examples of polynucleotide reagents include the TWIK nucleotide sequences or portions thereof, e.g., fragments derived from the non-coding regions of SEQ ID NO:1, SEQ ID NO:4, SEQ ID NO:7, or SEQ ID NO:10, having a length of at least 20 bases, preferably at least 30 bases.

The TWIK nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such TWIK probes can be used to identify tissue by species and/or by organ type.

In a similar fashion, these reagents, e.g., TWIK primers or probes can be used to screen tissue culture for contamination (i.e. screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining TWIK protein and/or nucleic acid expression as well as TWIK activity, in the context of a biological sample (e.g., blood, serum, cells, tissue) to thereby determine whether an individual is afflicted with a disease or disorder, or is at risk of developing a disorder, associated with aberrant TWIK expression or activity. The invention also provides for prognostic (or predictive) assays for determining whether an individual is at risk of developing a disorder associated with TWIK protein, nucleic acid expression or activity. For example, mutations in a TWIK gene can be assayed in a biological sample. Such assays can be used for prognostic or predictive purpose to thereby prophylactically treat an individual prior to the onset of a disorder characterized by or associated with TWIK protein, nucleic acid expression or activity.

Another aspect of the invention pertains to monitoring the influence of agents (e.g., drugs, compounds) on the expression or activity of TWIK in clinical trials.

These and other agents are described in further detail in the following sections.

1. Diagnostic Assays

An exemplary method for detecting the presence or absence of TWIK protein or nucleic acid in a biological sample involves obtaining a biological sample from a test subject and contacting the biological sample with a compound or an agent capable of detecting TWIK protein or nucleic acid (e.g., mRNA, genomic DNA) that encodes TWIK protein such that the presence of TWIK protein or nucleic acid is detected in the biological sample. A preferred agent for detecting TWIK mRNA or genomic DNA is a labeled nucleic acid probe capable of hybridizing to TWIK mRNA or genomic DNA. The nucleic acid probe can be, for example, a full-length TWIK nucleic acid, such as the nucleic acid of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or the DNA insert of the plasmid deposited with ATCC as Accession Number PTA-1640, or a portion thereof, such as an oligonucleotide of at least 15, 30, 50, 100, 250 or 500 nucleotides in length and sufficient to specifically hybridize under stringent conditions to TWIK mRNA or genomic DNA. Other suitable probes for use in the diagnostic assays of the invention are described herein.

A preferred agent for detecting TWIK protein is an antibody capable of binding to TWIK protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect TWIK mRNA, protein, or genomic DNA in a biological sample in vitro as well as in vivo. For example, in vitro techniques for detection of TWIK mRNA include Northern hybridizations and in situ hybridizations. In vitro techniques for detection of TWIK protein include enzyme linked immunosorbent assays (ELISAs), Western blots, immunoprecipitations and immunofluorescence. In vitro techniques for detection of TWIK genomic DNA include Southern hybridizations. Furthermore, in vivo techniques for detection of TWIK protein include introducing into a subject a labeled anti-TWIK antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting TWIK protein, mRNA, or genomic DNA, such that the presence of TWIK protein, mRNA or genomic DNA is detected in the biological sample, and comparing the presence of TWIK protein, mRNA or genomic DNA in the control sample with the presence of TWIK protein, mRNA or genomic DNA in the test sample.

The invention also encompasses kits for detecting the presence of TWIK in a biological sample. For example, the kit can comprise a labeled compound or agent capable of detecting TWIK protein or mRNA in a biological sample; means for determining the amount of TWIK in the sample; and means for comparing the amount of TWIK in the sample with a standard. The compound or agent can be packaged in a suitable container. The kit can further comprise instructions for using the kit to detect TWIK protein or nucleic acid.

2. Prognostic Assays

The diagnostic methods described herein can furthermore be utilized to identify subjects having or at risk of developing a disease or disorder associated with aberrant TWIK expression or activity. For example, the assays described herein, such as the preceding diagnostic assays or the following assays, can be utilized to identify a subject having or at risk of developing a disorder associated with a misregulation in TWIK protein activity or nucleic acid expression, such as a CNS disorder. Alternatively, the prognostic assays can be utilized to identify a subject having or at risk for developing a disorder associated with a misregulation in TWIK protein activity or nucleic acid expression, such as a CNS disorder. Thus, the present invention provides a method for identifying a disease or disorder associated with aberrant TWIK expression or activity in which a test sample is obtained from a subject and TWIK protein or nucleic acid (e.g., mRNA or genomic DNA) is detected, wherein the presence of TWIK protein or nucleic acid is diagnostic for a subject having or at risk of developing a disease or disorder associated with aberrant TWIK expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant TWIK expression or activity. For example, such methods can be used to determine whether a subject can be effectively treated with an agent for a CNS disorder. Thus, the present invention provides methods for determining whether a subject can be effectively treated with an agent for a disorder associated with aberrant TWIK expression or activity in which a test sample is obtained and TWIK protein or nucleic acid expression or activity is detected (e.g., wherein the abundance of TWIK protein or nucleic acid expression or activity is diagnostic for a subject that can be administered the agent to treat a disorder associated with aberrant TWIK expression or activity).

The methods of the invention can also be used to detect genetic alterations in a TWIK gene, thereby determining if a subject with the altered gene is at risk for a disorder characterized by misregulation in TWIK protein activity or nucleic acid expression, such as a CNS disorder. In preferred embodiments, the methods include detecting, in a sample of cells from the subject, the presence or absence of a genetic alteration characterized by at least one of an alteration affecting the integrity of a gene encoding a TWIK-protein, or the misexpression of the TWIK gene. For example, such genetic alterations can be detected by ascertaining the existence of at least one of 1) a deletion of one or more nucleotides from a TWIK gene; 2) an addition of one or more nucleotides to a TWIK gene; 3) a substitution of one or more nucleotides of a TWIK gene, 4) a chromosomal rearrangement of a TWIK gene; 5) an alteration in the level of a messenger RNA transcript of a TWIK gene, 6) aberrant modification of a TWIK gene, such as of the methylation pattern of the genomic DNA, 7) the presence of a non-wild type splicing pattern of a messenger RNA transcript of a TWIK gene, 8) a non-wild type level of a TWIK-protein, 9) allelic loss of a TWIK gene, and 10) inappropriate post-translational modification of a TWIK-protein. As described herein, there are a large number of assays known in the art which can be used for detecting alterations in a TWIK gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the TWIK-gene (see Abravaya et al. (1995) Nucleic Acids Res 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a TWIK gene under conditions such that hybridization and amplification of the TWIK-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874-1878), transcriptional amplification system (Kwoh, D. Y. et al., (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a TWIK gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in TWIK can be identified by hybridizing a sample and control nucleic acids, e.g., DNA or RNA, to high density arrays containing hundreds or thousands of oligonucleotides probes (Cronin, M. T. et al. (1996) Human Mutation 7: 244-255; Kozal, M. J. et al. (1996) Nature Medicine 2: 753-759). For example, genetic mutations in TWIK can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the TWIK gene and detect mutations by comparing the sequence of the sample TWIK with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the TWIK gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type TWIK sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl Acad Sci USA 85:4397; Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in TWIK cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a TWIK sequence, e.g., a wild-type TWIK sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in TWIK genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control TWIK nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) Proc. Natl Acad Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving a TWIK gene.

Furthermore, any cell type or tissue in which TWIK is expressed may be utilized in the prognostic assays described herein.

3. Monitoring of Effects During Clinical Trials

Monitoring the influence of agents (e.g., drugs) on the expression or activity of a TWIK protein (e.g., the modulation of membrane excitability or resting potential) can be applied not only in basic drug screening, but also in clinical trials. For example, the effectiveness of an agent determined by a screening assay as described herein to increase TWIK gene expression, protein levels, or upregulate TWIK activity, can be monitored in clinical trials of subjects exhibiting decreased TWIK gene expression, protein levels, or down-regulated TWIK activity. Alternatively, the effectiveness of an agent determined by a screening assay to decrease TWIK gene expression, protein levels, or downregulate TWIK activity, can be monitored in clinical trials of subjects exhibiting increased TWIK gene expression, protein levels, or upregulated TWIK activity. In such clinical trials, the expression or activity of a TWIK gene, and preferably, other genes that have been implicated in, for example, a potassium channel associated disorder can be used as a "read out" or markers of the phenotype of a particular cell.

For example, and not by way of limitation, genes, including TWIK, that are modulated in cells by treatment with an agent (e.g., compound, drug or small molecule) which modulates TWIK activity (e.g., identified in a screening assay as described herein) can be identified. Thus, to study the effect of agents on potassium channel associated disorders, for example, in a clinical trial, cells can be isolated and RNA prepared and analyzed for the levels of expression of TWIK and other genes implicated in the potassium channel associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of TWIK or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a TWIK protein, mRNA, or genomic DNA in the preadministration sample; (iii) obtaining one or more post-administration samples from the subject; (iv) detecting the level of expression or activity of the TWIK protein, mRNA, or genomic DNA in the post-administration samples; (v) comparing the level of expression or activity of the TWIK protein, mRNA, or genomic DNA in the pre-administration sample with the TWIK protein, mRNA, or genomic DNA in the post administration sample or samples; and (vi) altering the administration of the agent to the subject accordingly. For example, increased administration of the agent may be desirable to increase the expression or activity of TWIK to higher levels than detected, i.e., to increase the effectiveness of the agent. Alternatively, decreased administration of the agent may be desirable to decrease expression or activity of TWIK to lower levels than detected, i.e. to decrease the effectiveness of the agent. According to such an embodiment, TWIK expression or activity may be used as an indicator of the effectiveness of an agent, even in the absence of an observable phenotypic response.

C. Methods of Treatment

The present invention provides for both prophylactic and therapeutic methods of treating a subject at risk of (or susceptible to) a disorder or having a disorder associated with aberrant TWIK expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the TWIK molecules of the present invention or TWIK modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant TWIK expression or activity, by administering to the subject a TWIK or an agent which modulates TWIK expression or at least one TWIK activity. Subjects at risk for a disease which is caused or contributed to by aberrant TWIK expression or activity can be identified by, for example, any or a combination of diagnostic or prognostic assays as described herein. Administration of a prophylactic agent can occur prior to the manifestation of symptoms characteristic of the TWIK aberrancy, such that a disease or disorder is prevented or, alternatively, delayed in its progression. Depending on the type of TWIK aberrancy, for example, a TWIK, TWIK agonist or TWIK antagonist agent can be used for treating the subject. The appropriate agent can be determined based on screening assays described herein.

2. Therapeutic Methods

Another aspect of the invention pertains to methods of modulating TWIK expression or activity for therapeutic purposes. Accordingly, in an exemplary embodiment, the modulatory method of the invention involves contacting a cell with a TWIK or agent that modulates one or more of the activities of TWIK protein activity associated with the cell. An agent that modulates TWIK protein activity can be an agent as described herein, such as a nucleic acid or a protein, a naturally-occurring target molecule of a TWIK protein (e.g., a TWIK substrate), a TWIK antibody, a TWIK agonist or antagonist, a peptidomimetic of a TWIK agonist or antagonist, or other small molecule. In one embodiment, the agent stimulates one or more TWIK activities. Examples of such stimulatory agents include active TWIK protein and a nucleic acid molecule encoding TWIK that has been introduced into the cell. In another embodiment, the agent inhibits one or more TWIK activities. Examples of such inhibitory agents include antisense TWIK nucleic acid molecules, anti-TWIK antibodies, and TWIK inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a TWIK protein or nucleic acid molecule. In one embodiment, the method involves administering an agent (e.g., an agent identified by a screening assay described herein), or combination of agents that modulates (e.g., upregulates or downregulates) TWIK expression or activity. In another embodiment, the method involves administering a TWIK protein or nucleic acid molecule as therapy to compensate for reduced or aberrant TWIK expression or activity.

A preferred embodiment of the present invention involves a method for treatment of a TWIK associated disease or disorder which includes the step of administering a therapeutically effective amount of a TWIK antibody to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Stimulation of TWIK activity is desirable in situations in which TWIK is abnormally downregulated and/or in which increased TWIK activity is likely to have a beneficial effect. For example, stimulation of TWIK activity is desirable in situations in which a TWIK is downregulated and/or in which increased TWIK activity is likely to have a beneficial effect. Likewise, inhibition of TWIK activity is desirable in situations in which TWIK is abnormally upregulated and/or in which decreased TWIK activity is likely to have a beneficial effect.

3. Pharmacogenomics

The TWIK molecules of the present invention, as well as agents, or modulators which have a stimulatory or inhibitory effect on TWIK activity (e.g., TWIK gene expression) as identified by a screening assay described herein can be administered to individuals to treat (prophylactically or therapeutically) potassium channel associated disorders (e.g., CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, korsakoffs psychosis, mania, anxiety disorders, or phobic disorders; learning or memory disorders, e.g., amnesia or age-related memory loss; neurological disorders; e.g., migraine; and obesity) associated with aberrant TWIK activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a TWIK molecule or TWIK modulator as well as tailoring the dosage and/or therapeutic regimen of treatment with a TWIK molecule or TWIK modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol Physiol. 23(10-11): 983-985 and Linder, M. W. et al. (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a TWIK protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a TWIK molecule or TWIK modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a TWIK molecule or TWIK modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing are incorporated herein by reference.

EXAMPLES

Example 1

Identification and Characterization of TWIK-2, TWIK-3, TWIK-4, AND TWIK-5 cDNA

In this example, the identification and characterization of the genes encoding human TWIK-2 (clone Fthka20g4), human TWIK-3 (clone Athual33f10), human TWIK-4 (clone AthTb005e07), and human TWIK-5 are described.

Isolation of the Human TWIK2, TWIK-3, TWIK-4 and TWIK-5 cDNA

The invention is based, at least in part, on the discovery of four human genes encoding four novel proteins, referred to herein as TWIK-2, TWIK-3, TWIK-4, and TWIK5. TWIK-2, TWIK-3, and TWIK-4 were identified as ESTs in a proprietary database based on their homology to the N-terminal domain of TWIK family members. TWIK-5 was initially identified as an EST in a monkey dorsal root ganglion library. This EST was subsequently used to perform a BLAST search in a proprietary database, thereby identifying *Homo sapiens* chromosome 10 clone CIT987SK-1143A11 (Accession No. AC005880) and *Homo sapiens* chromosome 10 clone CIT987SK-105402 (Accession No. AC005661). A contig of these clones was formed, the exons were identified (based on their homology to the monkey cDNA) and the human TWIK-5 cDNA was constructed.

To clone the TWIK-5 cDNA, PCR primers are designed based on the constructed TWIK-5 cDNA sequence and used to screen a dorsal root ganglion library. The positive clones identified are sequenced, and the sequences are assembled. The TWIK-5 cDNA can then be cloned into a vector and expressed in a cell, and the activity of the TWIK-5 protein can then be determined using any of the assays described herein.

The nucleotide sequence encoding the human TWIK-2 protein is shown in FIG. 1 and is set forth as SEQ ID NO:1. The full length protein encoded by this nucleic acid comprises about 499 amino acids and has the amino acid sequence shown in FIG. 1 and set forth as SEQ ID NO:2. The coding region (open reading frame) of SEQ ID NO:1 is set forth as SEQ ID NO:3.

The nucleotide sequence encoding the human TWIK-3 protein is shown in FIG. 3 and is set forth as SEQ ID NO:4. The full length protein encoded by this nucleic acid comprises about 332 amino acids and has the amino acid sequence shown in FIG. 3 and set forth as SEQ ID NO:5. The coding region (open reading frame) of SEQ ID NO:4 is set forth as SEQ ID NO:6.

The nucleotide sequence encoding the human TWIK-4 protein is shown in FIG. 5 and is set forth as SEQ ID NO:7. The full length protein encoded by this nucleic acid comprises about 313 amino acids and has the amino acid sequence shown in FIG. 5 and set forth as SEQ ID NO:8. The coding region (open reading frame) of SEQ ID NO:7 is set forth as SEQ ID NO:9.

The nucleotide sequence encoding the human TWIK-5 protein is shown in FIG. 17 and is set forth as SEQ ID NO:10. The full length protein encoded by this nucleic acid comprises about 401 amino acids and has the amino acid sequence shown in FIG. 17 and set forth as SEQ ID NO:11. The coding region (open reading frame) of SEQ ID NO:10 is set forth as SEQ ID NO:12. Clone Fbh51164a, comprising the entire coding region of human TWIK-5 was deposited with the American Type Culture Collection (ATCC®), 10801 University Boulevard, Manassas. Va. 20110-2209. on Apr. 5, 2000, and assigned Accession No. PTA-1640.

Analysis of Human TWIK2, TWIK-3, TWIK-4, and TWIK-5

A BLASTX 1.4 search, using a score of 100 and a word length of 3 (Altschul et al. (1990) *J. Mol. Biol.* 215:403) of the translated nucleotide sequence of human TWIK-2 revealed that human TWIK-2 is similar to the human TASK-2 protein (Accession Number AF084830). The human TWIK-2 protein is 97% identical to the human TASK-2 protein (Accession Number AF084830) over translated nucleotides 10 to 957 and 90% identical to the human TASK-2 protein (Accession Number AF084830) over translated nucleotides 1042 to 1506.

A BLASTN 1.4.9 search, using a score of 100 and a word length of 12 (Altschul et al. (1990) *J. Mol. Biol.* 215:403) of the nucleotide sequence of human TWIK-2 revealed that TWIK-2 is similar to the nucleic acid encoding the human TASK-2 protein (Accession Number AF084830). The TWIK-2 nucleic acid molecule is 98% identical to the nucleic acid encoding the human TASK-2 protein (Accession Number AF084830) over nucleotides 1 to 1644, 99% identical over nucleotides 1590 to 2518, and 99% identical over nucleotides 2788 to 3426.

A BLASTX 1.4 search, using a score of 100 and a word length of 3 (Altschul et al. (1990) *J. Mol. Biol.* 215:403) of the translated nucleotide sequence of human TWIK-3 revealed that human TWIK-3 is similar to the human TASK-2 protein (Accession Number AF084830). The human TWIK-3 protein is 42% identical to the human TASK-2 protein (Accession Number AF084830) over translated nucleotides 719 to 982 and 37% identical to the human TASK-2 protein (Accession Number AF084830) over translated nucleotides 353 to 577.

A BLASTN 1.4.9 search, using a score of 100 and a word length of 12 (Altschul et al. (1990) *J. Mol. Biol.* 215:403) of the nucleotide sequence of human TWIK-3 revealed that TWIK-3 is similar to the human genomic clone 2385B13 (Accession Number AQ240175). The TWIK-3 nucleic acid molecule is 98% identical to the human genomic clone 2385B13 (Accession Number AQ240175) over nucleotides 1176 to 1544.

A BLASTX 1.4 search, using a score of 100 and a word length of 3 (Altschul et al. (1990) *J. Mol. Biol.* 215:403) of the translated nucleotide sequence of human TWIK-4 revealed that human TWIK-4 is similar to the human TWIK-1 protein (Accession Number U33632). The human TWIK-4 protein is 53% identical to the human TWIK-1 protein (Accession Number U33632) over translated nucleotides 406 to 837, and 42% identical to over translated nucleotides 220 to 390.

A BLASTN 1.4.9 search, using a score of 100 and a word length of 12 (Altschul et al. (1990) *J. Mol. Biol.* 215:403) of the nucleotide sequence of human TWIK-4 revealed that TWIK-4 is similar to the human potassium channel KCNO1 mRNA (Accession Number U90065). The TWIK-4 nucleic acid molecule is 63% identical to the human potassium channel KCNO1 mRNA (Accession Number U90065) over nucleotides 405 to 905.

The TWIK-2 protein was aligned with the TWIK-3 protein using the GAP program in the GCG software package (Blosum 62 matrix) and a gap weight of 12 and a length weight of 4. The results showed a 32.166% identity and 40.764% similarity between the two protein sequences (see FIG. 10).

The TWIK-2 protein was also aligned with the TWIK-4 protein using the GAP program in the GCG software package (Blosum 62 matrix) and a gap weight of 12 and a length weight of 4. The results showed a 27.333% identity and 37.667% similarity between the two protein sequences (see FIG. 11).

The TWIK-3 protein was further aligned with the TWIK-4 protein using the GAP program in the GCG software package (Blosum 62 matrix) and a gap weight of 12 and a length weight of 4. The results showed a 31.667% identity and 40.333% similarity between the two protein sequences (see FIG. 12).

The TWIK-1 protein was aligned with the TWIK-2 protein using the GAP program in the GCG software package (Blosum 62 matrix) and a gap weight of 12 and a length weight of 4. The results showed a 26.433% identity and 36.943% similarity between the two protein sequences (see FIG. 13).

The TWIK-1 protein was also aligned with the TWIK-3 protein using the GAP program in the GCG software package (Blosum 62 matrix) and a gap weight of 12 and a length weight of 4. The results showed a 22.961% identity and 31.420% similarity between the two protein sequences (see FIG. 14).

The TWIK-1 protein was further aligned with the TWIK-4 protein using the GAP program in the GCG software package (Blosum 62 matrix) and a gap weight of 12 and a length weight of 4. The results showed a 46.284% identity and 55.405% similarity between the two protein sequences (see FIG. 15).

The TWIK-2 protein was aligned with the hTASK-2 protein (described in Reyes R. et al. (1998) *J. Biol. Chem.* 273

(47):30863-30869) using the GAP program in the GCG software package (Blosum 62 matrix) and a gap weight of 12 and a length weight of 4. The results showed a 100% identity and 100% similarity between the two protein sequences (see FIG. 16).

The TWIK-5 protein was aligned with the hTASK-2 protein (described in Reyes R. et al. (1998) *J. Biol. Chem.* 273 (47):30863-30869) using the GAP program in the GCG software package (PAM250 matrix) and a gap weight of 25 and a length weight of 1. The results showed a 29.183% identity and 49.805% similarity between the two protein sequences (see FIG. 19).

The TWIK-5 protein was also aligned with the mouse TREK protein using the GAP program in the GCG software package (PAM250 matrix) and a gap weight of 25 and a length weight of 1. The results showed a 27.273% identity and 44.697% similarity between the two protein sequences (see FIG. 20).

A multiple sequence alignment of the amino acid sequence of human TWIK-4, human TWIK-1, murine TRAAK, murine TREK-1, human TWIK-3, human TWIK-2, and human TASK is presented in FIG. 7; a multiple sequence alignment of the amino acid sequence of human TWIK-1, human TWIK-4, murine TRAAK, murine TREK-1, and human TASK is presented in FIG. 8; and a multiple sequence alignment of the amino acid sequence of human TWIK-3, human TASK2, human TWIK-1, and human TASK is presented in FIG. 9.

Hydropathy plots have identified 4 transmembrane domains and two P-loops in each of TWIK-2, TWIK-3, TWIK-4, and TWIK-5 (see FIGS. 2, 4, 6, and 18).

Tissue Distribution of Human TWIK2, TWIK-3, TWIK-4, and TWIK-5 mRNA

This Example describes the tissue distribution of human TWIK2, TWIK-3, TWIK-4, and TWIK-5 mRNA, as may be determined by Northern blot hybridization, in situ hybridization, and PCR.

Northern blot hybridizations with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) were probed in ExpressHyb hybridization solution (Clontech) and washed at high stringency according to manufacturer's recommendations. Using the above-described methods, it was determined that TWIK-5 is expressed in dorsal root ganglion (DRG) neurons.

TWIK-5 expression in normal human and monkey tissues was assessed by PCR using the Taqman® system (PE Applied Biosystems) according to the manufacturer's instructions. These studies demonstrated that TWIK-5 is exclusively expressed in monkey DRG neurons.

For in situ analysis, various tissues obtained from brains, e.g. rat or monkey brains, were first frozen on dry ice. Ten-micrometer-thick coronal sections of the tissues were post-fixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1× SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5\times10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2× SSC. Sections were then sequentially incubated at 37° C. in TNE (a solution containing 10 mM Tris-HCl (pH 7.6), 500 mM NaCl, and 1 mM EDTA), for 10 minutes, in TNE with 10 g of RNase A per ml for 30 minutes, and finally in TNE for 10 minutes. Slides were then rinsed with 2× SSC at room temperature, washed with 2× SSC at 50° C. for 1 hour, washed with 0.2× SSC at 55° C. for 1 hour, and 0.2× SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained. These experiments resulted in the identification of very high levels of TWIK-5 expression in a subpopulation of monkey DRG (small and intermediate size) neurons, and minimal to no expression of TWIK-5 in peripheral tissues. Bright field observation demonstrates that TWIK-5 is expressed in the small diameter neurons that correspond to a subpopulation of nociceptive neurons, and suggests a potential involvement of the gene in the regulation or maintenance of the electrophysiological characteristics of a subpopulation of nociceptive neurons, and thereby in the modulation of pain responses.

Example 2

Expression of Recombinant TWIK-2, TWIK-3, TWIK-4, AND TWIK-5 Protein in Bacterial Cells In this example, TWIK-2, TWIK-3, TWIK-4, and/or TWIK-5 is expressed as a recombinant glutathione-S-transferase (GST) fusion polypeptide in *E. coli* and the fusion polypeptide is isolated and characterized. Specifically, TWIK-2, TWIK-3, TWIK-4, and/or TWIK-5 is fused to GST and this fusion polypeptide is expressed in *E. coli*, e.g., strain PEB 199. Expression of the GST-TWIK-2, GST-TWIK-3, GST-TWIK-4, and/or GST-TWIK-5 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant TWIK-2, TWIK-3, TWIK-4, and TWIK-5 Protein in COS Cells To express the TWIK-2, TWIK-3, TWIK-4, and/or TWIK-5 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire TWIK-2, TWIK-3, TWIK-4, and/or TWIK-5 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the TWIK-2, TWIK-3, TWIK-4, and/or TWIK-5 DNA sequence is amplified by PCR using two primers. The 5' primer contains the restriction site of interest followed by approximately twenty nucleotides of the TWIK-2, TWIK-3, TWIK-4, and/or TWIK-5 coding sequence starting from the initiation codon; the 3' end sequence contains complementary sequences to the other restriction site of interest, a translation stop codon, the HA tag or FLAG tag and the last 20 nucleotides of the TWIK-2, TWIK-3, TWIK-4, and/or TWIK-5 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the TWIK-2, TWIK-3, TWIK-4, and/or TWIK-5 gene is inserted in the correct orientation. The ligation mixture is transformed into *E. coli* cells (strains HB 101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the TWIK-2, TWIK-3, TWIK-4, and/or TWIK-5-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989. The expression of the TWIK-2, TWIK-3, TWIK-4, and/or TWIK-5 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the TWIK-2, TWIK-3, TWIK-4, and/or TWIK-5 coding sequence is cloned directly into the polylinker of the pCDNA/Amp vector using the appropriate restriction sites. The resulting plasmid is transfected into COS cells in the manner described above, and the expression of the TWIK-2, TWIK-3, TWIK-4, and/or TWIK-5 polypeptide is detected by radiolabelling and immunoprecipitation using a TWIK-2, TWIK-3, TWIK-4, and/or TWIK-5 specific monoclonal antibody.

Example 4

Electrophysiological Characterization of TWIK-5

To electrophysiologically characterize the TWIK-5 molecule, the full length human TWIK-5 gene in the pMet7 expression vector was used to transiently transfect CHO cells using lipofectamine.

Figure 21A:
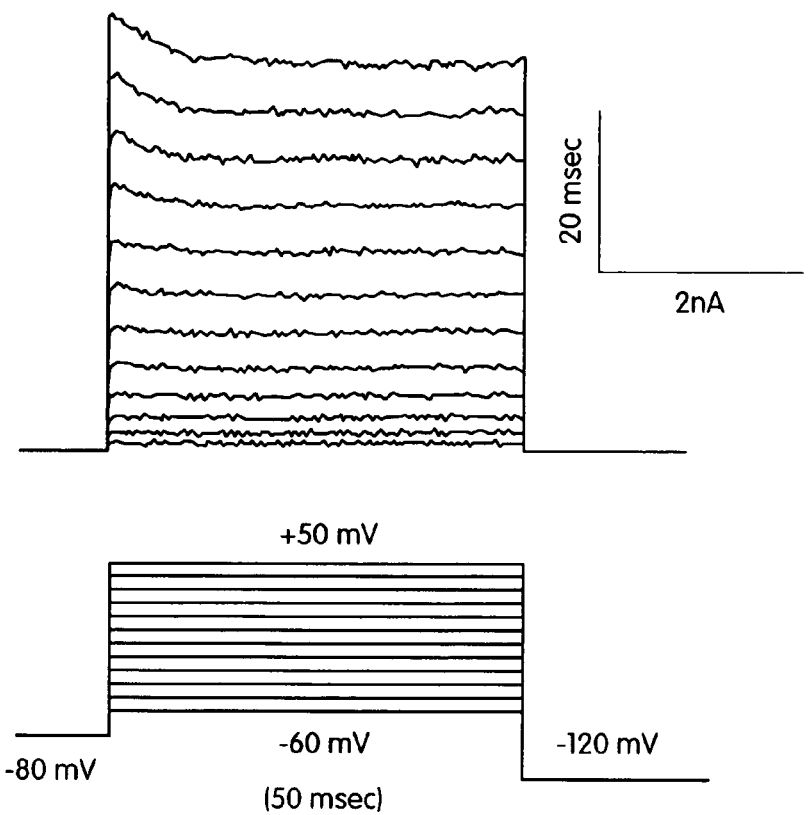
FIG. 21 depicts a recording of the outward currents of TWIK-5 channels in transiently transfected CHO cells recorded under whole-cell patch-clamp. Panel A, lower portion depicts a schematic of the electrophysiological protocol for the experiment (described in Example 4), and the upper portion of Panel A depicts the results of the experiment. Panel B is a graph depicting the relationship between current and membrane potential in TWIK-5 channel activation.
Figure 21B:
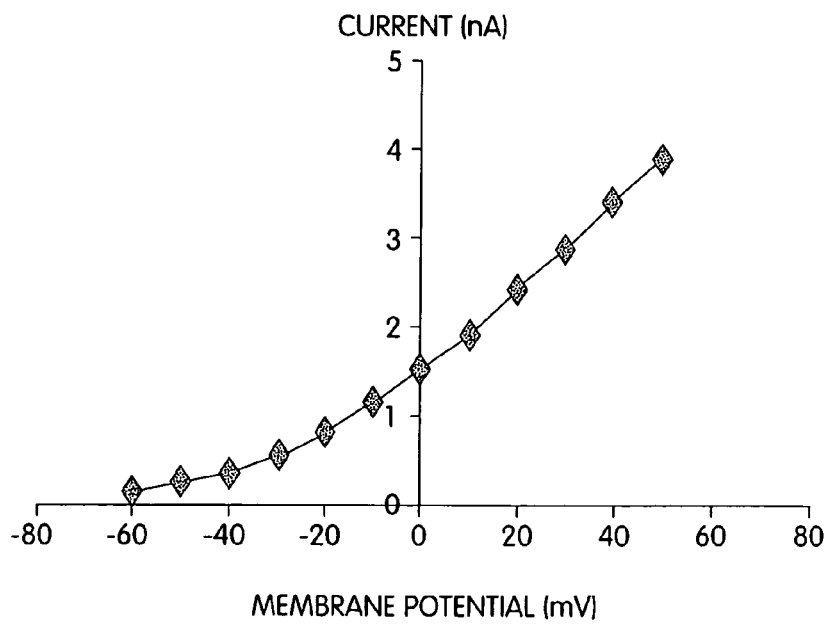

Electrophysiological measurements in the transfected CHO cells were taken using a single electrode patch-clamp, 48 hours after transfection. Cell membrane potentials were held at −8 mV and then depolarized from −60 mV to +50 mV with 10 mV increments for 50 msec, followed by 20 msec hyperpolarization to −120 msec (see FIG. 21A, lower panel). TWIK-5 displayed outward currents from −60 to +50 mV (FIG. 21A, upper panel). The amplitude of current at +50 mV was 4 mA. The current-membrane potential curve was linear from +10 mV to +50 mV (FIG. 21B).

Figure 22A:
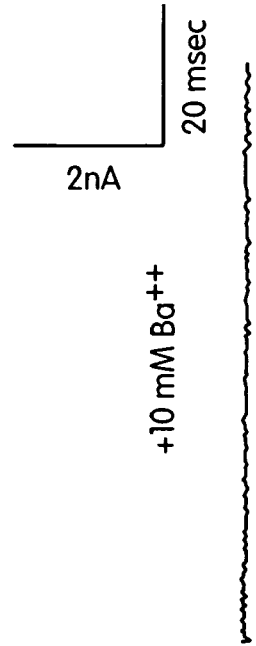
FIG. 22 is a graphical depiction of the results of experiments designed to assess the pharmacological properties of the TWIK-5 channel. The outward currents of TWIK-5 channels in transiently transfected CHO cells under whole-cell patch clamp are shown in Panel A; Panels B-D show similar recordings taken in the presence of 10 mM $Ba^{++}$, 10 mM triethylammonium, and 10 mM 4-aminopyridine, respectively.
Figure 22B:
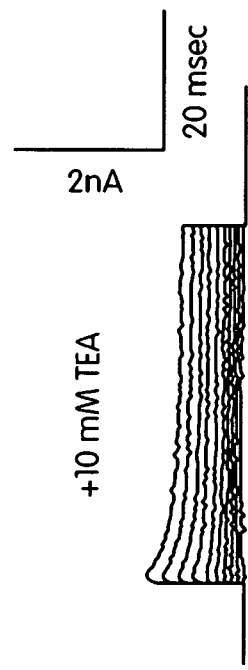
Figure 22C:
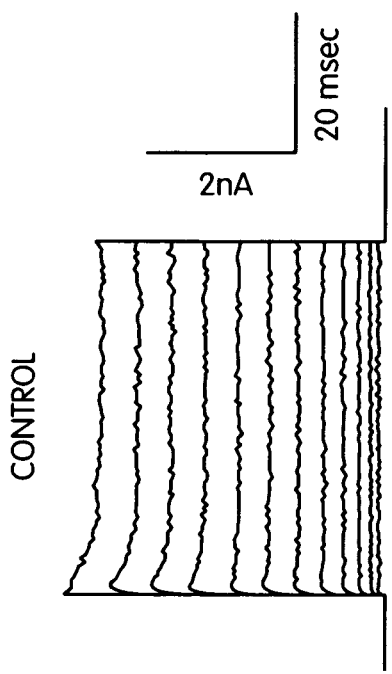
Figure 22D:
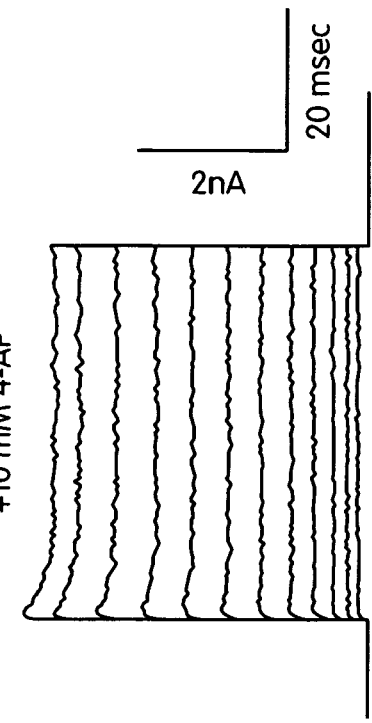

The pharmacological properties of the TWIK-5 channel were studied by incubating a series of known potassium channel inhibitory molecules with the transiently transfected CHO cells, and examining the impact of the molecules upon the conductance of TWIK-5 channels through whole-cell patch-clamp recordings. As shown in FIG. 22, the addition of 10 mM $Ba^{++}$ was completely inhibitory to the function of the TWIK-5 channels (FIG. 22B), and the presence of 10 mM triethylammonium (FIG. 22C) was also significantly inhibitory to TWIK-5 channel conductance, though less so that $Ba^{++}$. The addition of 10 mM 4-aminopyridine, a compound known to be inhibitory to several voltage-gated potassium channels, had no effect on the conductance of the TWIK-5 channel (FIG. 22D).

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound which binds to a polypeptide, comprising:

i) contacting a polypeptide selected from the group consisting of:

a) a polypeptide which is at least 95% identical to the amino acid sequence of SEQ ID NO:11;

b) a polypeptide which is at least 95% identical to the amino acid sequence encoded by the cDNA insert of the plasmid deposited with ATCC as Patent Deposit Number PTA-1640; and c) a polypeptide encoded by a nucleic acid molecule comprising a nucleotide sequence which is at least 95% identical to the nucleotide sequence of SEQ ID NO:10 or SEQ ID NO:12;

with a test compound under conditions suitable for binding; and ii) detecting binding of the test compound to the polypeptide;

thereby identifying a compound which binds to the polypeptide.

2. The method of claim 1, wherein the polypeptide further comprises heterologous sequences.

3. The method of claim 1, wherein the binding of the test compound to the polypeptide is detected by a method selected from the group consisting of:

a) direct detection of test compound/polypeptide binding;

b) a competition binding assay;

c) detecting binding of the test compound to the polypeptide using an antibody; and d) a yeast two-hybrid assay.

4. A method for identifying a compound which binds to a polypeptide, comprising:

i) contacting a polypeptide selected from the group consisting of:

a) a polypeptide comprising the amino acid sequence of SEQ ID NO:11;

b) a polypeptide comprising the amino acid sequence encoded by the cDNA insert of the plasmid deposited with ATCC as Patent Deposit Number PTA-1640; and c) a polypeptide encoded by the nucleotide sequence set forth in SEQ ID NO:10 or SEQ ID NO:12;

with a test compound under conditions suitable for binding; and ii) detecting binding of the test compound to the polypeptide;

thereby identifying a compound which binds to the polypeptide.

5. The method of claim 4, wherein the polypeptide further comprises heterologous sequences.

6. The method of claim 4, wherein the binding of the test compound to the polypeptide is detected by a method selected from the group consisting of:

a) direct detection of test compound/polypeptide binding;

b) a competition binding assay;

c) detecting binding of the test compound to the polypeptide using an antibody; and d) a yeast two-hybrid assay.

* * * * *

UNITED STATES PATENT AND TRADEMARK OFFICE
CERTIFICATE OF CORRECTION

PATENT NO. : 7,517,659 B2 Page 1 of 1
APPLICATION NO. : 10/701013
DATED : April 14, 2009
INVENTOR(S) : Rory A. J. Curtis et al.

It is certified that error appears in the above-identified patent and that said Letters Patent is hereby corrected as shown below:

On the Title Pg, Item (56) under "Other Publications" (Page 2, line 60):
　　　Please replace "Accession No. OMJ001356" with --Accession No. AJ001356--.

Signed and Sealed this

Twenty-ninth Day of September, 2009

David J. Kappos
*Director of the United States Patent and Trademark Office*

SEQUENCE LISTING

```
<160> NUMBER OF SEQ ID NOS: 12

<210> SEQ ID NO 1
<211> LENGTH: 3452
<212> TYPE: DNA
<213> ORGANISM: Homo sapiens
<220> FEATURE:
<221> NAME/KEY: CDS
<222> LOCATION: (10)..(1506)

<400> SEQUENCE: 1
```

```
tcgggagcc atg gtg gac cgg ggc cct ctg ctc acc tcg gcc atc atc ttc              51
         Met Val Asp Arg Gly Pro Leu Leu Thr Ser Ala Ile Ile Phe
         1               5                   10
tac ctg gcc atc ggg gcg gcg atc ttc gaa gtg ctg gag gag cca cac               99
Tyr Leu Ala Ile Gly Ala Ala Ile Phe Glu Val Leu Glu Glu Pro His
15              20                  25                  30
tgg aag gag gcc aag aaa aac tac tac aca cag aag ctg cat ctg ctc              147
Trp Lys Glu Ala Lys Lys Asn Tyr Tyr Thr Gln Lys Leu His Leu Leu
                35                  40                  45
aag gag ttc ccg tgc ctg ggt cag gag ggc ctg gac aag atc cta gag              195
Lys Glu Phe Pro Cys Leu Gly Gln Glu Gly Leu Asp Lys Ile Leu Glu
            50                  55                  60
gtg gta tct gat gct gca gga cag ggt gtg gcc atc aca ggg aac cag              243
Val Val Ser Asp Ala Ala Gly Gln Gly Val Ala Ile Thr Gly Asn Gln
        65                  70                  75
acc ttc aac aac tgg aac tgg ccc aat gca atg att ttt gca gcg acc              291
Thr Phe Asn Asn Trp Asn Trp Pro Asn Ala Met Ile Phe Ala Ala Thr
    80                  85                  90
gtc att acc acc att gga tat ggc aat gtg gct ccc aag acc ccc gcc              339
Val Ile Thr Thr Ile Gly Tyr Gly Asn Val Ala Pro Lys Thr Pro Ala
95                  100                 105                 110
ggt cgc ctc ttc tgt gtt ttc tat ggt ctc ttc ggg gtg ccg ctc tgc              387
Gly Arg Leu Phe Cys Val Phe Tyr Gly Leu Phe Gly Val Pro Leu Cys
                115                 120                 125
ctg acg tgg atc agt gcc ctg ggc aag ttc ttc ggg gga cgt gcc aag              435
Leu Thr Trp Ile Ser Ala Leu Gly Lys Phe Phe Gly Gly Arg Ala Lys
            130                 135                 140
aga cta ggg cag ttc ctt acc aag aga ggt gtg agt ctg cgg aag gcg              483
Arg Leu Gly Gln Phe Leu Thr Lys Arg Gly Val Ser Leu Arg Lys Ala
        145                 150                 155
cag atc acg tgc aca gtc atc ttc atc gtg tgg ggc gtc cta gtc cac              531
Gln Ile Thr Cys Thr Val Ile Phe Ile Val Trp Gly Val Leu Val His
    160                 165                 170
ctg gtg atc cca ccc ttc gta ttc atg gtg act gag ggg tgg aac tac              579
Leu Val Ile Pro Pro Phe Val Phe Met Val Thr Glu Gly Trp Asn Tyr
175                 180                 185                 190
atc gag ggc ctc tac tac tcc ttc atc acc atc tcc acc atc ggc ttc              627
Ile Glu Gly Leu Tyr Tyr Ser Phe Ile Thr Ile Ser Thr Ile Gly Phe
                195                 200                 205
ggt gac ttt gtg gcc ggt gtg aac ccc agc gcc aac tac cac gcc ctg              675
Gly Asp Phe Val Ala Gly Val Asn Pro Ser Ala Asn Tyr His Ala Leu
            210                 215                 220
tac cgc tac ttc gtg gag ctc tgg atc tac ttg ggg ctg gcc tgg ctg              723
Tyr Arg Tyr Phe Val Glu Leu Trp Ile Tyr Leu Gly Leu Ala Trp Leu
        225                 230                 235
tcc ctt ttt gtc aac tgg aag gtg agc atg ttt gtg gaa gtc cac aaa              771
Ser Leu Phe Val Asn Trp Lys Val Ser Met Phe Val Glu Val His Lys
    240                 245                 250
gcc att aag aag cgg cgg cgg cga cgg aag gag tcc ttt gag agc tcc              819
Ala Ile Lys Lys Arg Arg Arg Arg Arg Lys Glu Ser Phe Glu Ser Ser
255                 260                 265                 270
cca cac tcc cgg aag gcc ctg cag gtg aag ggg agc aca gcc tcc aag              867
Pro His Ser Arg Lys Ala Leu Gln Val Lys Gly Ser Thr Ala Ser Lys
                275                 280                 285
gac gtc aac atc ttc agc ttt ctt tcc aag aag gaa gag acc tac aac              915
Asp Val Asn Ile Phe Ser Phe Leu Ser Lys Lys Glu Glu Thr Tyr Asn
            290                 295                 300
gac ctc atc aag cag atc ggg aag aag gcc atg aag aca agc ggg ggt              963
Asp Leu Ile Lys Gln Ile Gly Lys Lys Ala Met Lys Thr Ser Gly Gly
        305                 310                 315
```

```
ggg gag acg ggc ccg ggc cca ggg ctg ggg cct caa ggc ggt ggg ctc      1011
Gly Glu Thr Gly Pro Gly Pro Gly Leu Gly Pro Gln Gly Gly Gly Leu
        320                 325                 330 cca gca ctg ccc cct tcc ctg gtg ccc ctg gta gtc tac tcc aag aac      1059
Pro Ala Leu Pro Pro Ser Leu Val Pro Leu Val Val Tyr Ser Lys Asn
335                 340                 345                 350 cgg gtg ccc acc ttg gaa gag gtg tca cag aca ctg agg agc aaa ggc      1107
Arg Val Pro Thr Leu Glu Glu Val Ser Gln Thr Leu Arg Ser Lys Gly
                355                 360                 365 cac gta tca agg tcc cca gat gag gag gct gtg gca cgg gcc cct gaa      1155
His Val Ser Arg Ser Pro Asp Glu Glu Ala Val Ala Arg Ala Pro Glu
            370                 375                 380 gac agc tcc cct gcc ccc gag gtg ttc atg aac cag ctg gac cgc atc      1203
Asp Ser Ser Pro Ala Pro Glu Val Phe Met Asn Gln Leu Asp Arg Ile
        385                 390                 395 agc gag gaa tgc gag cca tgg gac gcc cag gac tac cac cca ctc atc      1251
Ser Glu Glu Cys Glu Pro Trp Asp Ala Gln Asp Tyr His Pro Leu Ile
400                 405                 410 ttc cag gac gcc agc atc acc ttc gtg aac acg gct ggc ctc tca           1299
Phe Gln Asp Ala Ser Ile Thr Phe Val Asn Thr Ala Gly Leu Ser
415                 420                 425                 430 gac gag gag acc tcc aag tcc tcg cta gag gac aac ttg gca ggg gag      1347
Asp Glu Glu Thr Ser Lys Ser Ser Leu Glu Asp Asn Leu Ala Gly Glu
                435                 440                 445 gag agc ccc cag cag ggg gct gaa gcc aag gcg ccc ctg aac atg ggc      1395
Glu Ser Pro Gln Gln Gly Ala Glu Ala Lys Ala Pro Leu Asn Met Gly
            450                 455                 460 gag ttc ccc tcc tcc tcc gag tcc acc ttc acc agc act gag tct gag      1443
Glu Phe Pro Ser Ser Ser Glu Ser Thr Phe Thr Ser Thr Glu Ser Glu
        465                 470                 475 ctc tct gtg cct tac gaa cag ctg atg aat gag tac aac aag gct aac      1491
Leu Ser Val Pro Tyr Glu Gln Leu Met Asn Glu Tyr Asn Lys Ala Asn
480                 485                 490 agc ccc aag ggc aca tgaggcaggg ccggctcccc accccacctt tgatggcctc     1546
Ser Pro Lys Gly Thr
495 ttcccccctc accctagggt gtcccaagat gaccgggacg cctggcccct ggtgggggg    1606 cagcctcgga actgggagtg gggggccagg ggccttccta accttccatc atcctcagct   1666 agatgtatgc ccgggacagg gcctctgttc tccagctgaa ccatacccctg gctgtgggg   1726 catctgtcct gagcttggct ggtgtatctc acaatgcaaa gacatgctgg ctggcgggac   1786 aggtgggcag gactgaccct gaggaggcct tgcctgcagg gtctttgtct caccatttgg   1846 tggagtatca cacggttctc tgaggtctgg ggcctcagct gtttaagttt accggtatta   1906 ctgagctcgg catttggaga gggagctctg aagtgtctgg ggaggtaccg ctgtgcgtgg   1966 ggtcaggtgt ttccgtacca cagcaggagc agggcctgcc cgcatcccag ctgtgggcct   2026 gccggtcagg tcgggcacct actacaaacc gtagtggggt ggaggctgct ggaggtggga   2086 gtgaggagat gagggcaggg tctcaaacag tcctgactca cagggcctgg aaacaagtcc   2146 tatgtgggcc tggggcctgg ggtcctcatc ctccttgttg gtctactcag gcccagccca   2206 gagctgtgtt ccctgtctca ggtcaagcag tggcagacgc aaggctttct gtgggccccc   2266 aagtggtagg agggagagta gcagagcatg ggttactgga agccgggact gctagggctg   2326 gtggccaggg agctgcaaga gtgaggctca gctctggctg ttctgccct taccctcct    2386 gcccgcctga gaactgcaca ccctgcccgc tggcccagg acctgcactc ccaatcctgc    2446 tgtcttctcc ttccctgtgc cctgaacaag gacctcactg cccgccttcc cctcccacca   2506
```

-continued

```
gccccettgg gccaggcagg gtgaggccaa attgctcttg gcccacaaat gggtgatggt      2566
cagatatgtg aatcaagctc ctttctctag ctagtgtttg atgtgcacgt gtgtgtgcac      2626
agtgcgtgtg tgcacacgca cacctgtgca ctcgtgtgtg tttaagaaag gaaaggattt      2686
gggctgggga gcaaaagata atgtgaaact gttggtggac tctctggtga ggggtgggca      2746
gaacttgctg ctactagagt tcttgggttc tccatgatgt tcaccctggg gctggcccac      2806
tgtgtcctga atgtttttgt tatttttgt tttatttttt aaacaaactg ctgtttttat       2866
atacctggaa tctgttgttg gcttcagagc cagtggttaa agagcagggt cccaaggatt      2926
gggagatcta gtgtctgccc tcctgccctg caactcaatt gggcttttt cggtgacctc       2986 atccaaggcc atgatgtcaa gggccatgtc cccaagcaga ggtggagaag gggacactga      3046
ggtgagcaaa agcaggaagg ggcatccact gcgggtgact ggaggccggg caggaagcaa      3106
gtcatcagag ccgctcagct ccgttcactc tctgccttct gccccactac tgtggggcag      3166
tggggccaga gcccacctcc ccaacatgtg aagacagtga tgggcacgtg cccacacccc      3226
cacttctcta gccgtttgca gaggccgcca cccagcaggg gcctgaaaag gagcagcctc      3286
gtatttttct gtgaaatgtt ttaatgaacc atgttgttgc tggttgtcct ggcatcgcgc      3346
acactgtatg tacatactgg caacgatgtc aaatgtaatt tatttttaaca ttttttacaat   3406 aaaacatgag gtggacaggc caaaaaaaaa aaaaaaaaaa aaaaaa                     3452
```

<210> SEQ ID NO 2
<211> LENGTH: 499
<212> TYPE: PRT
<213> ORGANISM: Homo sapiens

<400> SEQUENCE: 2

```
Met Val Asp Arg Gly Pro Leu Leu Thr Ser Ala Ile Ile Phe Tyr Leu
1               5                   10                  15

Ala Ile Gly Ala Ala Ile Phe Glu Val Leu Glu Pro His Trp Lys
            20                  25                  30

Glu Ala Lys Lys Asn Tyr Tyr Thr Gln Lys Leu His Leu Leu Lys Glu
        35                  40                  45

Phe Pro Cys Leu Gly Gln Glu Gly Leu Asp Lys Ile Leu Glu Val Val
    50                  55                  60

Ser Asp Ala Ala Gly Gln Gly Val Ala Ile Thr Gly Asn Gln Thr Phe
65                  70                  75                  80

Asn Asn Trp Asn Trp Pro Asn Ala Met Ile Phe Ala Ala Thr Val Ile
                85                  90                  95

Thr Thr Ile Gly Tyr Gly Asn Val Ala Pro Lys Thr Pro Ala Gly Arg
            100                 105                 110

Leu Phe Cys Val Phe Tyr Gly Leu Phe Gly Val Pro Leu Cys Leu Thr
        115                 120                 125

Trp Ile Ser Ala Leu Gly Lys Phe Phe Gly Gly Arg Ala Lys Arg Leu
    130                 135                 140

Gly Gln Phe Leu Thr Lys Arg Gly Val Ser Leu Arg Lys Ala Gln Ile
145                 150                 155                 160

Thr Cys Thr Val Ile Phe Ile Val Trp Gly Val Leu Val His Leu Val
                165                 170                 175

Ile Pro Pro Phe Val Phe Met Val Thr Glu Gly Trp Asn Tyr Ile Glu
            180                 185                 190

Gly Leu Tyr Tyr Ser Phe Ile Thr Ile Ser Thr Ile Gly Phe Gly Asp
        195                 200                 205
```

```
Phe Val Ala Gly Val Asn Pro Ser Ala Asn Tyr His Ala Leu Tyr Arg
    210                 215                 220

Tyr Phe Val Glu Leu Trp Ile Tyr Leu Gly Leu Ala Trp Leu Ser Leu
225                 230                 235                 240

Phe Val Asn Trp Lys Val Ser Met Phe Val Glu Val His Lys Ala Ile
                245                 250                 255

Lys Lys Arg Arg Arg Arg Lys Glu Ser Phe Glu Ser Ser Pro His
            260                 265                 270

Ser Arg Lys Ala Leu Gln Val Lys Gly Ser Thr Ala Ser Lys Asp Val
        275                 280                 285

Asn Ile Phe Ser Phe Leu Ser Lys Glu Glu Thr Tyr Asn Asp Leu
    290                 295                 300

Ile Lys Gln Ile Gly Lys Ala Met Lys Thr Ser Gly Gly Gly Glu
305                 310                 315                 320

Thr Gly Pro Gly Pro Gly Leu Gly Pro Gln Gly Gly Leu Pro Ala
                325                 330                 335

Leu Pro Pro Ser Leu Val Pro Leu Val Val Tyr Ser Lys Asn Arg Val
                340                 345                 350

Pro Thr Leu Glu Glu Val Ser Gln Thr Leu Arg Ser Lys Gly His Val
        355                 360                 365

Ser Arg Ser Pro Asp Glu Glu Ala Val Ala Arg Ala Pro Glu Asp Ser
    370                 375                 380

Ser Pro Ala Pro Glu Val Phe Met Asn Gln Leu Asp Arg Ile Ser Glu
385                 390                 395                 400

Glu Cys Glu Pro Trp Asp Ala Gln Asp Tyr His Pro Leu Ile Phe Gln
                405                 410                 415

Asp Ala Ser Ile Thr Phe Val Asn Thr Glu Ala Gly Leu Ser Asp Glu
                420                 425                 430

Glu Thr Ser Lys Ser Ser Leu Glu Asp Asn Leu Ala Gly Glu Glu Ser
        435                 440                 445

Pro Gln Gln Gly Ala Glu Ala Lys Ala Pro Leu Asn Met Gly Glu Phe
    450                 455                 460

Pro Ser Ser Ser Glu Ser Thr Phe Thr Ser Thr Glu Ser Glu Leu Ser
465                 470                 475                 480

Val Pro Tyr Glu Gln Leu Met Asn Glu Tyr Asn Lys Ala Asn Ser Pro
                485                 490                 495

Lys Gly Thr

<210> SEQ ID NO 3
<211> LENGTH: 1497
<212> TYPE: DNA
<213> ORGANISM: Homo sapiens
<220> FEATURE:
<221> NAME/KEY: CDS
<222> LOCATION: (1)..(1497)

<400> SEQUENCE: 3 atg gtg gac cgg ggc cct ctg ctc acc tcg gcc atc atc ttc tac ctg      48
Met Val Asp Arg Gly Pro Leu Leu Thr Ser Ala Ile Ile Phe Tyr Leu
1               5                   10                  15 gcc atc ggg gcg gcg atc ttc gaa gtg ctg gag gag cca cac tgg aag      96
Ala Ile Gly Ala Ala Ile Phe Glu Val Leu Glu Glu Pro His Trp Lys
            20                  25                  30 gag gcc aag aaa aac tac tac aca cag aag ctg cat ctg ctc aag gag    144
Glu Ala Lys Lys Asn Tyr Tyr Thr Gln Lys Leu His Leu Leu Lys Glu
        35                  40                  45
```

-continued

```
ttc ccg tgc ctg ggt cag gag ggc ctg gac aag atc cta gag gtg gta    192
Phe Pro Cys Leu Gly Gln Glu Gly Leu Asp Lys Ile Leu Glu Val Val
     50                  55                  60 tct gat gct gca gga cag ggt gtg gcc atc aca ggg aac cag acc ttc    240
Ser Asp Ala Ala Gly Gln Gly Val Ala Ile Thr Gly Asn Gln Thr Phe
 65                  70                  75                  80 aac aac tgg aac tgg ccc aat gca atg att ttt gcg acg gtc att        288
Asn Asn Trp Asn Trp Pro Asn Ala Met Ile Phe Ala Ala Thr Val Ile
                 85                  90                  95 acc acc att gga tat ggc aat gtg gct ccc aag acc ccc gcc ggt cgc    336
Thr Thr Ile Gly Tyr Gly Asn Val Ala Pro Lys Thr Pro Ala Gly Arg
            100                 105                 110 ctc ttc tgt gtt ttc tat ggt ctc ttc ggg gtg ccg ctc tgc ctg acg    384
Leu Phe Cys Val Phe Tyr Gly Leu Phe Gly Val Pro Leu Cys Leu Thr
        115                 120                 125 tgg atc agt gcc ctg ggc aag ttc ttc ggg gga cgt gcc aag aga cta    432
Trp Ile Ser Ala Leu Gly Lys Phe Phe Gly Gly Arg Ala Lys Arg Leu
    130                 135                 140 ggg cag ttc ctt acc aag aga ggt gtg agt ctg cgg aag gcg cag atc    480
Gly Gln Phe Leu Thr Lys Arg Gly Val Ser Leu Arg Lys Ala Gln Ile
145                 150                 155                 160 acg tgc aca gtc atc ttc atc gtg tgg ggc gtc cta gtc cac ctg gtg    528
Thr Cys Thr Val Ile Phe Ile Val Trp Gly Val Leu Val His Leu Val
                165                 170                 175 atc cca ccc ttc gta ttc atg gtg act gag ggg tgg aac tac atc gag    576
Ile Pro Pro Phe Val Phe Met Val Thr Glu Gly Trp Asn Tyr Ile Glu
            180                 185                 190 ggc ctc tac tac tcc ttc atc acc atc tcc acc atc ggc ttc ggt gac    624
Gly Leu Tyr Tyr Ser Phe Ile Thr Ile Ser Thr Ile Gly Phe Gly Asp
        195                 200                 205 ttt gtg gcc ggt gtg aac ccc agc gcc aac tac cac gcc ctg tac cgc    672
Phe Val Ala Gly Val Asn Pro Ser Ala Asn Tyr His Ala Leu Tyr Arg
    210                 215                 220 tac ttc gtg gag ctc tgg atc tac ttg ggg ctg gcc tgg ctg tcc ctt    720
Tyr Phe Val Glu Leu Trp Ile Tyr Leu Gly Leu Ala Trp Leu Ser Leu
225                 230                 235                 240 ttt gtc aac tgg aag gtg agc atg ttt gtg gaa gtc cac aaa gcc att    768
Phe Val Asn Trp Lys Val Ser Met Phe Val Glu Val His Lys Ala Ile
                245                 250                 255 aag aag cgg cgg cgg cga cgg aag gag tcc ttt gag agc tcc cca cac    816
Lys Lys Arg Arg Arg Arg Arg Lys Glu Ser Phe Glu Ser Ser Pro His
            260                 265                 270 tcc cgg aag gcc ctg cag gtg aag ggg agc aca gcc tcc aag gac gtc    864
Ser Arg Lys Ala Leu Gln Val Lys Gly Ser Thr Ala Ser Lys Asp Val
        275                 280                 285 aac atc ttc agc ttt ctt tcc aag aag gaa gag acc tac aac gac ctc    912
Asn Ile Phe Ser Phe Leu Ser Lys Lys Glu Glu Thr Tyr Asn Asp Leu
    290                 295                 300 atc aag cag atc ggg aag aag gcc atg aag aca agc ggg ggt ggg gag    960
Ile Lys Gln Ile Gly Lys Lys Ala Met Lys Thr Ser Gly Gly Gly Glu
305                 310                 315                 320 acg ggc ccg ggc cca ggg ctg ggg cct caa ggc ggt ggg ctc cca gca   1008
Thr Gly Pro Gly Pro Gly Leu Gly Pro Gln Gly Gly Gly Leu Pro Ala
                325                 330                 335 ctg ccc cct tcc ctg gtg ccc ctg gta gtc tac tcc aag aac cgg gtg   1056
Leu Pro Pro Ser Leu Val Pro Leu Val Val Tyr Ser Lys Asn Arg Val
            340                 345                 350 ccc acc ttg gaa gag gtg tca cag aca ctg agg agc aaa ggc cac gta   1104
Pro Thr Leu Glu Glu Val Ser Gln Thr Leu Arg Ser Lys Gly His Val
```

-continued

```
            355                 360                 365
tca agg tcc cca gat gag gag gct gtg gca cgg gcc cct gaa gac agc    1152
Ser Arg Ser Pro Asp Glu Glu Ala Val Ala Arg Ala Pro Glu Asp Ser
    370                 375                 380 tcc cct gcc ccc gag gtg ttc atg aac cag ctg gac cgc atc agc gag    1200
Ser Pro Ala Pro Glu Val Phe Met Asn Gln Leu Asp Arg Ile Ser Glu
385                 390                 395                 400 gaa tgc gag cca tgg gac gcc cag gac tac cac cca ctc atc ttc cag    1248
Glu Cys Glu Pro Trp Asp Ala Gln Asp Tyr His Pro Leu Ile Phe Gln
                405                 410                 415 gac gcc agc atc acc ttc gtg aac acg gag gct ggc ctc tca gac gag    1296
Asp Ala Ser Ile Thr Phe Val Asn Thr Glu Ala Gly Leu Ser Asp Glu
            420                 425                 430 gag acc tcc aag tcc tcg cta gag gac aac ttg gca ggg gag gag agc    1344
Glu Thr Ser Lys Ser Ser Leu Glu Asp Asn Leu Ala Gly Glu Glu Ser
        435                 440                 445 ccc cag cag ggg gct gaa gcc aag gcg ccc ctg aac atg ggc gag ttc    1392
Pro Gln Gln Gly Ala Glu Ala Lys Ala Pro Leu Asn Met Gly Glu Phe
    450                 455                 460 ccc tcc tcc tcc gag tcc acc ttc acc agc act gag tct gag ctc tct    1440
Pro Ser Ser Ser Glu Ser Thr Phe Thr Ser Thr Glu Ser Glu Leu Ser
465                 470                 475                 480 gtg cct tac gaa cag ctg atg aat gag tac aac aag gct aac agc ccc    1488
Val Pro Tyr Glu Gln Leu Met Asn Glu Tyr Asn Lys Ala Asn Ser Pro
                485                 490                 495 aag ggc aca                                                         1497
Lys Gly Thr <210> SEQ ID NO 4
<211> LENGTH: 1575
<212> TYPE: DNA
<213> ORGANISM: Homo sapiens
<220> FEATURE:
<221> NAME/KEY: CDS
<222> LOCATION: (122)..(1117)

<400> SEQUENCE: 4
caacgcgtcc gccgggcacc agcaggcgtt tgcgagagga gatacgagct ggacgcctgg    60
cccttccctc ccaccgggtc ctagtccacc gctcccggcg ccggctcccc gctctcccgc   120 t atg tac cga ccg cga gcc cgg gcg gct ccc gag ggc agg gtc cgg ggc   169
  Met Tyr Arg Pro Arg Ala Arg Ala Ala Pro Glu Gly Arg Val Arg Gly
  1               5                  10                  15 tgc gcg gtg ccc ggc acc gtg ctc ctg ctg ctc gcc tac ctg gct tac    217
Cys Ala Val Pro Gly Thr Val Leu Leu Leu Leu Ala Tyr Leu Ala Tyr
            20                  25                  30 ctg gcg ctg ggc acc ggc gtg ttc tgg acg ctg gag ggc cgc gcg gcg    265
Leu Ala Leu Gly Thr Gly Val Phe Trp Thr Leu Glu Gly Arg Ala Ala
        35                  40                  45 cag gac tcc agc cgc agc ttc cag cgc gac aag tgg gag ctg ttg cag    313
Gln Asp Ser Ser Arg Ser Phe Gln Arg Asp Lys Trp Glu Leu Leu Gln
    50                  55                  60 aac ttc acg tgt ctg gac cgc ccg gcg ctg gac tcg ctg atc cgg gat    361
Asn Phe Thr Cys Leu Asp Arg Pro Ala Leu Asp Ser Leu Ile Arg Asp
65                  70                  75                  80 gtc gtc caa gca tac aaa aac gga gcc agc ctc ctc agc aac acc acc    409
Val Val Gln Ala Tyr Lys Asn Gly Ala Ser Leu Leu Ser Asn Thr Thr
                85                  90                  95 agc atg ggg cgc tgg gag ctc gtg ggc tcc ttc ttc ttt tct gtg tcc    457
Ser Met Gly Arg Trp Glu Leu Val Gly Ser Phe Phe Phe Ser Val Ser
            100                 105                 110
```

```
acc atc acc acc att ggc tat ggc aac ctg agc ccc aac acg atg gct    505
Thr Ile Thr Thr Ile Gly Tyr Gly Asn Leu Ser Pro Asn Thr Met Ala
        115                 120                 125 gcc cgc ctc ttc tgc atc ttc ttt gcc ctt gtg ggg atc cca ctc aac    553
Ala Arg Leu Phe Cys Ile Phe Phe Ala Leu Val Gly Ile Pro Leu Asn
130                 135                 140 ctc gtg gtg ctc aac cga ctg ggg cat ctc atg cag cag gga gta aac    601
Leu Val Val Leu Asn Arg Leu Gly His Leu Met Gln Gln Gly Val Asn
145                 150                 155                 160 cac tgg gcc agc agg ctg ggg ggc acc tgg cag gat cct gac aag gcg    649
His Trp Ala Ser Arg Leu Gly Gly Thr Trp Gln Asp Pro Asp Lys Ala
                165                 170                 175 cgg tgg ctg gcg ggc tct ggc gcc ctc ctc tcg ggc ctc ctg ctc ttc    697
Arg Trp Leu Ala Gly Ser Gly Ala Leu Leu Ser Gly Leu Leu Leu Phe
            180                 185                 190 ctg ctg ctg cca ccg ctg ctc ttc tcc cac atg gag ggc tgg agc tac    745
Leu Leu Leu Pro Pro Leu Leu Phe Ser His Met Glu Gly Trp Ser Tyr
        195                 200                 205 aca gag ggc ttc tac ttc gcc ttc atc acc ctc agc acc gtg ggc ttc    793
Thr Glu Gly Phe Tyr Phe Ala Phe Ile Thr Leu Ser Thr Val Gly Phe
    210                 215                 220 ggc gac tac gtg att gga atg aac ccc tcc cag agg tac cca ctg tgg    841
Gly Asp Tyr Val Ile Gly Met Asn Pro Ser Gln Arg Tyr Pro Leu Trp
225                 230                 235                 240 tac aag aac atg gtg tcc ctg tgg atc ctc ttt ggg atg gca tgg ctg    889
Tyr Lys Asn Met Val Ser Leu Trp Ile Leu Phe Gly Met Ala Trp Leu
                245                 250                 255 gcc ttg atc atc aaa ctc atc ctc tcc cag ctg gag acg cca ggg agg    937
Ala Leu Ile Ile Lys Leu Ile Leu Ser Gln Leu Glu Thr Pro Gly Arg
            260                 265                 270 gta tgt tcc tgc tgc cac cac agc tct aag gaa gac ttc aag tcc caa    985
Val Cys Ser Cys Cys His His Ser Ser Lys Glu Asp Phe Lys Ser Gln
        275                 280                 285 agc tgg aga cag gga cct gac cgg gag cca gag tcc cac tcc cca cag   1033
Ser Trp Arg Gln Gly Pro Asp Arg Glu Pro Glu Ser His Ser Pro Gln
    290                 295                 300 caa gga tgc tat cca gag gga ccc atg gga atc ata cag cat ctg gaa   1081
Gln Gly Cys Tyr Pro Glu Gly Pro Met Gly Ile Ile Gln His Leu Glu
305                 310                 315                 320 cct tct gct cac gct gca ggc tgt ggc aag gac agc tagttatact        1127
Pro Ser Ala His Ala Ala Gly Cys Gly Lys Asp Ser
                325                 330 ccattctttg gtcgtcgtcc tcggtagcaa gaccctgat tttaagcttt gcacatgtcc   1187
acccaaacta aagactacat tttccatcca ccctagaggc tgggtgcagc tatatgatta  1247
attctgccca ataggtata cagagacatg tcctgggtga catgggatgt gactttcggg   1307
tgtcggggca gcatgccctt ctcccccact tccttacttt agcgggctgc aatgccgccg  1367
atatgatggc tgggagctct ggcagccata cggcaccatg aagtagcggc aatgtttgag  1427
cggcacaata agataggaag agtctggatc tctgatgatc acagagccat cctaacaaac  1487
ggaatatcac ccgacctcct ttatgtgaga gagaaataaa catcttatgt aaaatacaaa  1547
aaaaaaaaaa aaaaaaaagg gcggccgc                                    1575

<210> SEQ ID NO 5
<211> LENGTH: 332
<212> TYPE: PRT
<213> ORGANISM: Homo sapiens
```

```
<400> SEQUENCE: 5

Met Tyr Arg Pro Arg Ala Arg Ala Ala Pro Glu Gly Arg Val Arg Gly
 1               5                  10                  15

Cys Ala Val Pro Gly Thr Val Leu Leu Leu Ala Tyr Leu Ala Tyr
            20                  25                  30

Leu Ala Leu Gly Thr Gly Val Phe Trp Thr Leu Glu Gly Arg Ala Ala
        35                  40                  45

Gln Asp Ser Ser Arg Ser Phe Gln Arg Asp Lys Trp Glu Leu Leu Gln
    50                  55                  60

Asn Phe Thr Cys Leu Asp Arg Pro Ala Leu Asp Ser Leu Ile Arg Asp
 65                  70                  75                  80

Val Val Gln Ala Tyr Lys Asn Gly Ala Ser Leu Leu Ser Asn Thr Thr
                85                  90                  95

Ser Met Gly Arg Trp Glu Leu Val Gly Ser Phe Phe Ser Val Ser
            100                 105                 110

Thr Ile Thr Thr Ile Gly Tyr Gly Asn Leu Ser Pro Asn Thr Met Ala
        115                 120                 125

Ala Arg Leu Phe Cys Ile Phe Phe Ala Leu Val Gly Ile Pro Leu Asn
    130                 135                 140

Leu Val Val Leu Asn Arg Leu Gly His Leu Met Gln Gln Gly Val Asn
145                 150                 155                 160

His Trp Ala Ser Arg Leu Gly Gly Thr Trp Gln Asp Pro Asp Lys Ala
                165                 170                 175

Arg Trp Leu Ala Gly Ser Gly Ala Leu Leu Ser Gly Leu Leu Leu Phe
            180                 185                 190

Leu Leu Leu Pro Pro Leu Leu Phe Ser His Met Glu Gly Trp Ser Tyr
        195                 200                 205

Thr Glu Gly Phe Tyr Phe Ala Phe Ile Thr Leu Ser Thr Val Gly Phe
    210                 215                 220

Gly Asp Tyr Val Ile Gly Met Asn Pro Ser Gln Arg Tyr Pro Leu Trp
225                 230                 235                 240

Tyr Lys Asn Met Val Ser Leu Trp Ile Leu Phe Gly Met Ala Trp Leu
                245                 250                 255

Ala Leu Ile Ile Lys Leu Ile Leu Ser Gln Leu Glu Thr Pro Gly Arg
            260                 265                 270

Val Cys Ser Cys Cys His His Ser Ser Lys Glu Asp Phe Lys Ser Gln
        275                 280                 285

Ser Trp Arg Gln Gly Pro Asp Arg Glu Pro Glu Ser His Ser Pro Gln
    290                 295                 300

Gln Gly Cys Tyr Pro Glu Gly Pro Met Gly Ile Ile Gln His Leu Glu
305                 310                 315                 320

Pro Ser Ala His Ala Ala Gly Cys Gly Lys Asp Ser
                325                 330

<210> SEQ ID NO 6
<211> LENGTH: 996
<212> TYPE: DNA
<213> ORGANISM: Homo sapiens
<220> FEATURE:
<221> NAME/KEY: CDS
<222> LOCATION: (1)..(996)

<400> SEQUENCE: 6 atg tac cga ccg cga gcc cgg gcg gct ccc gag ggc agg gtc cgg ggc     48
Met Tyr Arg Pro Arg Ala Arg Ala Ala Pro Glu Gly Arg Val Arg Gly
 1               5                  10                  15
```

-continued

| | | |
|---|---|---|
| tgc gcg gtg ccc ggc acc gtg ctc ctg ctg ctc gcc tac ctg gct tac<br>Cys Ala Val Pro Gly Thr Val Leu Leu Leu Leu Ala Tyr Leu Ala Tyr<br>20                                 25                          30 | 96 |
| ctg gcg ctg ggc acc ggc gtg ttc tgg acg ctg gag ggc cgc gcg gcg<br>Leu Ala Leu Gly Thr Gly Val Phe Trp Thr Leu Glu Gly Arg Ala Ala<br>35                                40                          45 | 144 |
| cag gac tcc agc cgc agc ttc cag cgc gac aag tgg gag ctg ttg cag<br>Gln Asp Ser Ser Arg Ser Phe Gln Arg Asp Lys Trp Glu Leu Leu Gln<br>50                                 55                          60 | 192 |
| aac ttc acg tgt ctg gac cgc ccg gcg ctg gac tcg ctg atc cgg gat<br>Asn Phe Thr Cys Leu Asp Arg Pro Ala Leu Asp Ser Leu Ile Arg Asp<br>65                            70                              75                          80 | 240 |
| gtc gtc caa gca tac aaa aac gga gcc agc ctc ctc agc aac acc acc<br>Val Val Gln Ala Tyr Lys Asn Gly Ala Ser Leu Leu Ser Asn Thr Thr<br>                       85                                90                          95 | 288 |
| agc atg ggg cgc tgg gag ctc gtg ggc tcc ttc ttc ttt tct gtg tcc<br>Ser Met Gly Arg Trp Glu Leu Val Gly Ser Phe Phe Phe Ser Val Ser<br>                     100                             105                       110 | 336 |
| acc atc acc acc att ggc tat ggc aac ctg agc ccc aac acg atg gct<br>Thr Ile Thr Thr Ile Gly Tyr Gly Asn Leu Ser Pro Asn Thr Met Ala<br>                  115                         120                       125 | 384 |
| gcc cgc ctc ttc tgc atc ttc ttt gcc ctt gtg ggg atc cca ctc aac<br>Ala Arg Leu Phe Cys Ile Phe Phe Ala Leu Val Gly Ile Pro Leu Asn<br>130                             135                         140 | 432 |
| ctc gtg gtg ctc aac cga ctg ggg cat ctc atg cag cag gga gta aac<br>Leu Val Val Leu Asn Arg Leu Gly His Leu Met Gln Gln Gly Val Asn<br>145                           150                         155                       160 | 480 |
| cac tgg gcc agc agg ctg ggg ggc acc tgg cag gat cct gac aag gcg<br>His Trp Ala Ser Arg Leu Gly Gly Thr Trp Gln Asp Pro Asp Lys Ala<br>                             165                         170                       175 | 528 |
| cgg tgg ctg gcg ggc tct ggc gcc ctc ctc tcg ggc ctc ctg ctc ttc<br>Arg Trp Leu Ala Gly Ser Gly Ala Leu Leu Ser Gly Leu Leu Leu Phe<br>                  180                         185                       190 | 576 |
| ctg ctg ctg cca ccg ctg ctc ttc tcc cac atg gag ggc tgg agc tac<br>Leu Leu Leu Pro Pro Leu Leu Phe Ser His Met Glu Gly Trp Ser Tyr<br>195                           200                       205 | 624 |
| aca gag ggc ttc tac ttc gcc ttc atc acc ctc agc acc gtg ggc ttc<br>Thr Glu Gly Phe Tyr Phe Ala Phe Ile Thr Leu Ser Thr Val Gly Phe<br>210                           215                       220 | 672 |
| ggc gac tac gtg att gga atg aac ccc tcc cag agg tac cca ctg tgg<br>Gly Asp Tyr Val Ile Gly Met Asn Pro Ser Gln Arg Tyr Pro Leu Trp<br>225                           230                       235                       240 | 720 |
| tac aag aac atg gtg tcc ctg tgg atc ctc ttt ggg atg gca tgg ctg<br>Tyr Lys Asn Met Val Ser Leu Trp Ile Leu Phe Gly Met Ala Trp Leu<br>                           245                         250                       255 | 768 |
| gcc ttg atc atc aaa ctc atc ctc tcc cag ctg gag acg cca ggg agg<br>Ala Leu Ile Ile Lys Leu Ile Leu Ser Gln Leu Glu Thr Pro Gly Arg<br>                  260                         265                       270 | 816 |
| gta tgt tcc tgc tgc cac cac agc tct aag gaa gac ttc aag tcc caa<br>Val Cys Ser Cys Cys His His Ser Ser Lys Glu Asp Phe Lys Ser Gln<br>                275                         280                       285 | 864 |
| agc tgg aga cag gga cct gac cgg gag cca gag tcc cac tcc cca cag<br>Ser Trp Arg Gln Gly Pro Asp Arg Glu Pro Glu Ser His Ser Pro Gln<br>290                           295                       300 | 912 |
| caa gga tgc tat cca gag gga ccc atg gga atc ata cag cat ctg gaa<br>Gln Gly Cys Tyr Pro Glu Gly Pro Met Gly Ile Ile Gln His Leu Glu<br>305                         310                       315                   320 | 960 |
| cct tct gct cac gct gca ggc tgt ggc aag gac agc<br>Pro Ser Ala His Ala Ala Gly Cys Gly Lys Asp Ser | 996 |

```
               325                 330

<210> SEQ ID NO 7
<211> LENGTH: 2287
<212> TYPE: DNA
<213> ORGANISM: Homo sapiens
<220> FEATURE:
<221> NAME/KEY: CDS
<222> LOCATION: (136)..(1074)

<400> SEQUENCE: 7
taaaagctgc ggaattctaa tatcactcac tatagggagt cgacccacgc gtccgggaac      60
taggtgccag acggtccgga ggcgggggcc acgtcagcgg ggccacccag ggctcgcggg     120
gtcccggtgg gtgcc atg cgg agg ggc gcg ctt ctg gcg ggc gcc ttg gcc     171
                Met Arg Arg Gly Ala Leu Leu Ala Gly Ala Leu Ala
                  1               5                  10 gcg tac gcc gcg tac ctg gtg ctg ggc gcg ctg ttg gtg gcg cgg ctg     219
Ala Tyr Ala Ala Tyr Leu Val Leu Gly Ala Leu Leu Val Ala Arg Leu
         15                  20                  25 gag ggg ccg cac gaa gcc agg ctc cga gcc gag ctg gag acg ctg cgg     267
Glu Gly Pro His Glu Ala Arg Leu Arg Ala Glu Leu Glu Thr Leu Arg
     30                  35                  40 gcg cag ctg ctt cag cgc agc ccg tgt gtg gct gcc ccc gcc ctg gac     315
Ala Gln Leu Leu Gln Arg Ser Pro Cys Val Ala Ala Pro Ala Leu Asp
 45                  50                  55                  60 gcc ttc gtg gag cga gtg ctg gcg gcc gga cgg ctg ggg cgg gtc gtg     363
Ala Phe Val Glu Arg Val Leu Ala Ala Gly Arg Leu Gly Arg Val Val
                 65                  70                  75 ctt gct aac gct tcg ggg tcc gcc aac gcc tcg gac ccc gcc tgg gac     411
Leu Ala Asn Ala Ser Gly Ser Ala Asn Ala Ser Asp Pro Ala Trp Asp
             80                  85                  90 ttc gcc tct gct ctc ttc ttc gcc agc acg ctg atc acc acc gtg ggc     459
Phe Ala Ser Ala Leu Phe Phe Ala Ser Thr Leu Ile Thr Thr Val Gly
         95                 100                 105 tat ggg tac aca acg cca ctg act gat gcg ggc aag gcc ttc tcc atc     507
Tyr Gly Tyr Thr Thr Pro Leu Thr Asp Ala Gly Lys Ala Phe Ser Ile
    110                 115                 120 gcc ttt gcg ctc ctg ggc gtg ccg acc acc atg ctg ctg acc gcc     555
Ala Phe Ala Leu Leu Gly Val Pro Thr Thr Met Leu Leu Thr Ala
125                 130                 135                 140 tca gcc cag cgc ctg tca ctg ctg ctg act cac gtg ccc ctg tct tgg     603
Ser Ala Gln Arg Leu Ser Leu Leu Leu Thr His Val Pro Leu Ser Trp
                145                 150                 155 ctg agc atg cgt tgg ggc tgg gac ccc cgg cgg gcg gcc tgc tgg cac     651
Leu Ser Met Arg Trp Gly Trp Asp Pro Arg Arg Ala Ala Cys Trp His
            160                 165                 170 ttg gtg gcc ctg ttg ggg gtc gta gtg acc gtc tgc ttt ctg gtg ccg     699
Leu Val Ala Leu Leu Gly Val Val Val Thr Val Cys Phe Leu Val Pro
        175                 180                 185 gct gtg atc ttt gcc cac ctc gag gag gcc tgg agc ttc ttg gat gcc     747
Ala Val Ile Phe Ala His Leu Glu Glu Ala Trp Ser Phe Leu Asp Ala
    190                 195                 200 ttc tac ttc tgc ttt atc tct ctg tcc acc atc ggc ctg ggc gac tac     795
Phe Tyr Phe Cys Phe Ile Ser Leu Ser Thr Ile Gly Leu Gly Asp Tyr
205                 210                 215                 220 gtg ccc ggg gag gcc cct ggc cag ccc tac cgg gcc ctc tac aag gtg     843
Val Pro Gly Glu Ala Pro Gly Gln Pro Tyr Arg Ala Leu Tyr Lys Val
                225                 230                 235 ctg gtc aca gtc tac ctc ttc ctg ggc ctg gtg gcc atg gtg ctg gtg     891
Leu Val Thr Val Tyr Leu Phe Leu Gly Leu Val Ala Met Val Leu Val
```

```
                    240                 245                 250
ctg cag acc ttc cgc cac gtg tcc gac ctc cac ggc ctc acg gag ctc      939
Leu Gln Thr Phe Arg His Val Ser Asp Leu His Gly Leu Thr Glu Leu
            255                 260                 265 atc ctg ctg ccc cct ccg tgc cct gcc agt ttc aat gcg gat gag gac      987
Ile Leu Leu Pro Pro Pro Cys Pro Ala Ser Phe Asn Ala Asp Glu Asp
270                 275                 280 gat cgg gtg gac atc ctg ggc ccc cag ccg gag tcg cac cag caa ctc     1035
Asp Arg Val Asp Ile Leu Gly Pro Gln Pro Glu Ser His Gln Gln Leu
285                 290                 295                 300 tct gcc agc tcc cac acc gac tac gct tcc atc ccc agg tagctggggc      1084
Ser Ala Ser Ser His Thr Asp Tyr Ala Ser Ile Pro Arg
                305                 310 agcctctgcc aggcttgggt gtgcctggcc tgggactgag gggtccaggc gaccagagct   1144
ggctgtacag gaatgtccac gagcacagca ggtgatcttg aggccttgcc gtccaccgtc   1204
tctcctttgt ttcccagcat ctggctggga tgtgaagggc agcactccct gtccccatgt   1264
cccgggctcc actgggcacc aacataacct tgttctctgt cctttctctc atcctcttta   1324
cactgtgtct ctctggctct ctggcattct cgctgcctct gtctttccct cttgctgtct   1384
ctggttctca ttctctttca tgttccgkct gkgtctctca attaaccact cgtcaactgc   1444
tgattctact gggctgtggg ctcagacctc atttcaggca ccagattggt cgctacaccc   1504
tggacaagtg actgcccgtc tctgagcctt gatttcctca gctgccaaat gggaagaata   1564
gaagaatttg cccctaaacc cctcctgtgt gctggccctg tgctagacag tgctggagac   1624
atagttgggg gtggagaact gcccttatgg agcttgcagt ccagtgaggt ggacagacct   1684
gtccccagac agtgatggcc caaaatggtc aggactttaa tggaggargt gaaggtgttg   1744
aaagcacagg cagagtgggt caggkcttga agtcgkagaa gcatargggv ctaggcccaa   1804
tccangcctg gaaaagtmmg ggagngacnt tcctagagga acgggacatc gaactaaaga   1864
cctgaancta tgagaaatag gcaggaagaa gttgtaccnt gactcatttt tttcaggtgt   1924
ctccagggag caggacccat ggagggaccc ctggtgtagg chtggccaga tagactcttc   1984
actcagcagc ctggcaggca ggaarcagwc ataggmcccc agcccagaty tgaatggcmy   2044
sggaggtgct gcccttwccc rtgacaccat tgwaagwgct gyccacatwt gtatgktgtg   2104
ccctggaant cagccaggtt gagctcaaat cccaacttag ccasgtctgg cctgtgtcct   2164
tgggcagtca cactacctct ctgattttgt ttcmwwaatc atgtaaaatg gtgatcatca   2224
taatacaact tcaaaggaa aaaaaaaaaa aaaaaaaaa aaaagggcgg ccgctagact    2284
agt                                                                2287

<210> SEQ ID NO 8
<211> LENGTH: 313
<212> TYPE: PRT
<213> ORGANISM: Homo sapiens

<400> SEQUENCE: 8

Met Arg Arg Gly Ala Leu Leu Ala Gly Ala Leu Ala Ala Tyr Ala Ala
1               5                   10                  15

Tyr Leu Val Leu Gly Ala Leu Val Ala Arg Leu Glu Gly Pro His
            20                  25                  30

Glu Ala Arg Leu Arg Ala Glu Leu Glu Thr Leu Arg Ala Gln Leu Leu
        35                  40                  45

Gln Arg Ser Pro Cys Val Ala Pro Ala Leu Asp Ala Phe Val Glu
    50                  55                  60
```

```
Arg Val Leu Ala Ala Gly Arg Leu Gly Arg Val Val Leu Ala Asn Ala
 65                  70                  75                  80

Ser Gly Ser Ala Asn Ala Ser Asp Pro Ala Trp Asp Phe Ala Ser Ala
             85                  90                  95

Leu Phe Phe Ala Ser Thr Leu Ile Thr Thr Val Gly Tyr Gly Tyr Thr
            100                 105                 110

Thr Pro Leu Thr Asp Ala Gly Lys Ala Phe Ser Ile Ala Phe Ala Leu
        115                 120                 125

Leu Gly Val Pro Thr Thr Met Leu Leu Leu Thr Ala Ser Ala Gln Arg
    130                 135                 140

Leu Ser Leu Leu Leu Thr His Val Pro Leu Ser Trp Leu Ser Met Arg
145                 150                 155                 160

Trp Gly Trp Asp Pro Arg Arg Ala Ala Cys Trp His Leu Val Ala Leu
                165                 170                 175

Leu Gly Val Val Val Thr Val Cys Phe Leu Val Pro Ala Val Ile Phe
            180                 185                 190

Ala His Leu Glu Glu Ala Trp Ser Phe Leu Asp Ala Phe Tyr Phe Cys
        195                 200                 205

Phe Ile Ser Leu Ser Thr Ile Gly Leu Gly Asp Tyr Val Pro Gly Glu
    210                 215                 220

Ala Pro Gly Gln Pro Tyr Arg Ala Leu Tyr Lys Val Leu Val Thr Val
225                 230                 235                 240

Tyr Leu Phe Leu Gly Leu Val Ala Met Val Leu Val Leu Gln Thr Phe
                245                 250                 255

Arg His Val Ser Asp Leu His Gly Leu Thr Glu Leu Ile Leu Leu Pro
            260                 265                 270

Pro Pro Cys Pro Ala Ser Phe Asn Ala Asp Glu Asp Arg Val Asp
        275                 280                 285

Ile Leu Gly Pro Gln Pro Glu Ser His Gln Leu Ser Ala Ser Ser
    290                 295                 300

His Thr Asp Tyr Ala Ser Ile Pro Arg
305                 310

<210> SEQ ID NO 9
<211> LENGTH: 939
<212> TYPE: DNA
<213> ORGANISM: Homo sapiens
<220> FEATURE:
<221> NAME/KEY: CDS
<222> LOCATION: (1)..(939)

<400> SEQUENCE: 9 atg cgg agg ggc gcg ctt ctg gcg ggc gcc ttg gcc gcg tac gcc gcg    48
Met Arg Arg Gly Ala Leu Leu Ala Gly Ala Leu Ala Ala Tyr Ala Ala
  1               5                  10                  15 tac ctg gtg ctg ggc gcg ctg ttg gtg gcg cgg ctg gag ggg ccg cac    96
Tyr Leu Val Leu Gly Ala Leu Leu Val Ala Arg Leu Glu Gly Pro His
                 20                  25                  30 gaa gcc agg ctc cga gcc gag ctg gag acg ctg cgg gcg cag ctg ctt   144
Glu Ala Arg Leu Arg Ala Glu Leu Glu Thr Leu Arg Ala Gln Leu Leu
             35                  40                  45 cag cgc agc ccg tgt gtg gct gcc ccc gcc ctg gac gcc ttc gtg gag   192
Gln Arg Ser Pro Cys Val Ala Ala Pro Ala Leu Asp Ala Phe Val Glu
         50                  55                  60 cga gtg ctg gcg gcc gga cgg ctg ggg cgg gtc gtg ctt gct aac gct   240
Arg Val Leu Ala Ala Gly Arg Leu Gly Arg Val Val Leu Ala Asn Ala
 65                  70                  75                  80
```

| | | |
|---|---|---|
| tcg ggg tcc gcc aac gcc tcg gac ccc gcc tgg gac ttc gcc tct gct<br>Ser Gly Ser Ala Asn Ala Ser Asp Pro Ala Trp Asp Phe Ala Ser Ala<br>                        85                          90                       95 | 288 |
| ctc ttc ttc gcc agc acg ctg atc acc acc gtg ggc tat ggg tac aca<br>Leu Phe Phe Ala Ser Thr Leu Ile Thr Thr Val Gly Tyr Gly Tyr Thr<br>           100                      105                      110 | 336 |
| acg cca ctg act gat gcg ggc aag gcc ttc tcc atc gcc ttt gcg ctc<br>Thr Pro Leu Thr Asp Ala Gly Lys Ala Phe Ser Ile Ala Phe Ala Leu<br>115                          120                      125 | 384 |
| ctg ggc gtg ccg acc acc atg ctg ctg acc gcc tca gcc cag cgc<br>Leu Gly Val Pro Thr Thr Met Leu Leu Leu Thr Ala Ser Ala Gln Arg<br>    130                      135                      140 | 432 |
| ctg tca ctg ctg ctg act cac gtg ccc ctg tct tgg ctg agc atg cgt<br>Leu Ser Leu Leu Leu Thr His Val Pro Leu Ser Trp Leu Ser Met Arg<br>145                      150                      155                      160 | 480 |
| tgg ggc tgg gac ccc cgg cgg gcg gcc tgc tgg cac ttg gtg gcc ctg<br>Trp Gly Trp Asp Pro Arg Arg Ala Ala Cys Trp His Leu Val Ala Leu<br>                  165                      170                      175 | 528 |
| ttg ggg gtc gta gtg acc gtc tgc ttt ctg gtg ccg gct gtg atc ttt<br>Leu Gly Val Val Val Thr Val Cys Phe Leu Val Pro Ala Val Ile Phe<br>    180                      185                      190 | 576 |
| gcc cac ctc gag gag gcc tgg agc ttc ttg gat gcc ttc tac ttc tgc<br>Ala His Leu Glu Glu Ala Trp Ser Phe Leu Asp Ala Phe Tyr Phe Cys<br>          195                      200                      205 | 624 |
| ttt atc tct ctg tcc acc atc ggc ctg ggc gac tac gtg ccc ggg gag<br>Phe Ile Ser Leu Ser Thr Ile Gly Leu Gly Asp Tyr Val Pro Gly Glu<br>    210                      215                      220 | 672 |
| gcc cct ggc cag ccc tac cgg gcc ctc tac aag gtg ctg gtc aca gtc<br>Ala Pro Gly Gln Pro Tyr Arg Ala Leu Tyr Lys Val Leu Val Thr Val<br>225                      230                      235                      240 | 720 |
| tac ctc ttc ctg ggc ctg gtg gcc atg gtg ctg gtg ctg cag acc ttc<br>Tyr Leu Phe Leu Gly Leu Val Ala Met Val Leu Val Leu Gln Thr Phe<br>                  245                      250                      255 | 768 |
| cgc cac gtg tcc gac ctc cac ggc ctc acg gag ctc atc ctg ctg ccc<br>Arg His Val Ser Asp Leu His Gly Leu Thr Glu Leu Ile Leu Leu Pro<br>          260                      265                      270 | 816 |
| cct ccg tgc cct gcc agt ttc aat gcg gat gag gac gat cgg gtg gac<br>Pro Pro Cys Pro Ala Ser Phe Asn Ala Asp Glu Asp Asp Arg Val Asp<br>    275                      280                      285 | 864 |
| atc ctg ggc ccc cag ccg gag tcg cac cag caa ctc tct gcc agc tcc<br>Ile Leu Gly Pro Gln Pro Glu Ser His Gln Gln Leu Ser Ala Ser Ser<br>290                      295                      300 | 912 |
| cac acc gac tac gct tcc atc ccc agg<br>His Thr Asp Tyr Ala Ser Ile Pro Arg<br>305                      310 | 939 |

<210> SEQ ID NO 10
<211> LENGTH: 1506
<212> TYPE: DNA
<213> ORGANISM: Homo sapiens
<220> FEATURE:
<221> NAME/KEY: CDS
<222> LOCATION: (157)..(1359)

<400> SEQUENCE: 10

| | |
|---|---|
| ctagggaggg cgccatctga gtagttcgga agaactgaac atgatgagtt gccggctgct | 60 |
| tcctgagtcc ttggggaagc acacgcacca tccacttagc actggagcct ggctgttctc | 120 |
| cgggcactcc taccccatct tcctggcggg gcttag atg ctc ctg cct ctt cca<br>                                                               Met Leu Leu Pro Leu Pro<br>                                                               1                      5 | 174 |

```
cca gct cct ctt gcc ctg cat gct tca ggg acg atg gag gtc tcg ggg     222
Pro Ala Pro Leu Ala Leu His Ala Ser Gly Thr Met Glu Val Ser Gly
        10                  15                  20 cac ccc cag gcc agg aga tgc tgc cca gag gcc ctg gga aag ctc ttc     270
His Pro Gln Ala Arg Arg Cys Cys Pro Glu Ala Leu Gly Lys Leu Phe
            25                  30                  35 cct ggc ctc tgc ttc ctc tgc ttt ctg gtg acc tac gcc ctg gtg ggt     318
Pro Gly Leu Cys Phe Leu Cys Phe Leu Val Thr Tyr Ala Leu Val Gly
    40                  45                  50 gct gtg gtc ttc tct gcc att gag gac ggc cag gtc ctg gtg gca gca     366
Ala Val Val Phe Ser Ala Ile Glu Asp Gly Gln Val Leu Val Ala Ala
55                  60                  65                  70 gat gat gga gag ttt gag aag ttc ttg gag gag ctc tgc aga atc ttg     414
Asp Asp Gly Glu Phe Glu Lys Phe Leu Glu Glu Leu Cys Arg Ile Leu
                75                  80                  85 aac tgc agt gaa aca gtg gtg gaa gac aga aaa cag gat ctc cag ggg     462
Asn Cys Ser Glu Thr Val Val Glu Asp Arg Lys Gln Asp Leu Gln Gly
            90                  95                 100 cat ctg cag aag gtg aag cct cag tgg ttt aac agg acc aca cac tgg     510
His Leu Gln Lys Val Lys Pro Gln Trp Phe Asn Arg Thr Thr His Trp
        105                 110                 115 tcc ttc ctg agc tcg ctc ttt ttc tgc tgc acg gtg ttc agc acc gtg     558
Ser Phe Leu Ser Ser Leu Phe Phe Cys Cys Thr Val Phe Ser Thr Val
    120                 125                 130 ggc tat ggc tac atc tac ccc gtc acc agg ctt ggc aag tac ttg tgc     606
Gly Tyr Gly Tyr Ile Tyr Pro Val Thr Arg Leu Gly Lys Tyr Leu Cys
135                 140                 145                 150 atg ctc tat gct ctc ttt ggt atc ccc ctg atg ttc ctc gtt ctc acg     654
Met Leu Tyr Ala Leu Phe Gly Ile Pro Leu Met Phe Leu Val Leu Thr
                155                 160                 165 gac aca ggc gac atc ctg gca acc atc tta tct aca tct tat aat cgg     702
Asp Thr Gly Asp Ile Leu Ala Thr Ile Leu Ser Thr Ser Tyr Asn Arg
            170                 175                 180 ttc cga aaa ttc cct ttc ttt acc cgc ccc ctc ctc tcc aag tgg tgc     750
Phe Arg Lys Phe Pro Phe Phe Thr Arg Pro Leu Leu Ser Lys Trp Cys
        185                 190                 195 ccc aaa tct ctc ttc aag aaa aaa ccg gac ccc aag ccc gca gat gaa     798
Pro Lys Ser Leu Phe Lys Lys Lys Pro Asp Pro Lys Pro Ala Asp Glu
    200                 205                 210 gct gtc cct cag atc atc atc agt gct gaa gag ctt cca ggc ccc aaa     846
Ala Val Pro Gln Ile Ile Ile Ser Ala Glu Glu Leu Pro Gly Pro Lys
215                 220                 225                 230 ctt ggc aca tgt cct tca cgc cca agc tgc agc atg gag ctg ttt gag     894
Leu Gly Thr Cys Pro Ser Arg Pro Ser Cys Ser Met Glu Leu Phe Glu
                235                 240                 245 aga tct cat gcg cta gag aaa cag aac aca ctg caa ctg ccc cca caa     942
Arg Ser His Ala Leu Glu Lys Gln Asn Thr Leu Gln Leu Pro Pro Gln
            250                 255                 260 gcc atg gag agg agt aac tcg tgt ccc gaa ctg gtg ttg gga aga ctc     990
Ala Met Glu Arg Ser Asn Ser Cys Pro Glu Leu Val Leu Gly Arg Leu
        265                 270                 275 tca tac tcc atc atc agc aac ctg gat gaa gtt gga cag cag gtg gag    1038
Ser Tyr Ser Ile Ile Ser Asn Leu Asp Glu Val Gly Gln Gln Val Glu
    280                 285                 290 agg ttg gac atc ccc ctc ccc atc att gcc ctt att gtt ttt gcc tac    1086
Arg Leu Asp Ile Pro Leu Pro Ile Ile Ala Leu Ile Val Phe Ala Tyr
295                 300                 305                 310 att tcc tgt gca gct gcc atc ctc ccc ttc tgg gag aca cag ttg gat    1134
Ile Ser Cys Ala Ala Ala Ile Leu Pro Phe Trp Glu Thr Gln Leu Asp
```

```
                        315                 320                 325
ttc gag aat gcc ttc tat ttc tgc ttt gtc aca ctc acc acc att ggg     1182
Phe Glu Asn Ala Phe Tyr Phe Cys Phe Val Thr Leu Thr Thr Ile Gly
                330                 335                 340 ttt ggg gat act gtt tta gaa cac cct aac ttc ttc ctg ttc ttc tcc     1230
Phe Gly Asp Thr Val Leu Glu His Pro Asn Phe Phe Leu Phe Phe Ser
            345                 350                 355 att tat atc atc gtt gga atg gag att gtg ttc att gct ttc aag ttg     1278
Ile Tyr Ile Ile Val Gly Met Glu Ile Val Phe Ile Ala Phe Lys Leu
    360                 365                 370 gtg caa aac agg ctg att gac ata tac aaa aat gtt atg cta ttc ttt     1326
Val Gln Asn Arg Leu Ile Asp Ile Tyr Lys Asn Val Met Leu Phe Phe
375                 380                 385                 390 gca aaa ggg aag ttt tac cac ctt gtt aaa aag tgaaggtttc attatctctc   1379
Ala Lys Gly Lys Phe Tyr His Leu Val Lys Lys
                395                 400 aggtgacaga cactggctga gctggttttc ttgtgttgtc tttcagggtc atgcagcctg   1439
tcacctgaga ccttcagtct tggagacaaa tcccttatga gagccaagtt cagtcttgag   1499
gccctgc                                                             1506

<210> SEQ ID NO 11
<211> LENGTH: 401
<212> TYPE: PRT
<213> ORGANISM: Homo sapiens

<400> SEQUENCE: 11

Met Leu Leu Pro Leu Pro Pro Ala Pro Leu Ala Leu His Ala Ser Gly
1               5                   10                  15

Thr Met Glu Val Ser Gly His Pro Gln Ala Arg Arg Cys Cys Pro Glu
                20                  25                  30

Ala Leu Gly Lys Leu Phe Pro Gly Leu Cys Phe Leu Cys Phe Leu Val
            35                  40                  45

Thr Tyr Ala Leu Val Gly Ala Val Phe Ser Ala Ile Glu Asp Gly
        50                  55                  60

Gln Val Leu Val Ala Ala Asp Asp Gly Glu Phe Glu Lys Phe Leu Glu
65                  70                  75                  80

Glu Leu Cys Arg Ile Leu Asn Cys Ser Glu Thr Val Val Glu Asp Arg
                85                  90                  95

Lys Gln Asp Leu Gln Gly His Leu Gln Lys Val Lys Pro Gln Trp Phe
            100                 105                 110

Asn Arg Thr Thr His Trp Ser Phe Leu Ser Ser Leu Phe Phe Cys Cys
        115                 120                 125

Thr Val Phe Ser Thr Val Gly Tyr Gly Tyr Ile Tyr Pro Val Thr Arg
    130                 135                 140

Leu Gly Lys Tyr Leu Cys Met Leu Tyr Ala Leu Phe Gly Ile Pro Leu
145                 150                 155                 160

Met Phe Leu Val Leu Thr Asp Thr Gly Asp Ile Leu Ala Thr Ile Leu
                165                 170                 175

Ser Thr Ser Tyr Asn Arg Phe Arg Lys Phe Pro Phe Thr Arg Pro
            180                 185                 190

Leu Leu Ser Lys Trp Cys Pro Lys Ser Leu Phe Lys Lys Lys Pro Asp
        195                 200                 205

Pro Lys Pro Ala Asp Glu Ala Val Pro Gln Ile Ile Ile Ser Ala Glu
    210                 215                 220

Glu Leu Pro Gly Pro Lys Leu Gly Thr Cys Pro Ser Arg Pro Ser Cys
```

```
                225                 230                 235                 240
Ser Met Glu Leu Phe Glu Arg Ser His Ala Leu Glu Lys Gln Asn Thr
                    245                 250                 255

Leu Gln Leu Pro Pro Gln Ala Met Glu Arg Ser Asn Ser Cys Pro Glu
                260                 265                 270

Leu Val Leu Gly Arg Leu Ser Tyr Ser Ile Ile Ser Asn Leu Asp Glu
            275                 280                 285

Val Gly Gln Gln Val Glu Arg Leu Asp Ile Pro Leu Pro Ile Ile Ala
        290                 295                 300

Leu Ile Val Phe Ala Tyr Ile Ser Cys Ala Ala Ile Leu Pro Phe
305                 310                 315                 320

Trp Glu Thr Gln Leu Asp Phe Glu Asn Ala Phe Tyr Phe Cys Phe Val
                325                 330                 335

Thr Leu Thr Thr Ile Gly Phe Gly Asp Thr Val Leu Glu His Pro Asn
                340                 345                 350

Phe Phe Leu Phe Phe Ser Ile Tyr Ile Ile Val Gly Met Glu Ile Val
                355                 360                 365

Phe Ile Ala Phe Lys Leu Val Gln Asn Arg Leu Ile Asp Ile Tyr Lys
            370                 375                 380

Asn Val Met Leu Phe Phe Ala Lys Gly Lys Phe Tyr His Leu Val Lys
385                 390                 395                 400

Lys

<210> SEQ ID NO 12
<211> LENGTH: 1203
<212> TYPE: DNA
<213> ORGANISM: Homo sapiens
<220> FEATURE:
<221> NAME/KEY: CDS
<222> LOCATION: (1)..(1203)

<400> SEQUENCE: 12 atg ctc ctg cct ctt cca cca gct cct ctt gcc ctg cat gct tca ggg      48
Met Leu Leu Pro Leu Pro Pro Ala Pro Leu Ala Leu His Ala Ser Gly
1               5                   10                  15 acg atg gag gtc tcg ggg cac ccc cag gcc agg aga tgc tgc cca gag      96
Thr Met Glu Val Ser Gly His Pro Gln Ala Arg Arg Cys Cys Pro Glu
            20                  25                  30 gcc ctg gga aag ctc ttc cct ggc ctc tgc ttc ctc tgc ttt ctg gtg     144
Ala Leu Gly Lys Leu Phe Pro Gly Leu Cys Phe Leu Cys Phe Leu Val
        35                  40                  45 acc tac gcc ctg gtg ggt gct gtg gtc ttc tct gcc att gag gac ggc     192
Thr Tyr Ala Leu Val Gly Ala Val Val Phe Ser Ala Ile Glu Asp Gly
    50                  55                  60 cag gtc ctg gtg gca gca gat gat gga gag ttt gag aag ttc ttg gag     240
Gln Val Leu Val Ala Ala Asp Asp Gly Glu Phe Glu Lys Phe Leu Glu
65                  70                  75                  80 gag ctc tgc aga atc ttg aac tgc agt gaa aca gtg gtg gaa gac aga     288
Glu Leu Cys Arg Ile Leu Asn Cys Ser Glu Thr Val Val Glu Asp Arg
                85                  90                  95 aaa cag gat ctc cag ggg cat ctg cag aag gtg aag cct cag tgg ttt     336
Lys Gln Asp Leu Gln Gly His Leu Gln Lys Val Lys Pro Gln Trp Phe
            100                 105                 110 aac agg acc aca cac tgg tcc ttc ctg agc tcg ctc ttt ttc tgc tgc     384
Asn Arg Thr Thr His Trp Ser Phe Leu Ser Ser Leu Phe Phe Cys Cys
        115                 120                 125 acg gtg ttc agc acc gtg ggc tat ggc tac atc tac ccc gtc acc agg     432
Thr Val Phe Ser Thr Val Gly Tyr Gly Tyr Ile Tyr Pro Val Thr Arg
```

```
                 130                 135                 140
ctt ggc aag tac ttg tgc atg ctc tat gct ctc ttt ggt atc ccc ctg     480
Leu Gly Lys Tyr Leu Cys Met Leu Tyr Ala Leu Phe Gly Ile Pro Leu
145                 150                 155                 160 atg ttc ctc gtt ctc acg gac aca ggc gac atc ctg gca acc atc tta     528
Met Phe Leu Val Leu Thr Asp Thr Gly Asp Ile Leu Ala Thr Ile Leu
                165                 170                 175 tct aca tct tat aat cgg ttc cga aaa ttc cct ttc ttt acc cgc ccc     576
Ser Thr Ser Tyr Asn Arg Phe Arg Lys Phe Pro Phe Phe Thr Arg Pro
            180                 185                 190 ctc ctc tcc aag tgg tgc ccc aaa tct ctc ttc aag aaa aaa ccg gac     624
Leu Leu Ser Lys Trp Cys Pro Lys Ser Leu Phe Lys Lys Lys Pro Asp
        195                 200                 205 ccc aag ccc gca gat gaa gct gtc cct cag atc atc atc agt gct gaa     672
Pro Lys Pro Ala Asp Glu Ala Val Pro Gln Ile Ile Ile Ser Ala Glu
    210                 215                 220 gag ctt cca ggc ccc aaa ctt ggc aca tgt cct tca cgc cca agc tgc     720
Glu Leu Pro Gly Pro Lys Leu Gly Thr Cys Pro Ser Arg Pro Ser Cys
225                 230                 235                 240 agc atg gag ctg ttt gag aga tct cat gcg cta gag aaa cag aac aca     768
Ser Met Glu Leu Phe Glu Arg Ser His Ala Leu Glu Lys Gln Asn Thr
                245                 250                 255 ctg caa ctg ccc cca caa gcc atg gag agg agt aac tcg tgt ccc gaa     816
Leu Gln Leu Pro Pro Gln Ala Met Glu Arg Ser Asn Ser Cys Pro Glu
            260                 265                 270 ctg gtg ttg gga aga ctc tca tac tcc atc atc agc aac ctg gat gaa     864
Leu Val Leu Gly Arg Leu Ser Tyr Ser Ile Ile Ser Asn Leu Asp Glu
        275                 280                 285 gtt gga cag cag gtg gag agg ttg gac atc ccc ctc ccc atc att gcc     912
Val Gly Gln Gln Val Glu Arg Leu Asp Ile Pro Leu Pro Ile Ile Ala
    290                 295                 300 ctt att gtt ttt gcc tac att tcc tgt gca gct gcc atc ctc ccc ttc     960
Leu Ile Val Phe Ala Tyr Ile Ser Cys Ala Ala Ala Ile Leu Pro Phe
305                 310                 315                 320 tgg gag aca cag ttg gat ttc gag aat gcc ttc tat ttc tgc ttt gtc    1008
Trp Glu Thr Gln Leu Asp Phe Glu Asn Ala Phe Tyr Phe Cys Phe Val
                325                 330                 335 aca ctc acc acc att ggg ttt ggg gat act gtt tta gaa cac cct aac    1056
Thr Leu Thr Thr Ile Gly Phe Gly Asp Thr Val Leu Glu His Pro Asn
            340                 345                 350 ttc ttc ctg ttc ttc tcc att tat atc atc gtt gga atg gag att gtg    1104
Phe Phe Leu Phe Phe Ser Ile Tyr Ile Ile Val Gly Met Glu Ile Val
        355                 360                 365 ttc att gct ttc aag ttg gtg caa aac agg ctg att gac ata tac aaa    1152
Phe Ile Ala Phe Lys Leu Val Gln Asn Arg Leu Ile Asp Ile Tyr Lys
    370                 375                 380 aat gtt atg cta ttc ttt gca aaa ggg aag ttt tac cac ctt gtt aaa    1200
Asn Val Met Leu Phe Phe Ala Lys Gly Lys Phe Tyr His Leu Val Lys
385                 390                 395                 400 aag                                                                1203
Lys
```